United States Patent
Heise et al.

(10) Patent No.: US 6,238,637 B1
(45) Date of Patent: May 29, 2001

(54) PROCESS AND APPARATUS FOR PREPARATION OF PHOSPHORUS OXYACIDS FROM ELEMENTAL PHOSPHORUS

(75) Inventors: Jerald Heise, St. Louis; Erik D. Sall, Chesterfield; Martin P. McGrath, St. Louis, all of MO (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 09/250,254

(22) Filed: Feb. 16, 1999

Related U.S. Application Data

(60) Provisional application No. 60/076,089, filed on Feb. 26, 1998, and provisional application No. 60/099,043, filed on Sep. 3, 1998.

(51) Int. Cl.⁷ .................................................. C01B 25/16
(52) U.S. Cl. ........................................... 423/316; 423/304
(58) Field of Search ................................. 423/316, 304, 423/317

(56) References Cited

U.S. PATENT DOCUMENTS

| | | |
|---|---|---|
| 1,605,960 | 11/1926 | Liljenroth . |
| 1,673,691 | 6/1928 | Liljenroth . |
| 1,680,625 | 8/1928 | Lang . |
| 1,732,373 | 10/1929 | Mittasch et al. . |
| 1,807,790 | 6/1931 | Liljenroth . |
| 1,815,581 | 7/1931 | Pauckner et al. . |
| 1,823,923 | 9/1931 | Wild et al. . |
| 1,848,295 | 3/1932 | Ipatiew . |
| 1,895,329 | 1/1933 | Ipatieff . |
| 1,916,594 | 7/1933 | Wietzel et al. . |
| 2,272,414 | 2/1942 | McCullough ........................... 23/165 |
| 2,374,188 | 4/1945 | Frear ....................................... 23/165 |
| 2,613,134 | 10/1952 | Elmore .................................... 23/165 |
| 2,613,135 | 10/1952 | Schultz ................................... 23/165 |
| 2,706,146 | 4/1955 | Hein et al. .............................. 23/165 |
| 3,351,554 | * 11/1967 | Myers ................................... 508/419 |
| 3,369,868 | 2/1968 | Kegan .................................... 23/165 |
| 4,207,300 | 6/1980 | Kestner et al. ....................... 423/299 |
| 4,252,770 | 2/1981 | Thümmler et al. .................. 422/194 |
| 4,980,142 | 12/1990 | McGilvery et al. ................. 423/316 |

FOREIGN PATENT DOCUMENTS

| | | | |
|---|---|---|---|
| 0 010 217 | 10/1979 | (EP) .............................. | C01B/25/20 |
| 0 303 362 | 7/1988 | (EP) .............................. | C01B/25/12 |

OTHER PUBLICATIONS

Hein, et al., Industrial and Engineering Chemistry, "Oxidation of Phosphorus with Steam," vol. 42, No. 8, Apr. 7, 1950, pp. 1616–1622.
Pourbaix, "Atlas of Electrochemical Equilibria," Section 18.2, Phosphorus, 1974, pp. 504–523.
Chemical News, "Pictorial History of Ancient Pharmacy," May 2, 1990, pp. 214–215.
Schultz, et al., Industrial and Engineering Chemistry, "Oxidation of Phosphorus with Steam: Laboratory Scale Research," vol. 42, No. 8, Aug. 13, 1949, pp. 1608–1615.
Kroeger, Excerpt from Z. anorg. allg. Chemie, "Heterogeneous Catalysis of Binary Gas Reactions," vol. 206, 1932, pp. 289–303.
Brunauer et al., Industrial and Engineering Chemistry, "Oxidation of Phosphorus by Steam: Investigation of the Gas–Phase Oxidation in the Presence and Absence of Phosphate Rock," vol. 33, No. 6, Jun. 1941, pp. 828–832.
MacRae et al., Research Laboratory, "Vapor Pressure of White Phosphorus from 44° to 150°," Jan. 20, 1921, pp. 547–553.
Emmett et al., Industrial and Engineering Chemistry, "Oxidation of Phosphorus to a Pentavalent Form by Carbon Dioxide," vol. 31, 1939 pp. 105–111.
Frear et al., Industrial and Engineering Chemistry, "Preferential Oxidation Phosphorus in Presence of Carbon Monoxide," vol. 36, No. 10, Oct. 1944, pp. 927–933.
Leeds, American Chemists, "Contributions to the Chemistry of Hydrogen," Nov. 1876, pp. 183–186.
Gmelin, CU Series, "Copper Phosphide, $Cu_3P$: Formation and Preparation of Copper," vol. B2 CU Series, 1961, pp. 1913–1919.
Scholder, et al., Z. Anorg. Chem., "Addition of Hydrogen Phosphide to Cu(I) and Silver Halide," vol. 220, 1934, 250–56.
Christomanos, Z. Anorg. Chem., "Quantitative Determination of Phosphorus in Solutions," vol. 41, 1904, pp. 305–314.
Chene, Ann. Chim., "Investigations of the Preparations of Metal Phosphides by Igneous Electrolysis," 14th Series, vol. 15, May/Jun. 1941, pp. 187–197.
Chene, Acad. Sci., "Preparation of Copper Phosphides by Igneous Electrolysis," Jul. 1942, 81–83.
Chene, J. Acad. Sci., "Preparation of Copper Phosphides by Igneous Electrolysis," Jun. 1942, pp. 977–979.
Gupta, Ind. J. Chem., "Kinetics of Oxidation of Hypophosphorus and Phosphorous Acids by Mn(III) Sulphate," vol. 15A, Jun. 1976, pp. 510–512.

(List continued on next page.)

*Primary Examiner*—Jean F. Vollano
(74) *Attorney, Agent, or Firm*—Senniger, Powers, Leavitt & Roedel

(57) ABSTRACT

A process for the preparation of an oxyacid of phosphorus comprising contacting elemental phosphorus with water in the presence of a catalyst effective to promote oxidation of phosphorus by reaction with water. The use of a noble metal catalyst such as Pd under moderate agitation and low severity conditions is effective for the preparation of P(III) oxyacid in high selectivity. Other suitable catalysts may comprise, for example, other Group VIII metals (particularly other platinum metals); oxides, salts, phosphides, and/or coordination compounds of Group VIII metals; Group IB metals; and/or oxides, salts, phosphides, and/or coordination compounds of Group IB metals. Various apparatus and process as schemes for the preparation of phosphoric and phosphorous acid are also disclosed.

127 Claims, 32 Drawing Sheets-

OTHER PUBLICATIONS

Alemany, et al., A. Chem. Soc., "Electronic Structure, Bonding and Properties of $CuP_2$," vol. 31, No. 1, 1992, pp. 119–124.

Mehretra, J. Chem. Soc., "Kinetics and Mechanisms of Redox Reactions in Aqueous Solution. Part 9. Permanganate Oxidation of Phosphorus Acid in Perchlorate Solution," 1983, pp. 1521–1535.

Scherer, et al., "$P_4$ Activation with [{Cp'''$(OC)_2$Fe}$_2$] (Cp''' = $C_5H_2Bu^t3$–1,2,4): Exclusive Formation of the Exo/Exo–Butterfly Complex [{Cp'''$(OC)_2$Fe}$2(\mu-\eta^1:\eta^1-P_4)$]," Organometallics, vol. 17, 1998, pp. 4110–4112.

Peruzzini, et al., "Hydrogenation of White Phosphorus to Phosphane with Rhodium and Iridium Trihydrides," Angew. Chem. Int. Ed., 37, No. 16, 1998, pp. 2255–2257.

Scherer, "Complexes with Substituent–free Acyclic and Cyclic Phosphorus, Arsenic, Antimony, and Bismuth Ligands," Angew. Chem. Int. Ed. Engl. 29, 1990, pp. 1104–1122.

Fritz, et al., "Electrochemical Deposition of Copper Phosphides," Monatshefte für Chemie 123, 1992, pp. 397–403.

Svehla, P. "Preparative Verwertung Der Reaktion von Jod Mit Phosphin Im Wassrigen Medium," Collection Czechoslov, Chem. Commun., vol. 31, 1966, pp. 4712–4717; English abstract att'd.

Engel, M.R., Comptes Rendus Academy of Science, pp. 786–787 Jan.–Jun. 1890 (with English translation).

* cited by examiner

FIG. 24 STIRRED TANK CONFIGURATION

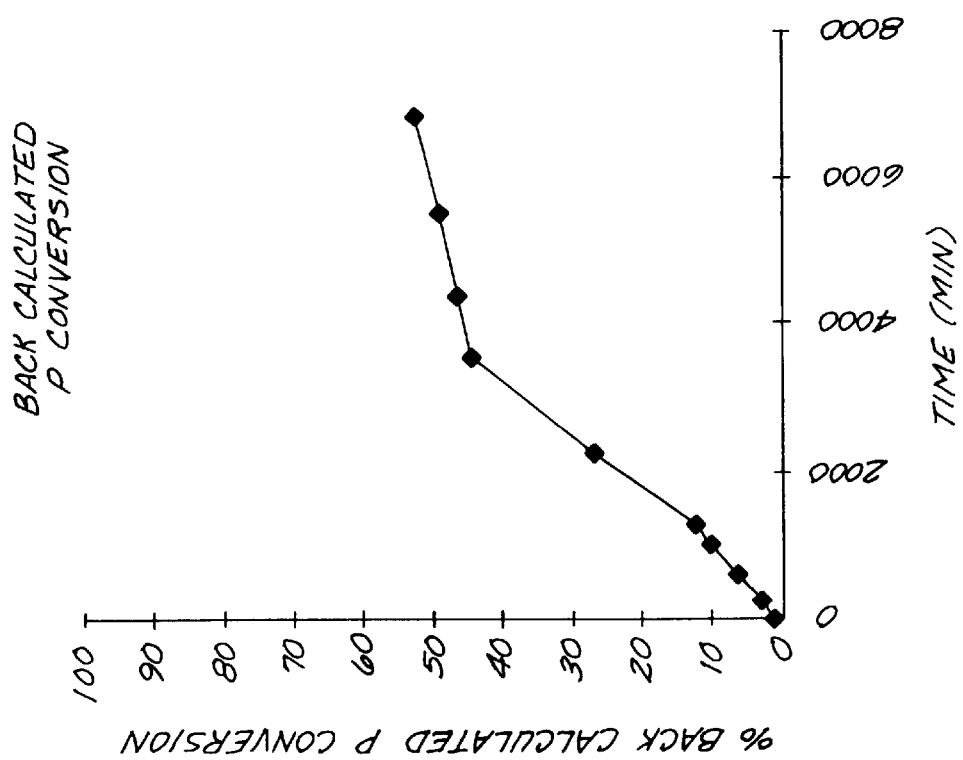
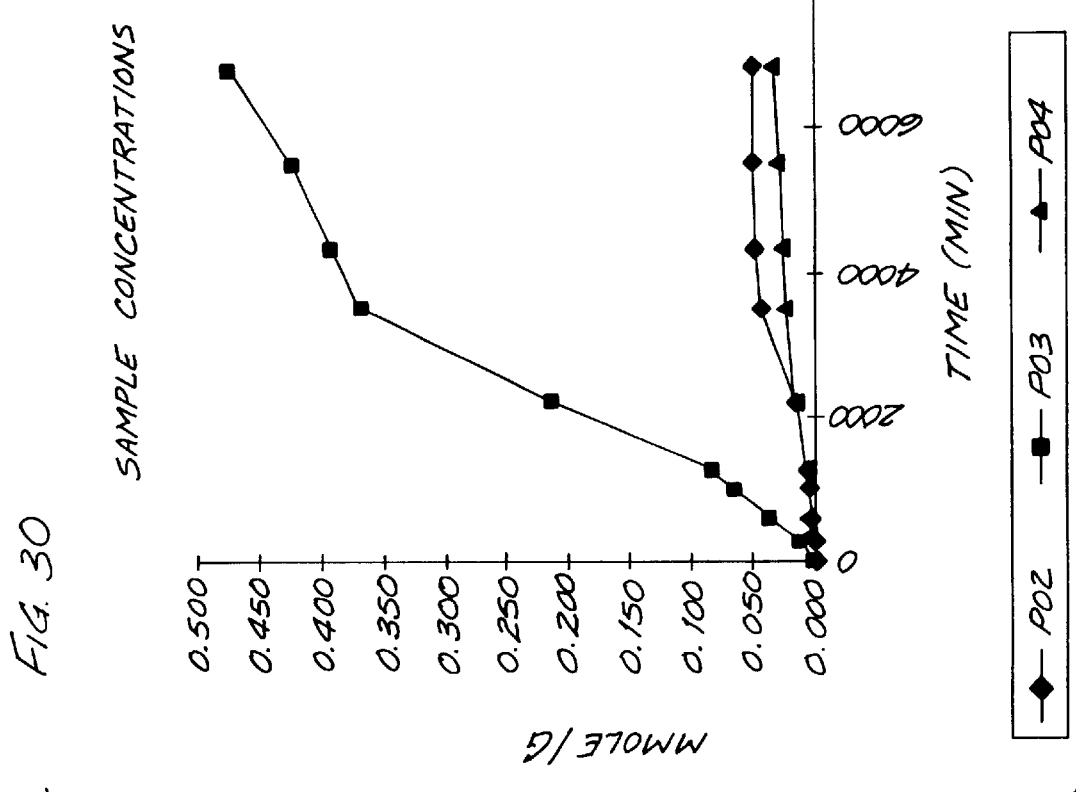
FIG. 30

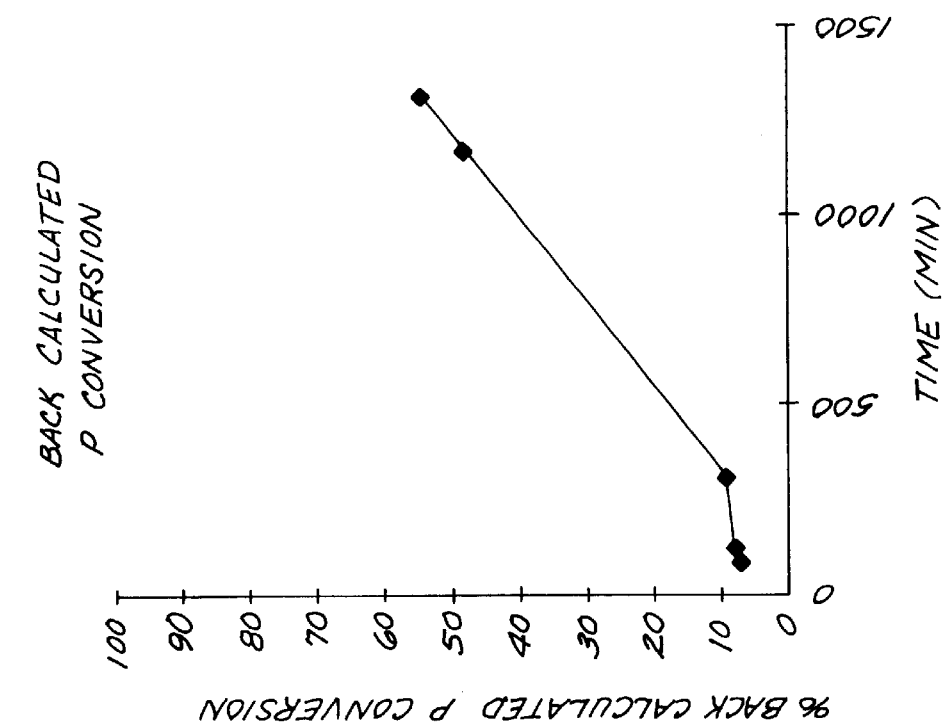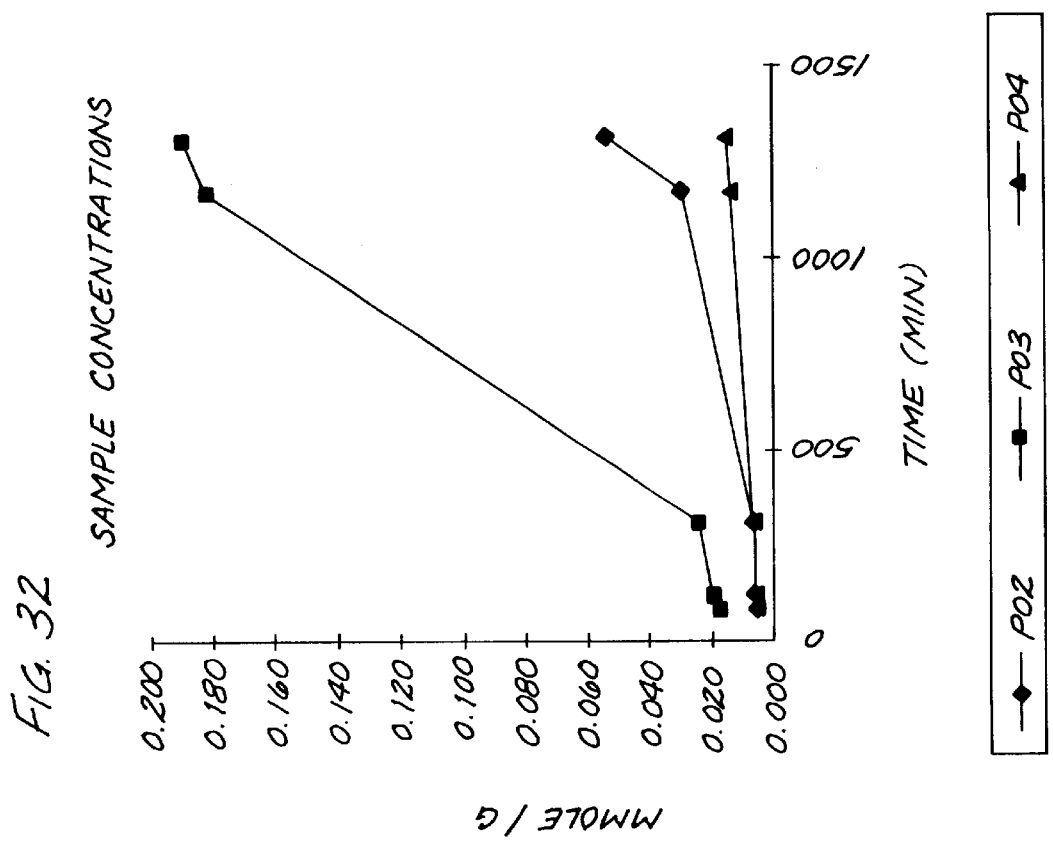
FIG. 32

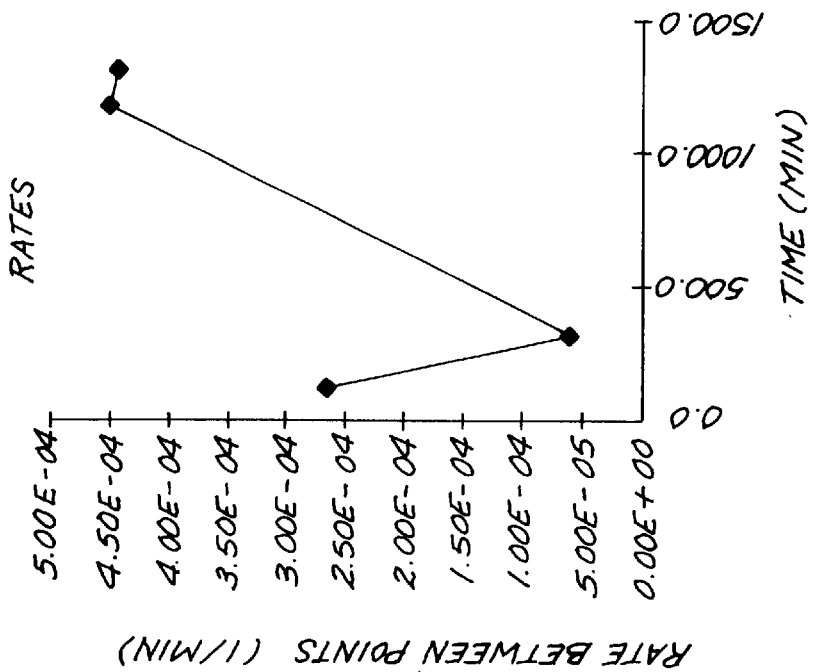
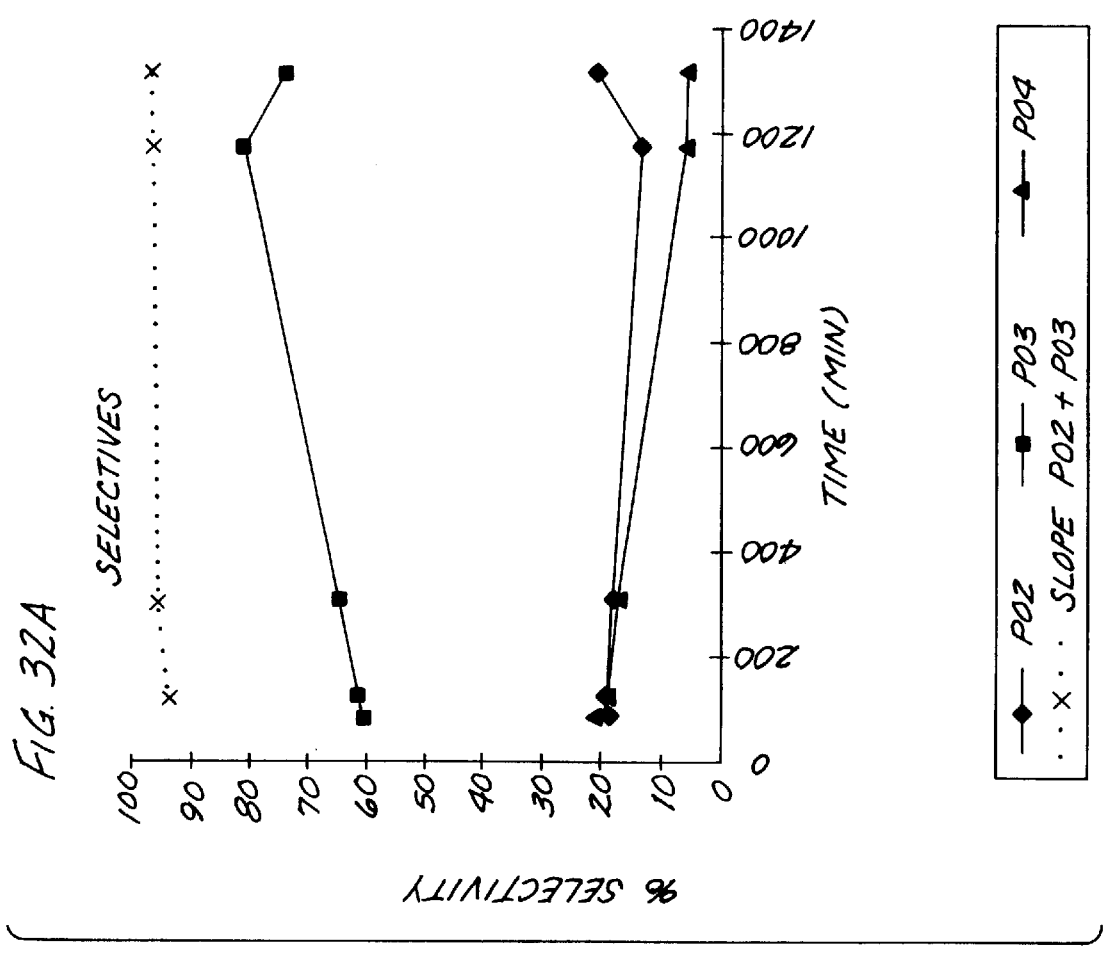
FIG. 32A

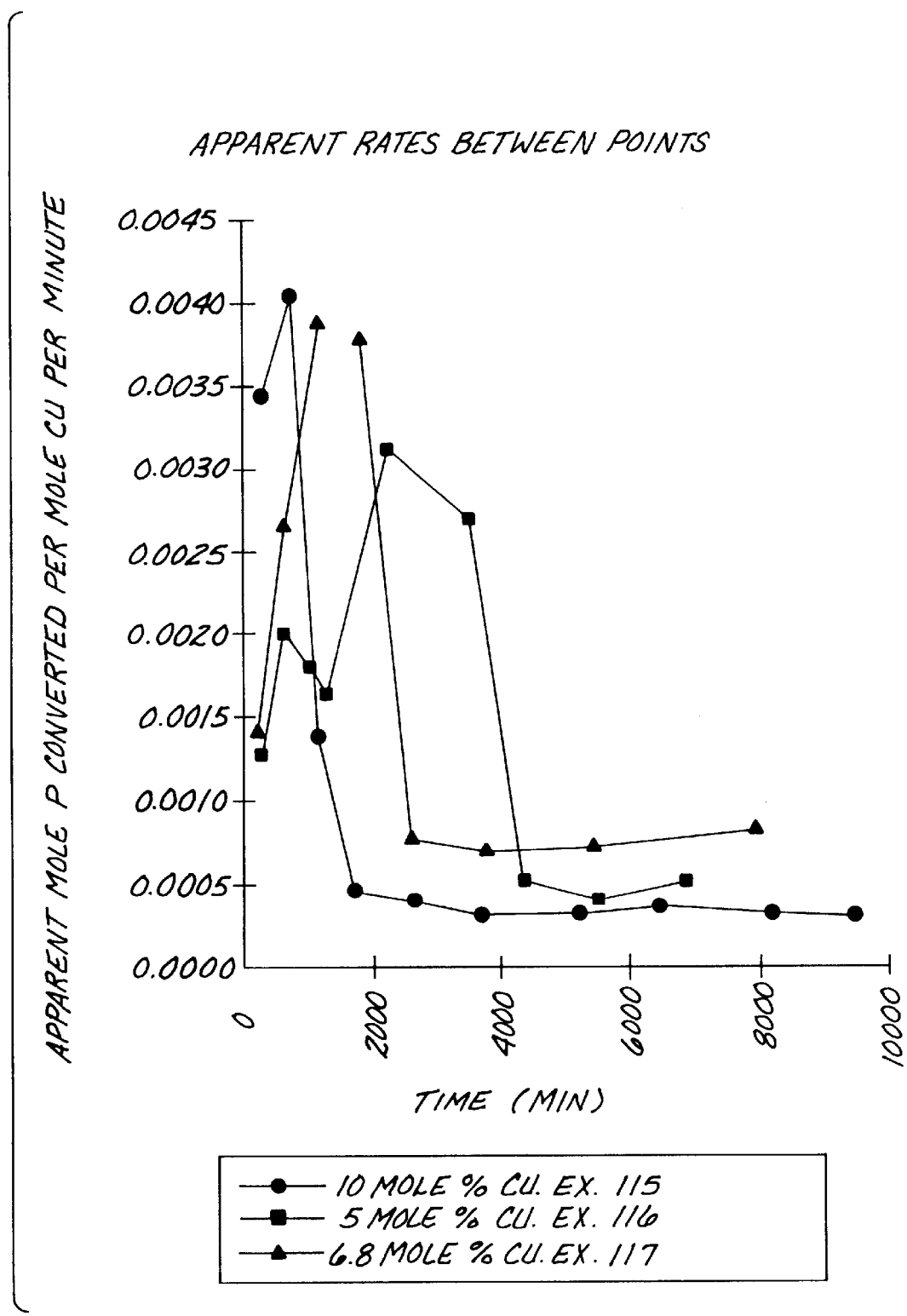

PROCESS AND APPARATUS FOR PREPARATION OF PHOSPHORUS OXYACIDS FROM ELEMENTAL PHOSPHORUS

CROSS REFERENCES TO RELATED PATENT APPLICATIONS

This patent claims priority from U.S. Provisional Patent Application Serial No. 60/076,089 (filed Feb. 26, 1998) and U.S. Provisional Patent Application Serial No. 60/099,043 (filed Sep. 3, 1998). The complete texts of both these provisional patent applications are hereby incorporated herein by reference.

BACKGROUND OF THE INVENTION

This invention relates to the preparation of phosphorus oxyacids, and more particularly to novel processes for the preparation of oxyacids by catalytic reaction of water and elemental phosphorus.

Oxyacids of phosphorus are important precursors for the synthesis of other phosphorus species having various applications, for example, in herbicides, insecticides, fertilizers, flame retardants and plasticizers.

Phosphoric acid for use in fertilizer manufacture is conventionally prepared by acidulation of phosphate rock with sulfuric acid, resulting in substantial generation of by-product gypsum or calcium sulfate hemihydrate which must be disposed of either as a by-product or waste material. Environmental and corrosion issues may also arise from the generation of HF by acidulation of fluoride contained within phosphate rock.

Higher purity phosphoric acid is produced by oxidation of elemental phosphorus to phosphorus pentoxide, and absorption of phosphorus pentoxide in dilute phosphoric acid. This process requires a combustion furnace in which phosphorus is burned to phosphorus pentoxide at temperatures in excess of 3500° F., and is generally adapted for the production of phosphoric acid only on a large scale.

Phosphorous acid has been conventionally manufactured by hydrolyzing a halogen derivative of phosphorus, such as phosphorus trichloride. Since the halogen derivatives are prepared from elemental phosphorus, an economic advantage could be realized by preparing phosphorous acid directly from elemental phosphorus. Direct preparation could also provide environmental benefits by avoiding the use of halogen-containing phosphorus starting materials and production of halogen-containing by-products.

As described by Engel, "Oxidation of Hypophosphorous Acid by Hydrogenated Palladium in the Absence of Oxygen," Comet. Rend. Acad. Sci., 1890, pp. 786–787, phosphorous acid can also be prepared by oxidation of hypophosphorous acid with water in the presence of a palladium catalyst. However, commercial processes are not readily available for the economical preparation of the hypophosphorous acid starting material without formation of phosphine or other undesirable by-products.

Christomanos (Z. Anorg. Chem., 41, 305–14, 1904) describes an analytical procedure for determination of elemental phosphorus in organic solutions by a metal induced disproportionation to phosphorous acid and a Cu phosphide:

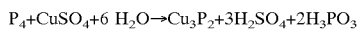
$P_4 + CuSO_4 + 6\ H_2O \rightarrow Cu_3P_2 + 3H_2SO_4 + 2H_3PO_3$

Comparable reactions of elemental phosphorus with $Cu_2NO_3$ are also disclosed. Only stoichiometric reactions are described. Atmospheric oxygen is said to have an oxidizing function. After four hours, Cu phosphide disappears and the solution contains only Cu phosphate.

White phosphorus, the elemental phosphorus allotrope also referred to as yellow phosphorus or tetraphosphorus ($P_4$), is a potential starting point for the synthesis of a variety of phosphorus species. The tetrahedral structure of white phosphorus contains six phosphorus-phosphorus bonds and can provide a large number of reactive species having an intermediate existence in phosphorus reactions. As noted, tetraphosphorus is the raw material for one of the major commercial processes for the manufacture of phosphoric acid. If tetraphosphorus could be used as a starting material for the manufacture of other oxyacids of phosphorus without intermediate halogenation, significant economic advantages might be realized, especially if the reaction could be conducted under relatively mild conditions. However, in the exothermic reaction of phosphorus with oxygen, it is difficult to control the reaction short of the formation of the P(V) oxide, i.e., the anhydride of phosphoric acid.

Ipatiev U.S. Pat. Nos. 1,848,295 and 1,895,329 describe processes for the preparation of phosphoric acid by catalytic oxidation of liquid phosphorus with water at high temperature and pressure. Catalysts include salts of copper and nickel, copper or nickel phosphide being formed in the reaction. Ipatiev reports that phosphorous acid is formed as an undesired by-product of the oxidation reaction, particularly early in the reaction, but does not disclose the fraction of phosphorous acid present in the reaction mixture, or the relative proportions of phosphorous and phosphoric acid present, at any time during the reaction. Ipatiev teaches that the reaction is preferably conducted at temperatures of 300° C. or above, but the '329 patent includes an example at 200° C. in which by-product copper phosphide is found in the phosphorus phase at the end of the reaction.

Numerous references describe the preparation of phosphoric acid by catalytic vapor phase oxidation of phosphorus with water at temperatures above 600° C., commonly above 1000° C. Various catalysts are disclosed to for use in these reactions, including copper, silver and a wide variety of other metals, particularly other Group IB and Group VIII metals, certain Group VI metals (e.g., Cr, Mo, W and U), certain Group VII metals (e.g., Mn), and/or their oxides, salts and/or phosphides. To prevent leaching of catalyst out of the reaction zone, it has been proposed to use various supports for active catalysts, including, for example, pyrophosphates of Ti or Zr. Liljenroth U.S. Pat. No. 1,605,960, e.g., also lists noble metals such as Ru, Rh, Pd, Os, Ir or Pt as catalysts for the reaction.

SUMMARY OF THE INVENTION

Among the several objects of the present invention may be noted the provision of an improved process for the manufacture of oxyacids of phosphorus; the provision of such a process which can be controlled to produce lower oxyacids of phosphorus, especially phosphorous acid; the provision of such a process which can be controlled to produce phosphorous acid in high selectivity; the provision of such a process which can be controlled to produce phosphorous acid in high yield; the provision of such a process which can be operated to produce phosphorous acid in reasonably high concentration; the provision of such a process which can be operated with minimal environmental emissions; and the provision of such a process which does not use halogen-bearing raw materials or produce halogenated by-products.

Briefly, therefore, the present invention is directed to a process for the preparation of an oxyacid of phosphorus comprising oxidizing elemental phosphorus by catalytic reaction with water at a temperature below 200° C.

The invention is further directed to a process for the preparation of phosphorous acid comprising catalytically oxidizing elemental phosphorus by reaction with water under conditions effective to produce an oxidation reaction mixture comprising a lower phosphorus oxidation product, the ratio of the sum of the concentrations of P(I) and P(III) species to the concentration of P(V) species in said reaction mixture being least about five.

The invention is also directed to a process for the preparation of an oxyacid of phosphorus comprising contacting condensed phase elemental phosphorus with water at pressure below about 20 atm in the presence of a catalyst for the oxidation of phosphorus by reaction with water. Elemental phosphorus is catalytically oxidized by reaction with water.

The invention is also directed to a process for the preparation of an oxyacid of phosphorus comprising oxidizing elemental phosphorus by catalytic reaction with water in a catalytic reaction zone to produce a lower phosphorus oxidation product at a rate of at least 0.01 kg/hr per unit volume of said reaction zone as expressed in $m^3$.

The invention is also directed to a process for the preparation of an oxyacid of phosphorus comprising catalytically oxidizing elemental phosphorus in a continuous catalytic reaction zone to produce a lower phosphorus oxidation at a rate of at least $1 \times 10^{-7}$ kg/hr-g catalyst.

The invention is further directed to a process for the preparation of phosphorous acid comprising catalytically oxidizing elemental phosphorus with water, thereby producing an aqueous reaction mixture comprising at least 5% by weight of a lower phosphorus oxidation product, the reaction between phosphorus and water being conducted in a heterogeneous reaction system comprising a water phase and a condensed phase comprising elemental phosphorus, said condensed phase containing a catalyst for the reaction.

The invention is also directed to a process for the preparation of an oxyacid of phosphorus comprising contacting a condensed phase comprising elemental phosphorus with an aqueous phase in the presence of a catalyst for the oxidation of phosphorus by reaction with water, active sites of the catalyst being maintained in contact with the condensed phase comprising phosphorus preferentially to said aqueous phase during the catalytic oxidation reaction.

The invention is further directed to a process for the preparation of an oxyacid of phosphorus comprising contacting a condensed phase comprising elemental phosphorus with an aqueous phase in the presence of a catalyst for the oxidation of phosphorus by reaction with water, the catalytic oxidation reaction occurring preferentially in said elemental phosphorus phase.

The invention is further directed to an apparatus for oxidation of elemental phosphorus to oxyacids of phosphorus. The apparatus comprises a liquid/liquid contact zone for contacting an aqueous phase reagent with a substantially water-immiscible condensed phase comprising tetraphosphorus; and a catalytic reaction zone for contacting the water-immiscible condensed phase with a catalyst for the oxidation of elemental phosphorus by reaction with water.

The invention is particularly directed to an apparatus comprising a reservoir for a body of a substantially water-immiscible liquid containing elemental phosphorus, and means for introducing an aqueous liquid into the reservoir for flowing across a surface of the body of liquid containing elemental phosphorus. As the aqueous phase flows across the surface of the body of the water-immiscible liquid, water may be transferred from the aqueous phase to the phase comprising elemental phosphorus, and phosphorus oxidation products may be transferred from the phase comprising elemental phosphorus to the aqueous phase. The reservoir is configured to provide an interfacial contact area between the liquid phases sufficient for the reaction. A catalyst bed is in contact with the water-immiscible liquid remote from the interface. The catalyst bed comprises a catalyst for the oxidation of elemental phosphorus by reaction with water.

The invention is further particularly directed to an apparatus comprising a reactant reservoir for an aqueous phase and a separate phase comprising elemental phosphorus. Means within the reservoir promotes mass transfer between the aqueous phase and the phase comprising elemental phosphorus. A fixed catalyst bed remote from the reservoir comprises a catalyst for the reaction. The apparatus further comprises means for circulating the phase comprising elemental phosphorus between the reservoir and the catalyst bed.

The invention is further directed to an apparatus for oxidation of elemental phosphorus to oxyacids of phosphorus comprising a catalyst slurry tank for a mixture of elemental phosphorus and catalyst for the oxidation of phosphorus by reaction with water, and a heterogeneous liquid phase reactor comprising a countercurrent liquid/liquid contact zone. The liquid phase reactor has an inlet for an aqueous liquid, an exit for an aqueous solution of phosphorus oxyacids, an inlet for a phosphorus phase, and an exit for a phosphorus phase. The apparatus further comprises means for circulating a phosphorus phase between the phosphorus phase exit of the liquid phase reactor, the catalyst slurry tank, and the phosphorus phase inlet of the reactor.

The invention is further directed to a composition effective for use in the manufacture of oxyacids of phosphorus. The composition comprises a mixture containing elemental phosphorus and a catalyst for the oxidation of elemental phosphorus by reaction with water.

The invention is also directed to apparatus for oxidation of elemental phosphorus to oxyacids of phosphorus comprising a reactor having a fixed catalyst bed positioned therein, said catalyst bed comprising a catalyst for the oxidation of elemental phosphorus to phosphorus oxyacids. The catalyst bed and a lift leg within the reactor and outside the catalyst bed are positioned within said reactor to provide access to the bottom of the lift leg by a phosphorus phase circulated from the bottom of the catalyst bed. The apparatus further comprises means for circulating aqueous liquid from an aqueous phase above the phosphorus phase in the reactor between an exit for the reactor in liquid flow communication with the upper end of the lift leg and a return to the reactor in liquid flow communication with the lower end of said lift leg within the phosphorus phase, whereby circulation of the aqueous liquid through the lift leg is effective to provide liquid/liquid contact between the phases and cause circulation of the phosphorus phase through the catalyst bed.

The invention is further directed to a process for the preparation of an oxyacid of phosphorus comprising oxidizing elemental phosphorus by catalytic reaction with water at a temperature below a threshold temperature at which the ratio of the sum of the rates of formation of P(I)+P(III) species to the rate of formation of P(V) species drops to 3.0 in a batch reaction system at 25% conversion of elemental phosphorus.

The invention is also directed to a process for the preparation of an oxyacid of phosphorus comprising catalytically oxidizing elemental phosphorus by reaction with water in a catalytic reaction zone comprising water, a phase containing elemental phosphorus and a catalyst for the reaction. Sonic and/or microwave energy is introduced into the reaction zone during the reaction.

Other objects and features will be in part apparent and in part pointed out hereinafter.

BRIEF DESCRIPTION OF THE DRAWINGS

FIG. 33 plots apparent point to point reaction rates vs. time for the reactions of Examples 115–117; and Corresponding reference characters indicate corresponding parts in the several views of the drawings.

DESCRIPTION OF THE PREFERRED EMBODIMENTS

Figure 1:
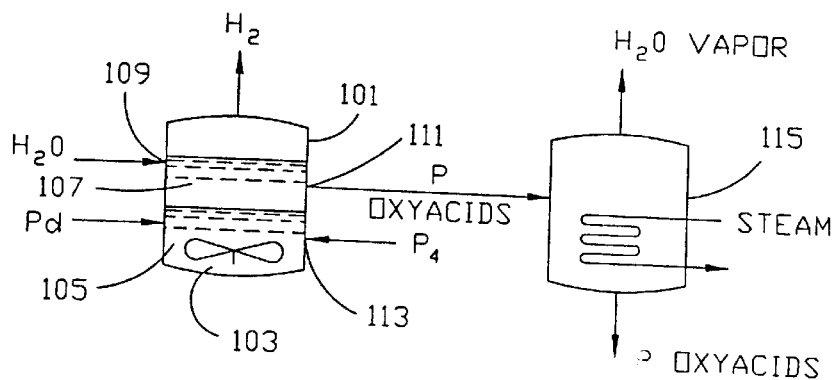
FIG. 1 is a schematic illustration of an apparatus of the invention and flowsheet for the process of the invention.

In accordance with the present invention, it has been discovered that elemental phosphorus, particularly tetraphosphorus, can be caused to react with water in the presence of a catalyst for the reaction to preferentially produce P(III) and P(I) oxyacids of phosphorus. Although catalytic oxidation of hypophosphorous acid (P(I)) to phosphorous acid (P(III)) was known to the art, it has now been found that elemental phosphorus may serve as the primary substrate for the preparation of hypophosphorous acid and/or phosphorous acid by oxidation with water in the presence of a catalyst. The reactions of the invention, and the further conversion of phosphorous acid to phosphoric, may be represented by the following equations:

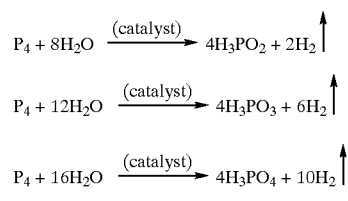

The reactions are understood to proceed essentially sequentially, i.e.:

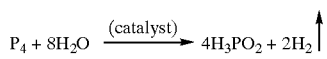

-continued

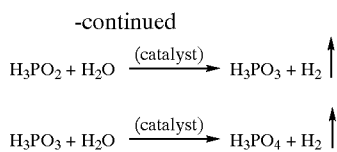

Some phosphine is also produced in the reaction, indicating that a disproportionation step may be involved in the reaction mechanism, i.e.:

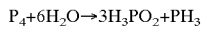

This is believed to be followed by catalytic oxidation of a significant portion of the phosphine to the P(I) acid:

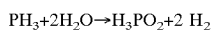

Whatever the exact mechanism, when the reaction is conducted under the preferred conditions as described hereinbelow the proportion of phosphine can be relatively small compared to the phosphine obtained in the known disproportionation obtained in an alkaline system without a catalyst.

In accordance with the process of the invention, elemental phosphorus, preferably tetraphosphorus, is contacted with water in the presence of a catalyst for the reaction. Preferably, the reaction is conducted under conditions selective to the preparation of P(III) oxyacid, P(I) oxyacid or mixtures thereof.

As used herein the term "P(I) species" includes any phosphorus compound, ion or moiety comprising phosphorus in an oxidation of state of +1, and "P(III) species" includes any such compound, ion or other moiety comprising phosphorus in an oxidation state of +3. P(I) and P(III) species produced in the catalytic reaction of the invention may include phosphorous acid, hypophosphorous acid and/or the conjugate bases thereof, i.e., $H_2PO_3^{-1}$ and $H_2PO_2^{-1}$, respectively, and/or the various further conjugates of these anions such as $HPO_3^{-2}$, $PO_3^{-3}$, and $HPO_2^{-2}$. Depending on the overall composition of the reaction mixture and conditions of the reaction, other P(I) and/or P(III) species may be present. For purposes of this disclosure, P(I) and P(III) oxyacids and conjugate bases, the further conjugates thereof, and mixtures of P(I) and P(III) oxyacids and/or any of the various conjugates, may be individually and collectively referred to herein as "lower phosphorus oxidation products."

Preferably, the reaction is conducted in a heterogeneous condensed phase reaction system, in which a condensed phase comprising elemental phosphorus, preferably tetraphosphorus, is contacted with a separate aqueous liquid phase. A heterogeneous reaction system is especially preferred for production of a reaction product mixture primarily comprising phosphorous acid ($H_3PO_3$), $H_2PO_3^{-1}$, $HPO_3^{-2}$, $PO_3^{-3}$, hypophosphorous acid ($H_3PO_2$), $H_2PO_2^{-1}$, and/or $HPO_2^{-2}$. In a heterogeneous system the elemental phosphorus may be dissolved in a substantially water-immiscible solvent, preferably an organic solvent such as benzene or toluene. Advantageously, tetraphosphorus is charged neat, either in molten or dispersed solid form. Alternatively, the reaction may be conducted in a homogeneous system comprising a water-soluble solvent for the elemental phosphorus. Suitable water-miscible solvents include lower alcohols ($C_1$ to $C_5$) and ionic liquids, i.e., salts that are liquids at the temperature of the reaction.

The ratio of water to tetraphosphorus in the reaction system is not generally critical for the reaction as such, but is necessarily controlled to provide a sufficient supply of phosphorus to produce phosphorus oxyacids at the concentration desired consistent with preserving the desired selectivity. In a heterogeneous reaction system, it is desirable to provide a sufficient interfacial area between the aqueous phase and the phase comprising tetraphosphorus so that the reaction rate is not limited by the mass transfer rate, and oxyacids are removed from the phosphorus phase at a rate sufficient to preserve selectivity. For convenience, the latter phase is sometimes referred to hereinafter as the "phosphorus phase," a term that should be understood to encompass either neat elemental phosphorus or a solution of elemental phosphorus in a substantially water-immiscible solvent. A sufficient interfacial area between the aqueous and phosphorus phases is provided by controlled agitation, and/or by various equipment arrangements as described hereinbelow. Oxidation of tetraphosphorus is believed to occur substantially in the phosphorus phase (as is indicated by release of hydrogen from that phase) by reaction of tetraphosphorus with water transferred from the aqueous phase to the phosphorus phase. Phosphorus oxyacids reaction products are transferred back across the interface to the aqueous phase.

A wide variety of catalysts are effective in the oxidation reaction of the invention. Generally preferred catalysts include, for example, Group IB metals (e.g., Cu, Ag, and Au), Group VIII metals (e.g., platinum-group metals, such as Pt and Pd), oxides of Group IB metals, oxides of Group VIII metals (e.g., oxides of platinum metals), salts of Group IB metals, salts of Group VIII metals (e.g., salts of platinum metals), phosphides of Group IB metals, and phosphides of Group VIII metals. catalysts include, for example, platinum metals, In certain embodiments of the invention, the catalyst is preferably a noble metal catalyst or mixture of noble metal catalysts. High selectivity has been achieved, for example, using a catalyst comprising palladium, and more preferably palladium black, at temperatures effective for selectivity of the oxidation to P(I) and P(III) in preference to P(V) species. Especially high selectivity may be achieved using catalysts having an active phase comprising copper, copper phosphide, copper oxide, a copper salt, such as copper chloride, copper sulfate, copper hypophosphite, copper phosphite, copper phosphate, or copper nitrate. Other particularly preferred catalysts comprise salts or coordination compounds of ruthenium and rhodium.

Optionally, the active catalyst may be supported on a carrier which extends the effective surface area of the active metal, and thus the availability of active sites. The use of various conventional catalyst supports may serve to extend the effective active phase surface area of the catalyst deposited on the typically high surface area of the support, and in some instances may also serve to prevent loss of surface area due to agglomeration.

Some dispersed noble metal catalysts have been observed to agglomerate during the reaction, resulting in loss of effective active surface area and reduced catalyst productivity. An inert support may further serve to prevent leaching of catalyst and loss of active catalyst in the aqueous product phase, though loss of catalyst is not a significant problem when a noble metal catalyst is used under the preferred reaction conditions as described hereinbelow. An exemplary supported catalyst is, for example, a Pd on carbon catalyst. Conventional 1% Pd/C, 3% Pd/C or 5% Pd/C catalysts may be suitable. Other suitable carriers may include alumina, silica, titania, zeolite, kieselguhr, etc. While a Pd catalyst is highly selective to P(III) oxyacid, other noble metal catalysts, and especially other platinum metal catalysts such as Pt, Ru or Rh may also be used. For example, conventional Pt/C catalysts are effective for the reaction.

Inert supports can also be useful in the case of Group IB and Group VIII catalysts, both to extend the effective surface area of the active catalyst phase, and to stabilize the catalyst and prevent leaching of the catalyst by products of the reaction. Group IB and Group VIII catalysts may be provided on the supports discussed above for platinum metal catalysts. To enhance adhesion of copper or other Group IB metal to a carbon support, it may be desirable to first apply a noble metal such as Pt or Pd to the support, then apply Cu or Ag over the Pt or Pd layer. Alternatively, a Group IB catalyst may be used on a suitable support such as a pyrophosphate salt, advantageously a pyrophosphate of titanium, hafnium or zirconium.

Despite the function that can be provided by a support, it has been discovered that a particularly preferred catalyst comprises an unsupported copper compound, most preferably a copper salt such as a copper halide or other salt of a mineral or other low molecular weight acid. In a heterogeneous liquid reaction system comprising an aqueous phase and a water-immiscible phase comprising elemental phosphorus, it is generally believed that the desired oxidation of elemental phosphorus to P(I) and P(III) species takes place primarily in the phase comprising phosphorus. Nonetheless it has been found that when the catalyst comprises water soluble copper compounds such as $CuCl_2 \cdot H_2O$, the cupric ion becomes incorporated into the phosphorus phase. Within the phosphorus phase, the cupric ion may react with elemental phosphorus to produce one or more copper phosphides which may afford the catalytic function. The oxidation state of cupric ion may be reduced to cuprous in the process, and even elemental Cu may be formed. In any event, the copper salt combines with elemental phosphorus and the phosphorus phase becomes ultimately dispersed in a granular, filterable form that exhibits the appearance of black sand. In introducing the copper catalyst into the reaction mixture, a copper salt is preferably first dissolved in a minimum amount of water, i.e., effective to produce and essentially saturated solution of the salt, and then added to the elemental phosphorus and mixed thoroughly therewith prior to mixing of the phosphorus phase with reaction water. Thereafter, the phosphorus phase containing the copper catalyst is mixed under agitation with an aqueous phase comprising the reaction water, resulting in the formation in the reaction vessel of a silvery (reflective) black pool of elemental phosphorus containing the catalyst beneath the aqueous phase. After some period of reaction, the silvery black pool breaks up and the catalyst and phosphorus phase disperse in the form of the filterable black sand referred to above. Without being committed to a particular theory, it may be suggested that the reduced form of copper present in this black sand may comprise cuprous salt, a copper phosphide, copper metal or both or some combination of two or all of these. As discussed hereinbelow, the dispersed catalyst particles or droplets appear to be coated with a film of elemental phosphorus, though in some instances the copper catalyst may be dispersed in a phosphorus droplet, and by the end of the reaction the particles may even have converted to a copper phosphide. At a given temperature, the rate of reaction in a heterogeneous water/phosphorus reactant system comprising a Cu catalyst is observed to be significantly higher before black sand is formed than it is thereafter. Without being held to a particular theory, it is believed that the transformation to black sand may involve solidification of the phosphorus phase, substantially increasing the resistance to mass transfer between aqueous and phosphorus phases. But for either a system which has been transformed to black sand or one which has not, it has unexpectedly been discovered such copper catalysts provided by introduction of copper salts exhibit an increase in reaction rate with temperature that is substantially in excess of the increase that would be predicted from the Arrhenius equation.

In accordance with the invention, it has been discovered that the reaction may be controlled to be highly selective for P(III) acid, and specifically to minimize formation of P(V) acid, by conducting the reaction in a heterogeneous reactant system and avoiding excessive reaction temperatures. In particular, it has been discovered that certain catalysts, e.g., a noble metal catalyst such as palladium, has a strongly preferential affinity for the phase comprising tetraphosphorus vs. the aqueous phase. Group IB catalysts such as copper, copper oxides and copper phosphide also exhibit an affinity for the phosphorus phase. As discussed hereinabove, even water soluble copper salts are apparently distributed preferentially to the phosphorus phase or are converted rapidly in situ to forms of copper that do. In accordance with the invention, the catalyst may be predominantly distributed to the phase comprising tetraphosphorus, and in fact substantially contained therein. Thus, it is believed that the active sites of such catalysts are preferentially in contact with the phosphorus phase and that the reaction preferentially occurs in the phosphorus phase. In fact, at relatively elevated reaction temperatures, e.g., above 90° C., it may be desirable to minimize contact between the aqueous phase and any catalyst sites that may be active for the conversion of P(III) to P(V) acid. Fortuitously, it appears that many preferred catalysts are soluble in the phosphorus phase and have a strong preferential affinity for the phosphorus phase, functioning in effect as homogeneous catalysts therein. Additionally, or alternatively, some catalysts may perhaps assume a form or configuration in the aqueous phase that is so different from the form that they assume in the phosphorus phase so that they simply present no observed activity for oxidation of P(III) to P(V). Thus, provided that the catalyst has adequate affinity for the phosphorus phase, preservation of selectivity may not require any special steps to prevent contact with the aqueous phase. On the other hand, for purposes of productivity, it may nonetheless be desirable to thoroughly integrate the catalyst into the phosphorus phase before contacting the phosphorus phase with the aqueous phase that supplies water for the reaction.

Heterogeneous catalysts, e.g., supported catalysts or particulate catalysts such as Pd black, are preferentially highly phosphilic so that they also become predominantly distributed to the phosphorus phase. In the case of at least some heterogeneous catalysts, it may be desirable to control process parameters, such as intensity of agitation as discussed hereinbelow, to limit contact between active catalyst sites and the aqueous phase.

As noted, Pd black has a strong affinity for the phosphorus phase, and has proven to be an effective catalyst for the reaction. It is not known whether Pd black is distributed as a particulate metal within the phosphorus phase, is amalgamated as a metal solute in the phosphate phase, or reacts with phosphorus to form a Pd phosphide. To the extent that it remains unreacted and undissolved, Pd catalyst may not be fully available for promoting the reaction between elemental phosphorus and water.

The apparent formation of a Cu phosphide, or at least the atomic distribution of Cu in the phosphorus phase, is believed to make a Cu catalyst derived from $CuCl_2 \cdot H_2O$ a particularly advantageous catalyst for the reaction. With respect to a heterogeneous water/elemental phosphorus system, Cu derived from $CuCl_2 \cdot H_2O$ forms in effect a homogeneous catalyst within the phosphorus phase, where the desired reaction(s) are believed to proceed. The fact that cupric chloride is quite water soluble does not detract either from its effectiveness as a catalyst or its selectivity to P(I) and P(III) vs. P(V) oxyacids.

Where the catalyst comprises a metal salt having an inorganic counterion, it is believed that the counterion ordinarily plays no role in the function of the catalyst other than whatever effect it may have on partition of the metal between the aqueous and phosphorus phases. However, counterions such as molybdate or permanganate that function as oxygen atom transfer agents may have a beneficial effect in substantially accelerating the catalytic reaction. In the absence of a catalyst, such agents have no material effect. For example, the presence of Na molybdate fails to promote any reaction between water and phosphorus at temperatures below 200° C. However, a Cu molybdate catalyst has been observed to afford substantial initial increases in reaction rate as compared to $CuCl_2$ or $CuSO_4$. During catalytic oxidation of phosphorus in the presence of Cu molybdate, the aqueous phase turns progressively blue, consistent with the types of species having oxide and hydroxide functionality that are generated from the partial reduction of $MoO_4^{-2}$. If it is presumed, e.g., that Cu phosphide is an active redox catalyst which is oxidized by reaction with water and reduced by reaction with elemental phosphorus to produce POx species, it is possible that molybdate may act as transfer agent aiding in the presumed slow reoxidation of Cu phosphide. Other oxygen transfer agents include dimethyl dioxirane, ethylene oxide, iodosylbenzene oxides, oxonium salts, porphyrins, ferricinium salts, permanganate salts, hypochlorite salts and tungstate salts.

Electron transfer agents are also believed to be effective in promoting the catalytic oxidation reaction of the invention. Among the useful electron transfer agents are pyridine, methyl viologen, 4,4'-bipyridine, 2,2'-bipyridine, quinoline, and diquaternary salt such as 1,1'-ethylene-2,2'-dipyridinium bromide. See Fields U.S. Pat. No. 5,072,033.

Among the preferred catalysts for the reaction are various organometallic coordination compounds, other coordination compounds, and other organometallic compounds. For example, coordination compounds of platinum metals such as Pd, Ru, Rh, and of other transition metals such as Ni, Cr, Co and Mn, as well as group IB precious metals such as Ag and Au, have proven effective in catalyzing the reactions of the invention. All provide reasonable selectivity to P(I)+P(III) oxyacids. Ni provides only about an 85–90% selectivity, but this may be quite satisfactory for applications such as the conversion of waste sources of elemental phosphorus. By comparison, Ru and Rh coordination compounds provide selectivities consistently in the range of 92–98% to P(I)+P(III). Interestingly, very little P(I) acid is produced in oxidations conducted in the presence of Ni catalysts. In the case of all these metals, selectivity is preserved even after the elemental phosphorus is reacted to extinction and the catalyst has become dispersed in the aqueous phase. It has been observed that, even during the course of the oxidation reaction, when a substantial phosphorus phase remains present, coordination compounds such as $RuCl_2(2,2'$-bipyridyl$)_2$ and $RuCl_2$ (dimethylsulfoxide$)_4$, yield water-soluble species, as evidenced by the aqueous layer turning a transparent red. However, this phenomenon is not associated with any significant increase in the formation P(V) species.

Inorganic Ni salts such as $NiCl_2.xH_2O$, are not readily soluble in an elemental phosphorus phase, and therefore not effective as oxidation catalysts. Oleophilic ligands of Ni and other coordination compounds are effective in enhancing solubility in the phosphorus phase and favoring distribution of the metal to that phase in preference to the aqueous phase. Thus, in selection of coordination catalysts, highly oleophilic ligands are generally preferred. For example, $NiCl_2(\phi_3P)_3$, bis(cyclopentadienyl) Ni and bis(cyclooctadienyl) Ni are quite soluble in the phosphorus phase, and serve as an effective oxidation catalyst. All of these are coordinated to the metal via a tetrahedral geometry, e.g., through the olefinic double bonds of the cycloolefins. It is noted that, to be effective, the ligands must be capable of supporting the metal center in the phosphorus phase under reaction conditions, not just during initial mixing. As an example, $NiCl_2$(1,2-dimethoxyethane) is very soluble in tetraphosphorus at a mixing temperature of 450 C; but at a reaction temperature of 90° C., the $NiCl_2$(1,2-dimethoxyethane)/$P_4$ mixture turns from yellow to black and then Ni metal begins to plate out on the sides of the reactor. Thus, the 1,2-dimethoxyethane ligand is not capable of supporting the metal complex under reaction conditions; and so it decomposes.

Other criteria also affect the preferred choice of ligand sets. Strongly binding ligands that do not readily dissociate can hinder catalytic activity by inhibiting access of tetraphosphorus to coordination sites on the metal. For example, the monodentate triphenylphosphine ligands of $NiCl_2(\phi_3P)_2$ can readily dissociate to open up reaction sites on the metal complex. However, the bidentate 1,2-bis(diphenylphosphino)ethane ligand of $NiCl_2$bis(diphenylphosphino)ethane is much less disposed to open a coordination site and the oxidation reaction is much slower with this catalyst. For Ni catalysts containing two cyclopentadienyl rings, one cyclopentadienyl ring is known to readily dissociate from the metal complex. Consistently with this characteristic, bis(cyclopentadienyl) Ni has been shown to catalyze relatively favorable rates of oxidation of elemental phosphorus to P(III) oxyacids. The presence of highly labile ligands has also been observed to result in an increase of reactivity with temperature that far exceeds the normal increase predicted by the Arrhenius equation. For example, in the case of $RhCl(\phi_3P)_3$, the kinetic rate constant for oxidation of elemental phosphorus to P(III) oxyacid increases tenfold between 90° and 110° C., rather than fourfold as would generally be expected.

Electron withdrawing ligands that retard oxidative addition may also slow catalytic activity. For example, in the case of Rh, Wilkinson's catalyst, $RhCl(\phi_3P)_3$, provides a conversion rate far higher than an otherwise similar catalyst, trans $RhCl(CO(\phi H_3)_2$, in which the electron withdrawing CO ligand is substituted for one of the triphenylphosphine ligands.

Catalysts vary in their selectivity to P(III) vs. P(I) reaction products. However, as described in detail hereinbelow, P(I) species such as hypophosphorous acid, $H_2PO_2^{-1}$ and $HPO_2^{-2}$ ion are readily converted to P(III) species such as phosphorous acid, $H_2PO_3^{-1}$, $HPO_3^{-2}$ and $PO_3^{-3}$, by aqueous phase reaction with water in the presence of a catalyst, typically a catalyst of the same character as that used for the oxidation of elemental phosphorus. Accordingly, a principal object of the present invention is realized by selectively oxidizing elemental phosphorus to produce lower phosphorus oxidation products in preference to P(V) species. Irrespective of the distribution of oxidation reaction products among P(I) and P(III) species, the catalyst and other conditions are preferably selected to maximize the molar ratio of the sum of the P(I) and P(III) concentrations to the P(V) concentration in the reaction mixture that is produced by oxidation of elemental phosphorus. It has been found, for example, that certain catalysts that are effective to produce an initial reaction mixture having a high [P(III)+P(I)]/P(V) ratio may yield a relatively low ratio of P(III)/P(I); but, as desired, the P(I) species is readily and selectively converted to P(III), producing an ultimate reaction product having a high phosphorous acid concentration and a high ratio of P(III)/P(V). Thus, ultimate P(III)/P(V) ratios greater than five, preferably greater than eight, more preferably greater than 19 are achieved in the process.

The preferred copper salt catalysts have been demonstrated to provide a high selectivity to P(I)+P(III) oxyacids under a wide range of temperature and agitation conditions, including the elevated temperatures, e.g. greater than about 100° C., more preferably between about 105° C. and about 180° C. at which the super-Arrhenius temperature response of the reaction constant provides especially high productivity.

It is generally preferred that any non-homogeneous catalyst for the phosphorus oxidation reaction should present an active phase B.E.T. surface area of at least about 5 $m^2/g$, typically between about 5 $m^2/g$ and 70 $m^2/g$. Preferably a platinum metal catalyst such as Pd black has a B.E.T. surface area of between about 30 and about 50 $m^2/g$, while a copper metal catalyst presents a B.E.T. surface area of between about 10 and about 60 $m^2/g$. High active phase surface areas may be effectively achieved by use of a support for the active phase. The oxidation process can be carried out over a fixed catalyst bed, over a fluidized bed, or with a catalyst slurried in a condensed phase reaction system. Using catalysts having the preferred active phase surface area, reaction temperature and agitation conditions may be selected to produce phosphorous acid at a rate of at least $1 \times 10^{-7}$ kg/hr-g catalyst.

In a slurry system, loading of a noble metal or other catalyst is typically between about 0.5 mole % and about 50 mole % noble metal, preferably about 1 mole % to about 15 mole %, more preferably about 1.5 mole % to about 12 mole %, based on P atoms present in the reaction system, especially where the catalyst is charged in metallic form, such as Pd black. Where the catalyst is extended by use of a carrier, lower loadings may be feasible. As the most effective loading may vary with the nature and form of the catalyst, the optimal commercial catalyst loadings should be determined by routine experimentation.

In a fixed or fluid bed reaction system, the catalyst mass defines a catalytic reaction zone in which the active phase surface area is preferably sufficient to produce a lower phosphorus oxidation product at a rate of at least 0.01 kg/hr, preferably at least about 10 kg/hr, more preferably at least about 50 kg/hr, per unit volume of said reaction zone as expressed in $m^3$. In a continuous fixed or fluidized bed reactor, the active catalytic surface area and reaction temperature are selected to produce P(I) and P(III) species at a combined productivity of at least about $1 \times 10^{-7}$ kg/hr-g catalyst, preferably at least about $1 \times 10^{-4}$ kg/hr-g catalyst, more preferably at least about $1 \times 10^{-3}$ kg/hr-g catalyst.

The reaction can proceed over a wide range of temperature, e.g., between about 100 and about 200° C. However, it has been determined that, at reasonable mass transfer rates between the liquid phases, the reaction is kinetics limited even in a heterogeneous reaction system; and it has further been found that for most catalysts other than Cu salts or coordination compounds, temperature has the expected exponential effect on kinetic rate constants. As noted, temperature has been observed to have a super-Arrhenius effect where some salts and coordination compounds are used. Accordingly, it is generally desirable to conduct the reaction at the maximum temperature consistent with adequate selectivity. Selectivity to P(I)+P(III) vs. P(v) acid has been observed to deteriorate moderately with temperatures above about 100°; but at temperatures significantly above 200° C. deterioration is progressive. At temperatures below 200° C., selectivity varies depending on the nature of the catalyst, and at least for some catalysts may depend on the extent of contact of active catalyst sites with the aqueous phase. Depending on the selection of catalyst and other conditions, the optimum temperature may vary. To maximize productivity, it is generally preferred that the reaction be conducted at a bulk fluid temperature near the threshold temperature, preferably 0.5° to 20° C., more preferably 2° to 10° C., below the threshold temperature, at which selectivity to [P(I)+P(III)] vs. P(V) begins sharply to deteriorate. While this threshold temperature varies with the nature of the catalyst as well as other reaction parameters, it may typically be defined as the temperature at which the marginal ratio of [P(I)+P(III)] formation to P(V) formation [d(i+iii)/dv] drops below 3.0 in a batch reaction system. Depending on the nature of the catalyst the selectivity deterioration threshold temperature may be, e.g., 195° C., 185° C., 175° C. or 150° C.

The optimal tradeoff between productivity and selectivity may vary depending on the purpose for which the product oxyacid is used. Since the freezing point of tetraphosphorus is about 45° C., reactions conducted below that temperature should be carried out in the presence of a solvent for tetraphosphorus.

Reaction is conducted most effectively under an inert or reducing atmosphere. For example, the reaction may be conducted under an argon or nitrogen atmosphere. Preferably, the aqueous phase of a heterogeneous reaction system, or the entire charge solution of a homogeneous reaction system, is purged with nitrogen, argon or other inert gas for removal of dissolved oxygen prior to the reaction.

Illustrated in FIG. 1 is a tank reactor 101 provided with agitation means such as a turbine agitator 103. Contained within the tank is a pool of liquid tetraphosphorus 105 and an aqueous liquid 107 above and in interfacial contact with the phosphorus phase. In accordance with the invention, it has been discovered that when a noble metal catalyst such as Pd black is added to the reactor and the contents of the reactor subjected to moderate agitation, the Pd black is progressively transferred to the tetraphosphorus phase. This effect can be observed visually. When Pd black is first added to a water and tetraphosphorus charge in the tank, the entire charge mixture becomes black and opaque. However, as moderate agitation is applied, the aqueous phase gradually clarifies until it becomes water white, while the tetraphosphorus phase remains black or silvery black. At any temperature at which tetraphosphorus remains liquid, oxidation of tetraphosphorus proceeds, and as long as there is a substantial fraction of catalyst in the aqueous phase, the oxidation products include a substantial component of phosphoric acid; in fact the (P(V)) acid is the dominant product. However, once the catalyst has become predominantly distributed to the tetraphosphorus phase, the reaction continues with a high selectivity to phosphorous acid. Because the distribution of Pd black or Group IB metal or compound to the tetraphosphorus phase can proceed much more rapidly than any of the oxidation reactions, high overall selectivity can be realized in a batch reactor initially charged and operated as described.

Overall selectivity to phosphorous acid can be further enhanced by operating the stirred tank reactor on a continuous or semi-continuous basis, or semibatch. In continuous operation, water is continuously or intermittently supplied via a water inlet 109, product oxyacid solution is continuously withdrawn via a product exit 111, and tetraphosphorus is continuously or intermittently supplied via a phosphorus inlet 113. Although the phosphorus inlet as shown is located below the phase interface, phosphorus can be introduced at any point in the reactor and will distribute to the phase comprising tetraphosphorus. In semicontinuous operation, the aqueous phase flows continuously or intermittently throughout the reaction zone, but phosphorus is charged or replenished on a batch basis. In a semibatch operation, a charge of tetraphosphorus in excess of that required for a single batch may be initially introduced into the reactor together with catalyst in a concentration sufficient for the reaction, and a succession of oxyacid batches produced from successive charges of water to the reactor. Oxyacid of the desired concentration may be produced by controlling the residence time of a continuous or semicontinuous operation, or the cycle of a batch or semibatch operation. Alternatively, dilute acid withdrawn through exit 111 may be concentrated in an evaporator 115.

To minimize conversion of hypophosphorous and phosphorous acids to phosphoric acid, the nature and extent of agitation are controlled at an intensity sufficient to promote mass transfer between the phases but preferably low enough to avoid excessive contact of active catalyst sites with the aqueous phase. Below a moderate threshold agitation level, the reaction rate is limited by mass transfer of water for the reaction from the aqueous phase to the phosphorus phase, and phosphorus oxyacid products from the phosphorus phase to the aqueous phase. However, above the threshold, the reaction rate no longer depends on mass transfer, but is limited by kinetics of the reactions. Once the kinetics limiting condition has been realized, further increases in agitation do not appear to serve a purpose; and at least for some heterogeneous catalysts excessive agitation potentially exposes the aqueous phase to contact with active catalyst sites, which may be expected to result in decreases selectivity to phosphorous acid. However, the range of acceptable agitation intensity appears to be quite broad. Thus, in the case of a Pd black catalyst, selectivity does not appreciably suffer even when the phosphorus phase is reduced to a fine dispersion within a continuous aqueous phase, indicating perhaps that the individual Pd catalyst particles remain encapsulated within a phosphorus phase envelope. In any event, within a relatively broad agitation range above the threshold level, the reaction rate and selectivity are substantially unaffected by agitation. In this range, the reaction rate exhibits zero order or pseudo zero order behavior, perhaps indicating reaction within a water-saturated phosphorus phase, but responds to temperature and catalyst loading in an essentially classical fashion. It has been discovered that, over a relatively wide range of agitation intensity, a reaction product may be produced in which the molar ratio of phosphorous acid to phosphoric acid is at least about 0.4, with ratios of 5 to about 19 being readily achieved. Thus, phosphorous acid may be produced in concentrations above 5% by weight, preferably between about 20% and about 70% by weight, while maintaining sufficient selectivity to produce P oxyacids in a P(III)/P(V) ratio of at least about 8, and having a phosphoric acid content no greater than about 15% by weight.

Where a copper catalyst is used, selectivity to P(I) and P(III) acids is preserved at a high level even where the agitation is sufficiently intense to disperse granular particles or droplets of water-immiscible material in the aqueous phase. The droplets are black in appearance, and may be thought to comprise active catalyst sites encapsulated or dispersed in a film or droplet of elemental phosphorus. In some instances, copper may be dispersed in the aqueous phase as a copper phosphide or phosphorus/copper phosphide amalgam. As the reaction progresses, they are transformed to the "black sand" discussed hereinabove. In any event, it appears that the reactive sites of the catalyst are segregated from the aqueous phase by a film of elemental phosphorus or other water-immiscible material so that conversion to phosphoric acid remains inhibited. Moreover, where a copper or other Group IB catalyst is used, selectivity to P(I) and P(III) acids is typically greater than 90%, more typically greater than 95%, and usually greater than 98%.

Further in accordance with the invention, it has been discovered that substantial enhancement of the rate of the catalytic oxidation reaction can be realized by transmission of sonic energy into a reaction zone comprising an aqueous phase, a phase comprising elemental phosphorus, and a catalyst for the reaction. It has been found that sonication at a frequency between about 10 kHz and about 1 MHz and an intensity of between about 0.1 and about 15 watts/cm$^3$ typically enhances the reaction rate by a factor of at least about 2, preferably at least about 5, as compared to the reaction rate under otherwise identical conditions of aqueous phase composition, phosphorus phase composition, catalyst activity and temperature. For example, the reaction rate in a sonicated reaction mixture at 60° C. has been found equivalent to the reaction rate in an unsonicated mixture at 90° C. The effect of sonication is particularly advantageous in the preferred embodiment of the invention in which the catalyst is contained within the phosphorus phase, or at least the active catalyst sites are separated from the aqueous phase by a film of the phase comprising elemental phosphorus. Although bulk agitation does not significantly affect reaction rate once a relatively modest level of agitation has been realized, sonication has been found to materially increase reaction rate at essentially any bulk agitation intensity sufficient for adequate supply of water to the phosphorus phase and removal of phosphorus oxidation products therefrom. While the instant invention is not limited to any particular theory, it would appear that impingement of sonic waves on the interface between the catalyst and phosphorus phase may enhance diffusivity of water to the reaction site and phosphorus oxidation products away from the reaction site, and/or that the film coefficient for mass transfer between the phosphorus phase and the active sites is in some other way promoted by introduction of energy at the aforesaid interface, perhaps by generation of microcavities in the film at the catalyst interface. It has been observed that sonication alters the appearance of the reaction mixture, converting it to an opaque liquid mass having the appearance of a "milk shake," though this is not believed to destroy the film of elemental phosphorus coating the active catalyst sites of a phosphophilic catalyst.

Sonication may also materially increase reactivity at the catalyst site by creating local high temperature, generating free radicals, or otherwise promoting the activity of the catalyst. Accordingly, it is believed that a significant rate enhancement is provided by introduction of energy in any form at that interface, a phenomenon achievable by introduction into the reaction zone of energy in a form which is transmissible through the aqueous and phosphorus phases without substantial dissipation, but is absorbable at the interface to enhance exchange of water and reaction products, and/or to enhance the reactivity at the catalyst site. Thus, for example, rate enhancement may be achieved by introduction of microwave energy into the reaction zone rather than (or in addition to) sonic energy.

While sonication or microwave transmission into the reaction mixture may involve substantial instantaneous energy consumption, it may be feasible to obtain substantial enhancement of reaction rate with lesser energy consumption by pulsing the waves. Pulsing at a substantial frequency may maintain the desired effect at the catalyst/phosphorus interface, or other advantageous effect on reactivity, while introducing energy only during a modest net fraction of the reaction cycle.

Sonication has been observed to have a greater effect on the rate constant for conversion of elemental phosphorus to P(I) acid than on the rate of conversion of P(I) to P(III) acid. Thus, where phosphorous acid is the desired ultimate product, it may be desirable to use sonication in the initial reaction zone in a process of the type illustrated, e.g., in FIG. 3.

With most catalysts, selectivity declines moderately with increased temperature, but remains generally favorable throughout the reaction temperature range discussed hereinabove. In the case of heterogeneous catalysts, e.g., a supported catalyst or a particulate catalyst such as Pd black, the agitation may be controlled at a rate which provides the maximum rate of mass transfer that can be realized without substantial entrainment of catalyst in the aqueous phase. For example, sufficient transfer of water to the phosphorus phase and phosphorus oxyacid reaction product to the aqueous phase can be realized by a level of agitation which preserves a pool of molten tetraphosphorus, or other heavier-than-water liquid phase containing tetraphosphorus at the bottom of a tank reactor, while continually breaking globules of the phosphorus phase off the liquid pool. Formed globules continually remerge with the liquid pool as further globules break off.

For heterogeneous catalysts, contact between active catalyst sites and the aqueous phase is preferably limited so that the rate of oxidation in the phosphorus phase (expressed as moles of reaction product per unit time) is at least ten times the rate of oxidation of phosphorus oxyacids in the aqueous phase. For example, in the case of Pd black catalyst, the noble metal content of the aqueous phase is reduced to and maintained at a concentration of not greater than about 1% by weight, more preferably no greater than about 200 ppm, most preferably not greater than about 0.1 ppm. Concentrations well below 200 ppm are readily achieved under moderate to vigorous agitation, since the Pd black is observed to have a strong preferential affinity for the phosphorus phase. Under the preferred conditions of moderate temperature and limited contact between active catalyst sites and the aqueous phase, the phosphorus oxyacid fraction of the oxidation reaction product contains at least about 5 moles phosphorous (P(III)) acid per mole of phosphoric (P(V)) acid. Under certain combinations of catalyst and temperature which yield high initial fractions of P(I) acid, the P(III)/P(V) ratio may be less than five, but the molar ratio of the sum of P(I) acid and P(III) acid concentrations to the P(V) acid concentration is controlled at values above five, which may provide equivalent ultimate selectivity to P(III) after catalytic conversion of P(I) to P(III) acid as described elsewhere herein. P(III) to P(V) molar ratios (or [P(I)+P(III)]/P(V) molar ratios) greater than about 8, in fact about 9, are quite readily achieved.

In contrast to the previously known water oxidation processes for producing phosphoric acid, which may yield relative high proportions of P(I) and/or P(III) by-product only at the inception of the reaction, the process of this invention preserve high selectivity to phosphorous acid, or to phosphorous and hypophosphorous acid, at materially significant conversion, i.e., at conversions sufficient to provide a commercial route to a product of high phosphorous acid content, e.g., at phosphorus conversions greater than 2%, preferably greater than 5%, more preferably greater than 15% or 25%. In fact, under the preferred conditions as described herein, the above noted selectivities to P(III) or P(I)+P(III) acids is achievable at conversions approaching 100%. In a semibatch system as described above, conversion may be deemed the proportionate consumption of the phosphorus pool in each batch of phosphorus oxyacid solution produced in the phosphorus phase. As applied to a standard batch or continuous mode of operation, the term conversion has its standard meaning.

Various methods may be employed to promote transfer of catalyst from the aqueous phase to the phase comprising tetraphosphorus, providing a heterogeneous water/phosphorus reactant system in which catalyst is predominantly distributed to the phosphorus phase. As noted above, the desired redistribution may be accomplished by agitating a charge mixture of molten tetraphosphorus, water and catalyst at a temperature above the melting point of tetraphosphorus but low enough to avoid significant oxidation of phosphorous acid to phosphoric acid during the redistribution operation. Generally satisfactory redistribution may be accomplished at temperatures up to about 90° C. Establishing the desired distribution may require a relatively extended period of agitation, for example 24 hours or more. Programmed heating of the charge mixture during catalyst redistribution may shorten the time requirement without significant loss in phosphorous acid yield. Whatever the precise schedule, the temperature is preferably maintained below about 75° C., more preferably below about 60° C. during the redistribution phase.

Once redistribution is accomplished, repetitive batch reactions or continuous reaction may proceed with periodic or continuous replenishment of tetraphosphorus, and without interruption for further redistribution of catalyst. In a batch system, replenishment should occur prior to exhaustion of molten phosphorus, and prior to the time that phosphorus inventory has been reduced to a level at which active catalyst sites become exposed to the aqueous phase. Interruption of subsequent operations for catalyst distribution is required only as catalyst activity declines to the point that catalyst replacement or addition becomes necessary.

In a further preferred embodiment of the invention, a premixture may be prepared by mixing the catalyst with molten tetraphosphorus, or a solution of tetraphosphorus in a substantially water-immiscible solvent. The premixture is thereafter contacted with an aqueous liquid to carry out the oxidation reaction. The premixture can be readily formed in a stirred tank reactor of the type illustrated in FIG. 1, preferably under an inert atmosphere. After the catalyst has been substantially taken up by molten phosphorus (or solution of tetraphosphorus in an organic solvent), water is added and the reaction carried out under moderate agitation as discussed above. For certain catalysts, e.g., $CuCl_2 \cdot 2H_2O$, it has been found important to premix the catalyst with the phosphorus phase before contacting the phosphorus phase with the aqueous reactant. A concentrated solution of the salt may be mixed with the catalyst, which is assimilated by the phosphorus phase, the aqueous phase essentially disappearing. If the catalyst is first dissolved in the bulk aqueous reactant phase, redistribution is less effective, and reaction rates are at least initially very slow. Preferably, the premixture is heated to a temperature of between the melting point of tetraphosphorus and about 150° C. under an inert atmosphere.

Mixtures comprising tetraphosphorus and a catalyst effective for the catalytic oxidation of tetraphosphorus by reaction with water are useful compositions of matter. The composition typically comprises between about 0.5 and about 50 mole % catalyst based on phosphorus atoms in $P_4$. The catalyst is preferably a Group IB metal catalyst or a non-Group-IB noble metal catalyst, more preferably Cu, Ag, Pd, Pt or Rh, most preferably Cu or Pd. The mixture preferably consists essentially of a mixture of the catalyst and tetraphosphorus, but may also optionally comprise a solvent for the tetraphosphorus. As discussed hereinbelow, the catalyst may be in a reduced state.

Figure 2:
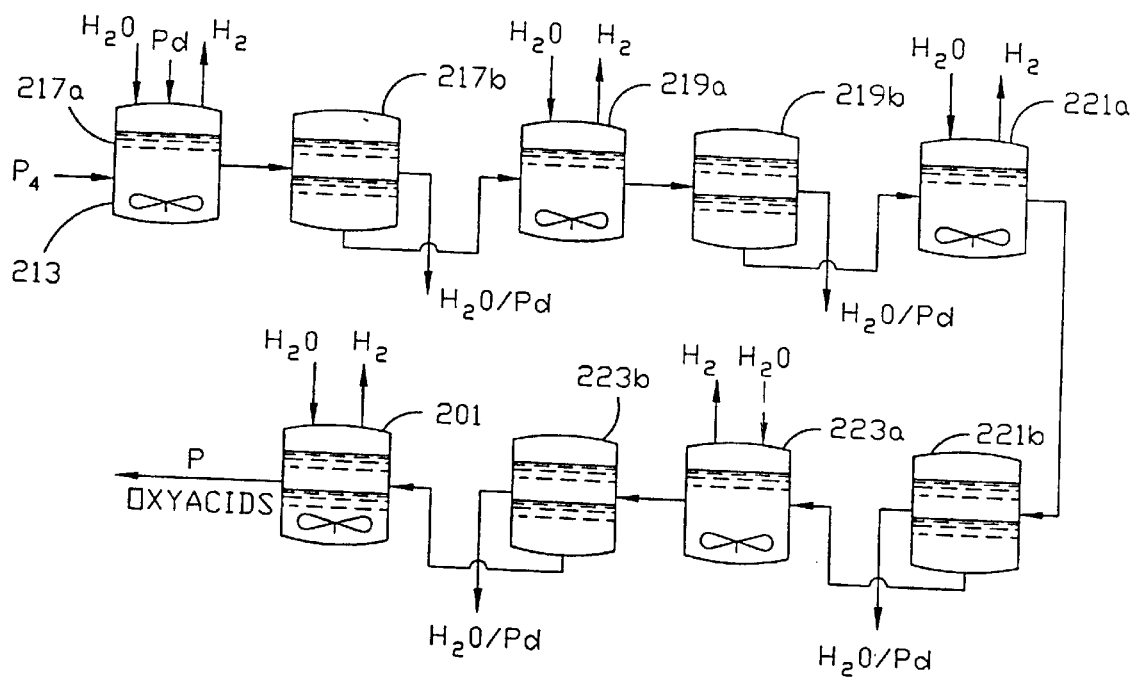
FIGS. 2 through 10 are schematic illustrations of alternative embodiments of apparatus of the invention and flowsheets for the process.
Figure 3:
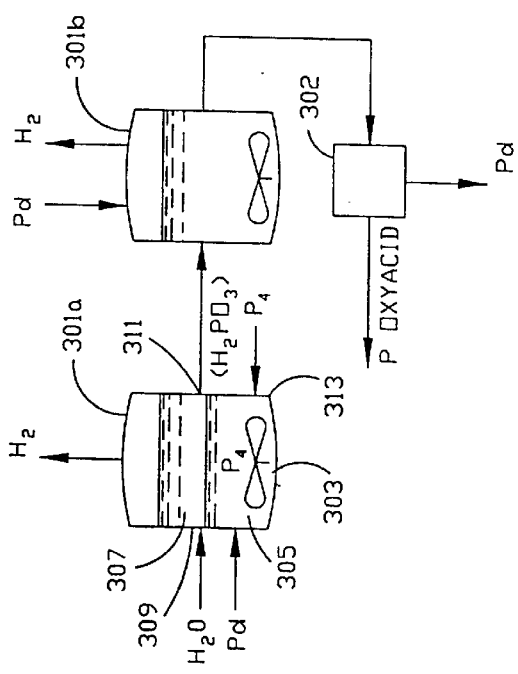

In a further embodiment of the invention, a water phase replacement wash operation may be conducted to purge residual solid phase catalyst from the aqueous phase in contact with the tetraphosphorus phase. In this embodiment, an initial precursor mixture is prepared comprising water, catalyst, and a phase comprising tetraphosphorus. The precursor mixture may be subjected to agitation. The liquid phases of the initial precursor mixture are then separated, thereby removing whatever noble metal or other solid phase catalyst has become distributed to the aqueous phase. Thereafter, the water-immiscible liquid phase (phosphorus phase) is contacted with an additional volume of water to provide a heterogeneous reaction system in which the selective oxidation reaction is carried out. Optionally, the water displacement wash operation is conducted in two or more successive stages. After the first separation of an aqueous wash mixture containing catalyst, the water-immiscible phosphorus phase is mixed with fresh aqueous liquid to provide a second precursor mixture which is preferably subjected to agitation for a brief time, after which the liquid phases of the second precursor mixture are separated for further removal of any catalyst distributed to that phase. As illustrated in FIG. 2, catalyst removal can be conducted in a series of purging stages 217, 219, 221 and 223, each comprising a washer/mixer 217a, 219a, 221a and 223a, and a separator 217b, 219b, 221b and 223b, respectively. A series of precursor mixtures is prepared, each of which is withdrawn from the mixer of a purging stage and introduced into the separator thereof. In each separator, the liquid phases are separated for removal of catalyst distributed to the aqueous phase. The liquid tetraphosphorus phase from each of purging stages 217, 219 and 221 is introduced into the mixer of the next successive purging stage, i.e., and the liquid tetraphosphorus from stage 223 is introduced into reactor 201 where it is mixed with an additional volume of water to provide the heterogeneous reaction mixture for selective oxidation of $P_4$ to P(III) oxyacid. By this washing scheme, the concentration of catalyst in contact with the aqueous phase may be reduced to a sufficiently low level so that the molar ratio of P(III) acid to P(V) acid in the ultimate oxidation reaction product is at least about 5, more typically at least about 8, and feasibly at least about 9.

Where the object is to obtain maximum yield of P(III) acid, it may be desirable to carry out the process in two reaction stages as shown in FIG. 3. In primary stage 301a, the reaction is conducted under conditions effective for oxidation of $P_4$, but with limited conversion of P(I) acid to higher acids. A crude reaction product withdrawn from reactor 301a may contain a significant fraction of hypophosphorous acid, e.g., at least about 1 mole %, more typically about 10 to about 30 mole %, based on total oxyacid content. The crude reaction product is contacted in a finishing reactor 301b, at a temperature of between 30° and about 120° C., with a catalyst which is effective for conversion of P(I) to P(III) acid without significant conversion of P(III) acid to P(V) acid.

Various catalysts are effective for this reaction, including noble metals such as Pd, Pt or Rh, other metal catalyst such as Ni, Co or Cu, or carbonaceous catalyst such as graphite. As necessary, catalyst may be removed from the finished reaction product in a filter 302, and may be recycled to either reactor 301a or 301b. Alternatively, the catalyst in reactor 301b may be in a fixed catalyst bed or other immobilized form, in which event no separate filtration step is required. The catalyst used in reactor 301b may be the same as that used in reactor 301a, but not necessarily so.

By limiting the conversion in reactor 301a, a crude reaction product is obtained in which the molar ratio of the sum of the phosphorous acid content and hypophosphorous acid content to the phosphoric acid content is at least about 5, more typically between about 8 and about 50. Conversion of hypophosphorous to phosphorous acid in finishing reactor 301b produces a final reaction product containing a ratio of phosphorous acid to phosphoric acid of at least about 5, with a ratio of between about 8 and about 50 being readily achievable. The molar ratio of hypophosphorous to phosphorous acid in the final reaction product is not greater than about 0.2. Preferably, the P(I)/P(III) ratio is no greater than about 5; a ratio between 0.01 and about 0.02 can be realized without difficulty.

A noble metal or other catalyst may optionally be reduced prior to the oxidation reaction. Typically, a noble metal catalyst comprises metal oxides. A carrier such as carbon may also become oxygenated. Optionally, such catalyst is reduced by contact with hydrogen. If intimate contact is achieved, the reduction may be effected at moderate temperatures and pressures. For example, the catalyst may be reduced by contact with a methanol or aqueous solution of hydrogen.

Because hydrogen is generated in the reactions by which $P_4$ is converted to oxyacids, in situ reduction of catalyst is inherently realized as the reaction proceeds. Alternatively, the catalyst may be reduced before any material oxidation of $P_4$ has occurred. In the preferred embodiment in which catalyst is premixed with a phosphorus phase, the catalyst is reduced by exposure to $P_4$, preferably at a temperature of at least the melting point of tetraphosphorus for at least about 1 minute. As noted hereinabove, where a water-soluble catalyst such as, e.g., $CuCl_2$ is used, more intimate mixing and effective reduction is realized by first dissolving the catalyst in a minimum amount of water, i.e., to prepare a substantially saturated aqueous solution thereof, and thereafter mixing this solution with the molten tetraphosphorus.

Figure 4:
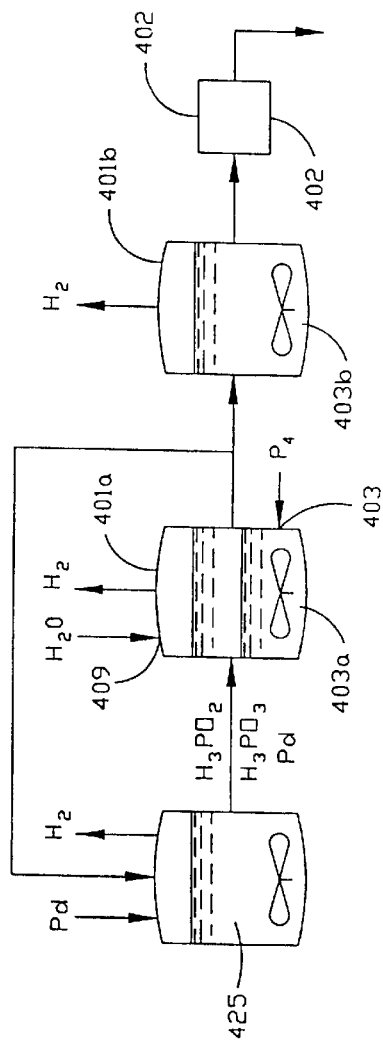

In certain embodiments of the inventions, the catalyst is reduced by contact with hydrogen generated in the formation of phosphorus oxyacids. As illustrated in FIG. 4, the oxidation of $P_4$ is conducted in two or more oxidation reactors arranged in series, shown in the drawing as 401a and 401b, operated generally in the manner described above for 301a and 301b of FIG. 3, and a fraction of the aqueous phase from reactor 401a containing hypophosphorous acid is recycled to a catalyst conditioning tank 425 comprising a pretreatment reaction zone. The catalyst may be dispersed in an aqueous medium comprising the recycled aqueous phase. Contact of catalyst with recycled hypophosphorous acid results in oxidative conversion of hypophosphorous acid to phosphorous acid, generating hydrogen at the catalyst surface in a manner effective for reduction of the catalyst. Only a limited fraction of the aqueous solution produced in reactor 401a need be recycled to conditioning tank 425 for reduction of catalyst in the pretreatment zone, and by controlling the temperature of pretreatment below about 85° C., conversion of any significant portion of the recycled hypophosphorous acid to phosphoric acid is avoided. Further catalytic oxidation of hypophosphorous acid to phosphorous acid is effected in reactor 401*b* in the absence of $P_4$ under conditions which prevent substantial conversion of phosphorous to phosphoric acid, e.g., by reaction at a temperature of between the melting point of $P_4$ and about 120° C.

Figure 6:
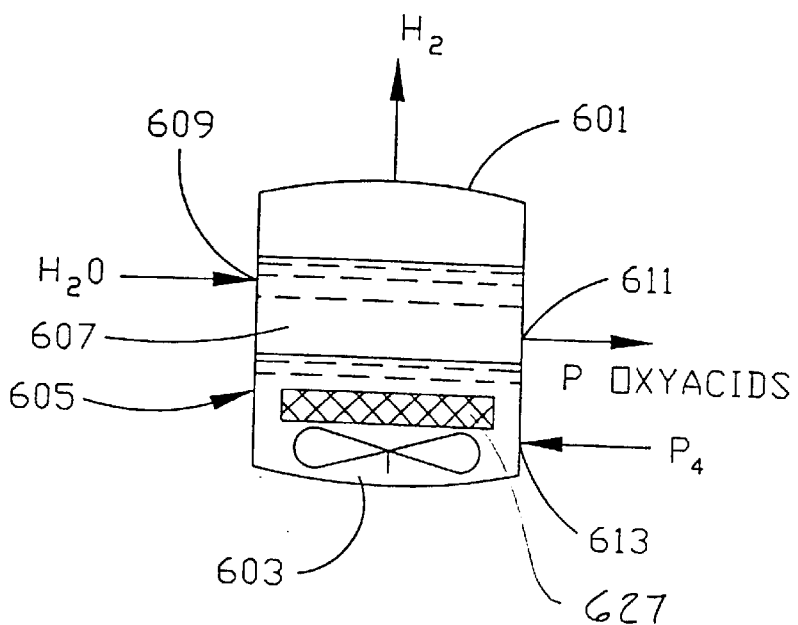

Further in accordance with the invention, various heterogeneous reaction schemes have been developed in which the catalyst is positioned in the phosphorus phase remote from the interface of the aqueous phase and the phase comprising tetraphosphorus, so that contact of the catalyst with the aqueous phase is positively prevented. FIG. 6 illustrates an apparatus comprising a reactor 601 having a bed of noble metal or other catalyst for the reaction in a container vessel 627 located in the lower portion of the reactor. When the reactor has been charged, vessel 627 is disposed within a body of liquid comprising tetraphosphorus spaced below the interface between the phosphorus phase and the aqueous phase. The container comprises walls effective to prevent egress of catalyst therefrom but permeable to the phosphorus phase. The region within the reactor around the liquid/liquid interface comprises a zone within which the phosphorus phase is contacted with the aqueous phase for transfer of water from the aqueous phase to the phosphorus phase and oxyacid reaction product from the phosphorus phase to the aqueous phase. The reaction system is agitated to promote mass transfer between the liquid phases and contact of water transferred to the phosphorus phase with catalyst within container 627 wherein the oxidation reaction proceeds. If the phosphorus phase comprises a solution of tetraphosphorus in a low density water-immiscible solvent, catalyst container 627 may be spaced above rather than below the liquid/liquid contact zone.

Figure 7:
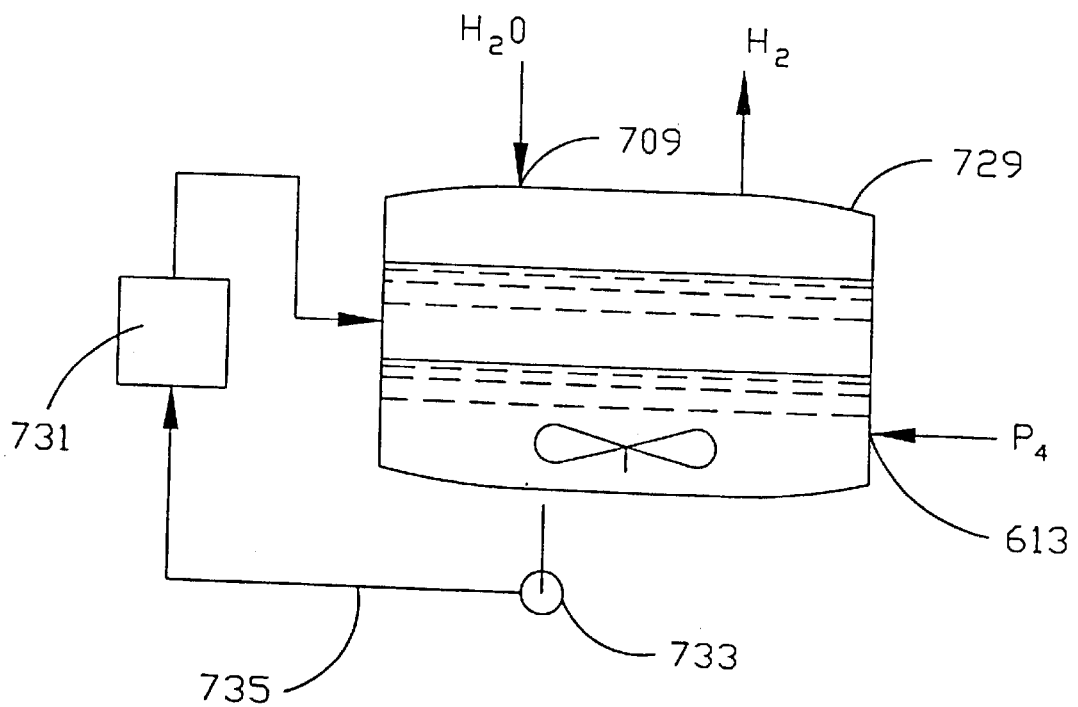
Figure 8:
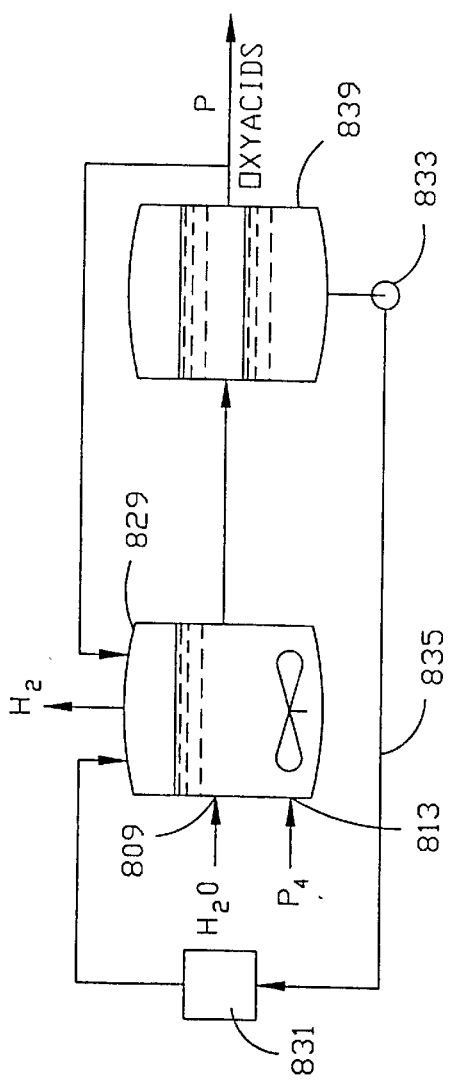

FIG. 7 illustrates an apparatus comprising a reservoir 729 comprising a liquid/liquid contact zone in which the phase comprising tetraphosphorus is contacted with an aqueous liquid. Mass transfer between the liquid phases is promoted by agitation means within the reservoir. A catalyst bed 731 comprising a noble metal or other catalyst for the reaction is positioned remotely from the reservoir. Means for circulating the phosphorus phase between the reservoir and the catalyst bed comprises a pump 733 and circulating line 735. Agitation in the liquid/liquid contact zone is moderate, allowing for separation of the phases and circulation of a phosphorus phase containing a minimum of entrained aqueous phase, but sufficient to promote extraction of phosphorus oxyacids from the phosphorus phase and transfer of water for the reaction into the phosphorus phase. In a modification of the system of FIG. 7, as illustrated in FIG. 8, vigorous agitation is imposed in the liquid/liquid contact zone of reservoir 829, producing an intimate liquid/liquid mixture or dispersion which is transferred to a vessel 839 comprising a zone within which the aqueous and phosphorus phases are allowed to separate. Settled phosphorus phase is circulated through a remote catalyst bed 831 via a circulating pump 833. The aqueous phase from separator 839 is also circulated back to reservoir 829. When sufficient conversion has been obtained, the aqueous phase in the separator comprises the phosphorus oxyacid reaction product, which can be transferred forward (or in a continuous system a fraction of the aqueous stream exiting the separator can be taken off as product once the desired steady state conditions have been realized). It may be advantageous to operate the depicted system at relatively low conversions of P(I) to P(III) and complete the latter conversion in a separate finishing reactor as illustrated in FIG. 3.

Figure 24:
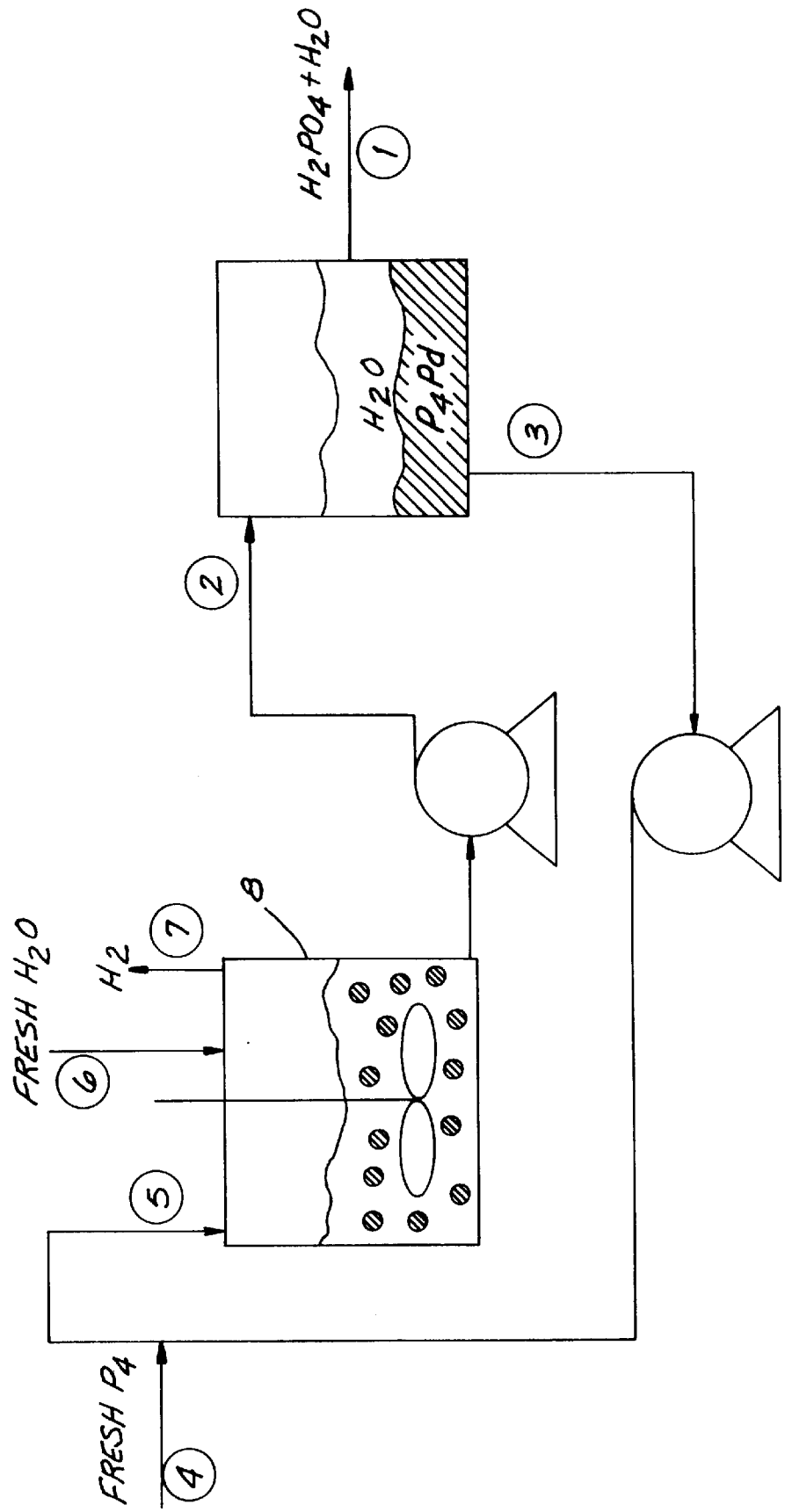
FIG. 24 is a process flowsheet similar to FIG. 8, but with the catalyst dispersed in the phosphorus phase rather than contained in a fixed bed.
Figure 25:
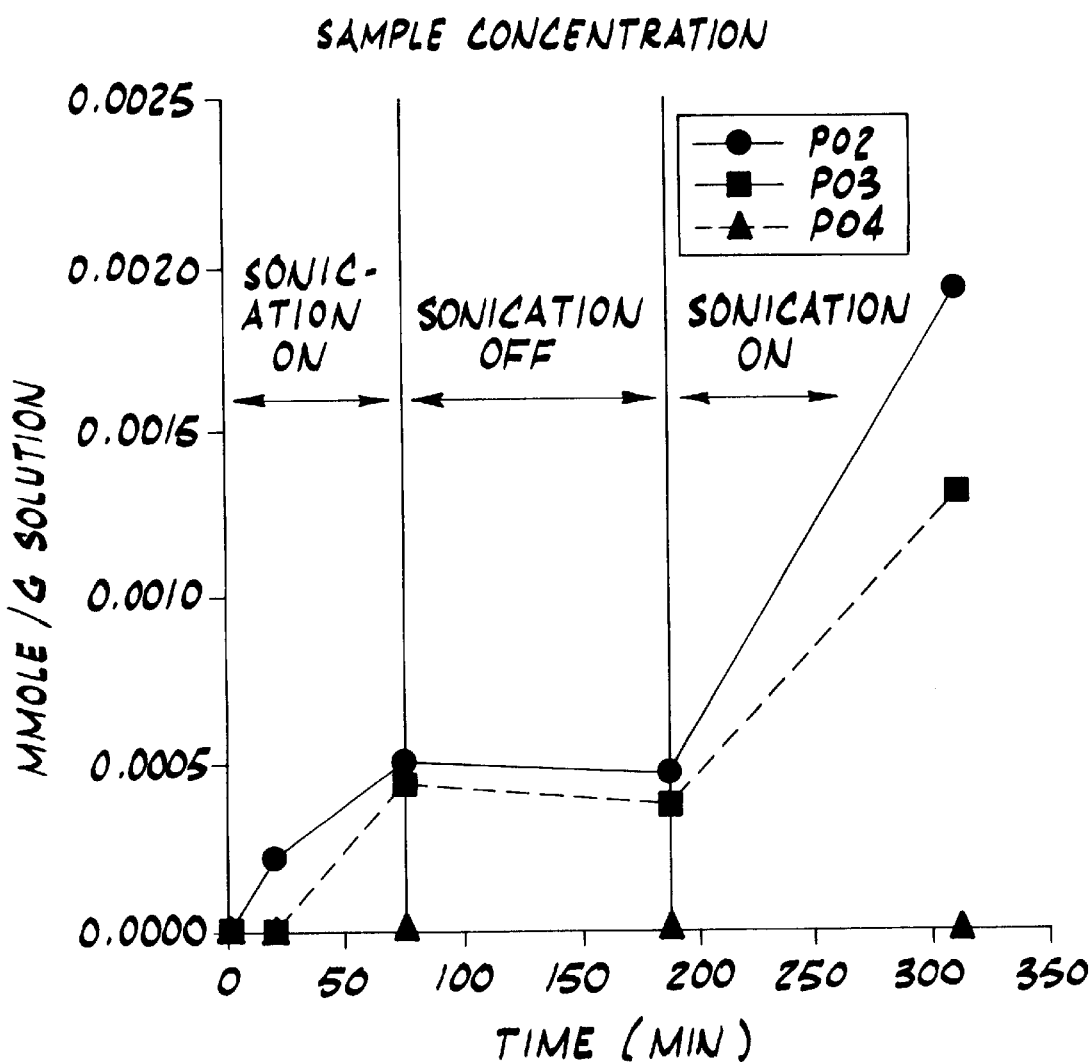
FIG. 25 is a plot of hypophosphorous acid, phosphorous acid and phosphoric acid concentrations vs. time in the sonicated reaction system of Example 41.
Figure 26:
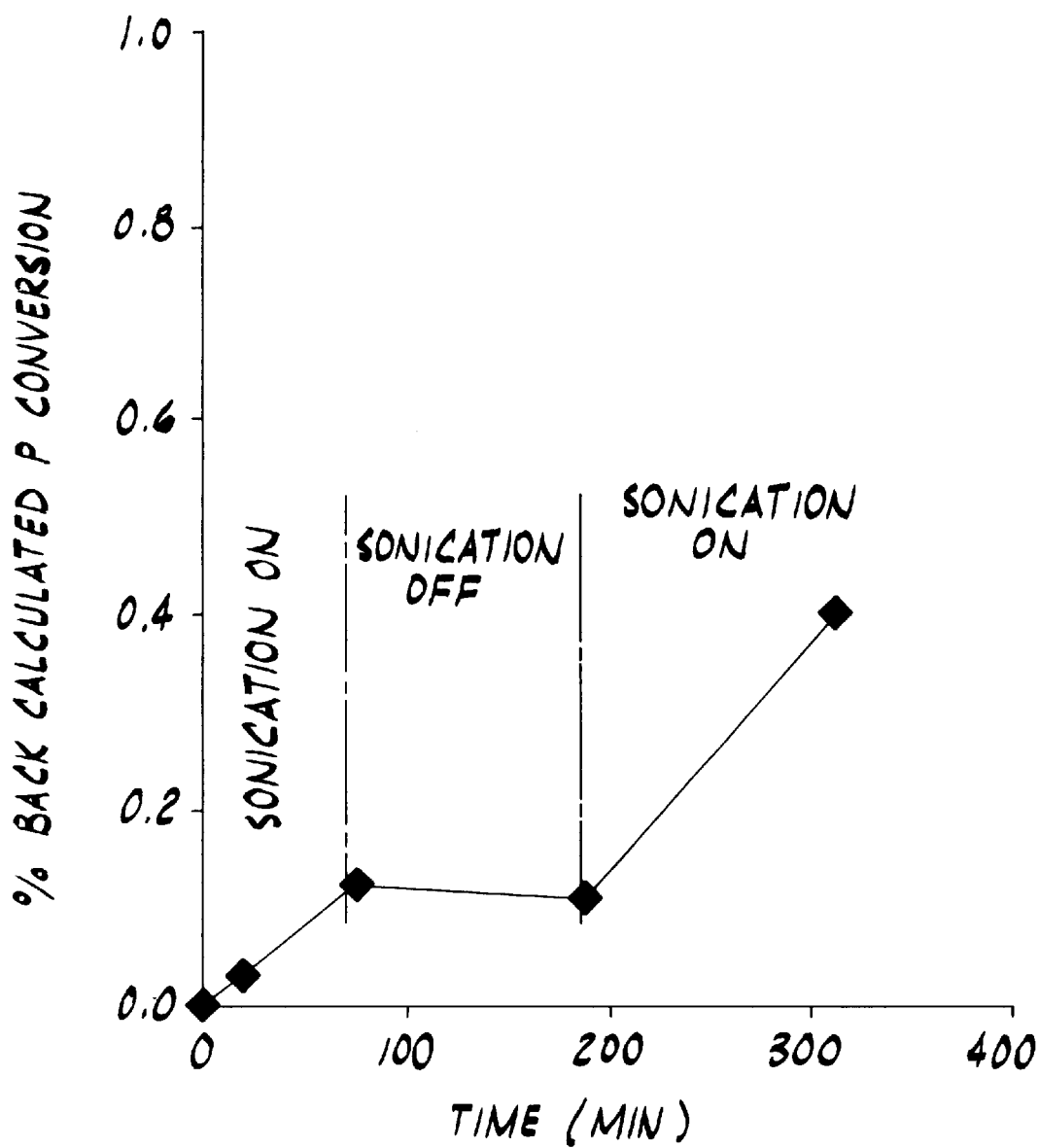
FIG. 26 is a plot of back calculated phosphorus conversion vs. time in the reaction system of Example 41.
Figure 27:
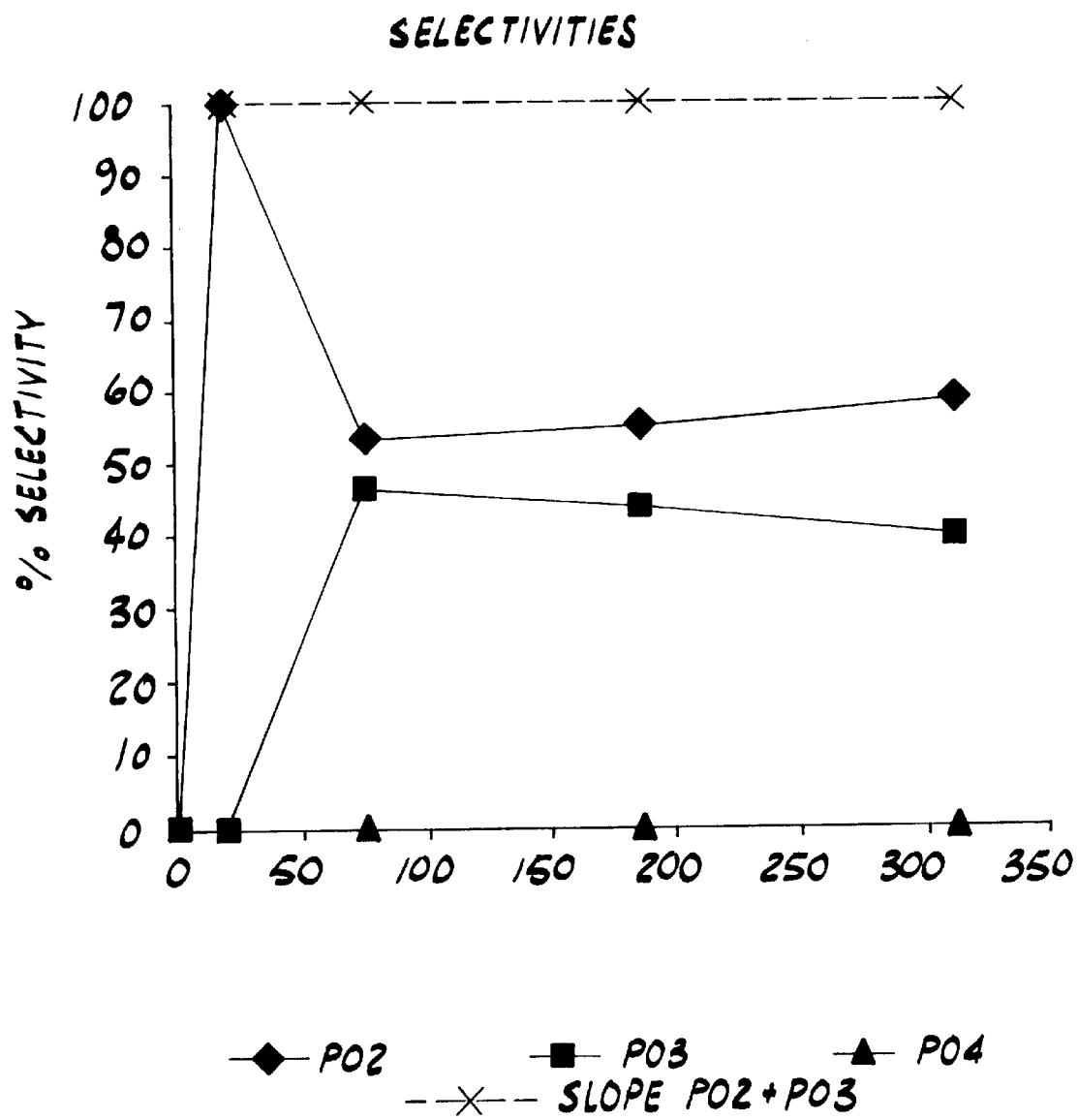
FIG. 27 is a plot of selectivity vs. time in the reaction system of Example 41.
Figure 28:
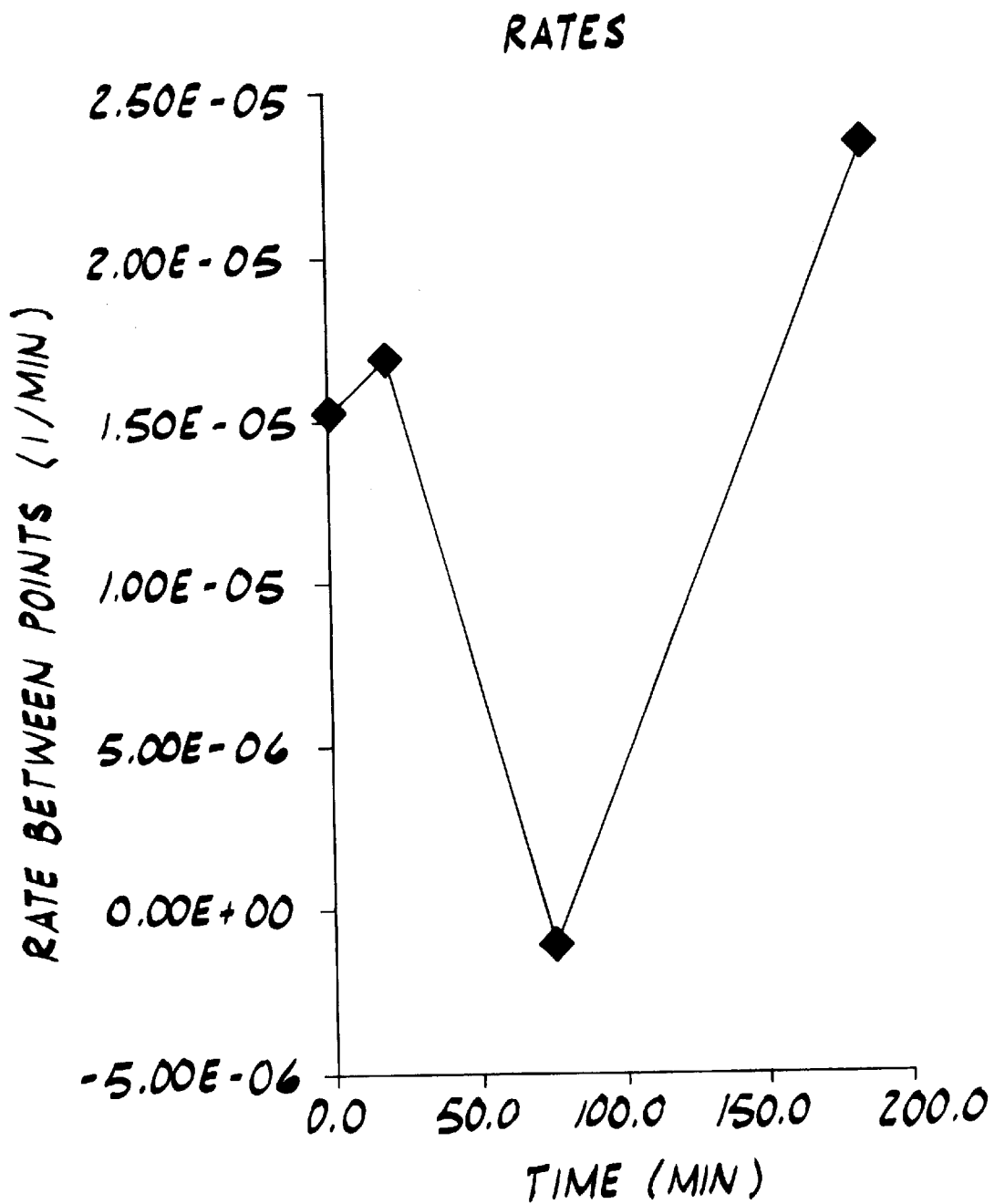
FIG. 28 is a plot of reaction rate vs. time in the reaction system of Example 41.

Illustrated in FIG. 24 is an alternative embodiment of FIG. 8 in which the catalyst is dispersed in the phosphorus phase rather than maintained in fixed bed. It has been found that the affinity of a platinum metal or other catalyst for elemental phosphorus is sufficient to preserve the catalyst in the phosphorus phase under relatively vigorous agitation, even at agitation sufficient to substantially disperse the phosphorus phase in the aqueous phase in mixer 8. In this embodiment, the catalyst is maintained in intimate contact with the phosphorous phase throughout its sojourn through the mixer/settler reaction system, not merely during its passage through a fixed catalyst bed, thereby substantially contributing to the productivity of the process.

Figure 9:
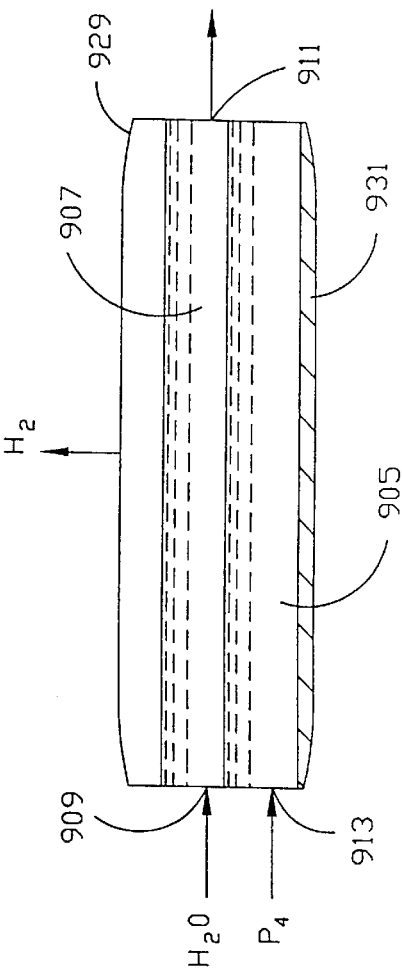

FIG. 9 illustrates a further apparatus of the invention comprising a reservoir 929 for a body or pool 905 of a substantially water-immiscible liquid containing tetraphosphorus. An aqueous liquid may be introduced into the reservoir via an inlet 909 and product aqueous liquid removed via an outlet 911. A catalyst bed 931 on the bottom wall of reservoir 929 is in contact with the phosphorus phase and remote from the phosphorus/aqueous interface, the catalyst bed comprising a noble metal or other catalyst for the oxidation of tetraphosphorus by reaction with water. Means for flowing aqueous liquid across a surface of the phosphorus pool comprises inlet 909 and outlet 911, and optionally other conventional means for urging and directing the flow. As the aqueous phase 907 flows over the phosphorus pool 905, water is transferred from the aqueous phase to the phosphorus phase, and phosphorus oxidation products are transferred from the phosphorus phase to the aqueous phase. Reservoir 929 is configured to provide a substantial interfacial contact area between the liquid phases for promotion of mass transfer.

In operation of the apparatus of FIG. 9, reservoir 929 is preferably in the form of a relatively shallow trough wherein the ratio between the liquid/liquid interfacial area and the volume of phosphorus phase pool is at least about 50 ft$^{-1}$. To minimize oxidation to phosphoric acid, the sum of the molar concentrations of all oxyacids in the solution exiting the reactor is preferably not greater than about 80%. To minimize energy costs in producing concentrated phosphorous acid, the sum of the molar concentrations of P oxyacids is at least about 2.4.

Any of the apparatus of FIGS. 1–4 and 6–9 can be operated to conduct the process of the invention on a batch, semibatch, semicontinuous, or continuous basis. In continuous operation, aqueous liquid is continuously or intermittently introduced into the mixing tank or reservoir and, in each system other than that of FIG. 8, product solution is continuously or intermittently removed from the reservoir. In carrying out the process in the system of FIG. 8, an intimate mixture of the aqueous and phosphorus phases is continuously or intermittently removed from the mixer, and product solution is continuously or intermittently removed from separator 839. Since for many catalysts the catalytic oxidation reaction has been demonstrated to be apparent zero order even at high conversions without observable increase in P(V) acid formation, it is feasible and advantageous to operate a continuous reaction system in which the aqueous phase contains a high concentration of P(I)+P(III) oxyacids, e.g., 50 to 90% by weight. For control of product composition, flow of the aqueous phase is preferably established and maintained at a substantially constant, continuous steady state rate. However, continuous operation does not require continuous introduction of molten tetraphosphorus or tetraphosphorus solution into the reservoir or mixer. A substantial charge of tetraphosphorus may be initially introduced, after which replenishment may be provided either continuously, periodically, or irregularly as required.

As indicated above, a significant startup time may be required for a heterogeneous catalyst, such as a noble metal catalyst, to become fully wetted and encapsulated by the phosphorus phase. Thus, in either a batch or continuous system for oxidation of $P_4$, tetraphosphorus should be supplied and replenished in sufficient frequency and volume to preserve the encapsulation and prevent unnecessary exposure of active catalyst sites to the aqueous phase. It has been found that the catalytic oxidation of P(I) to P(III) acid proceeds at a satisfactory rate in the aqueous phase under temperature conditions too mild for the further oxidation of P(III) to P(V), despite the fact that the catalyst is in direct contact with the aqueous phase. This contrasts with the catalytic oxidation of $P_4$ where satisfactory conversion rates are achieved only at time/temperatures combinations that could promote the further oxidation of P(III) to P(V) should the catalyst come in substantial contact with the aqueous phase.

Figure 5:
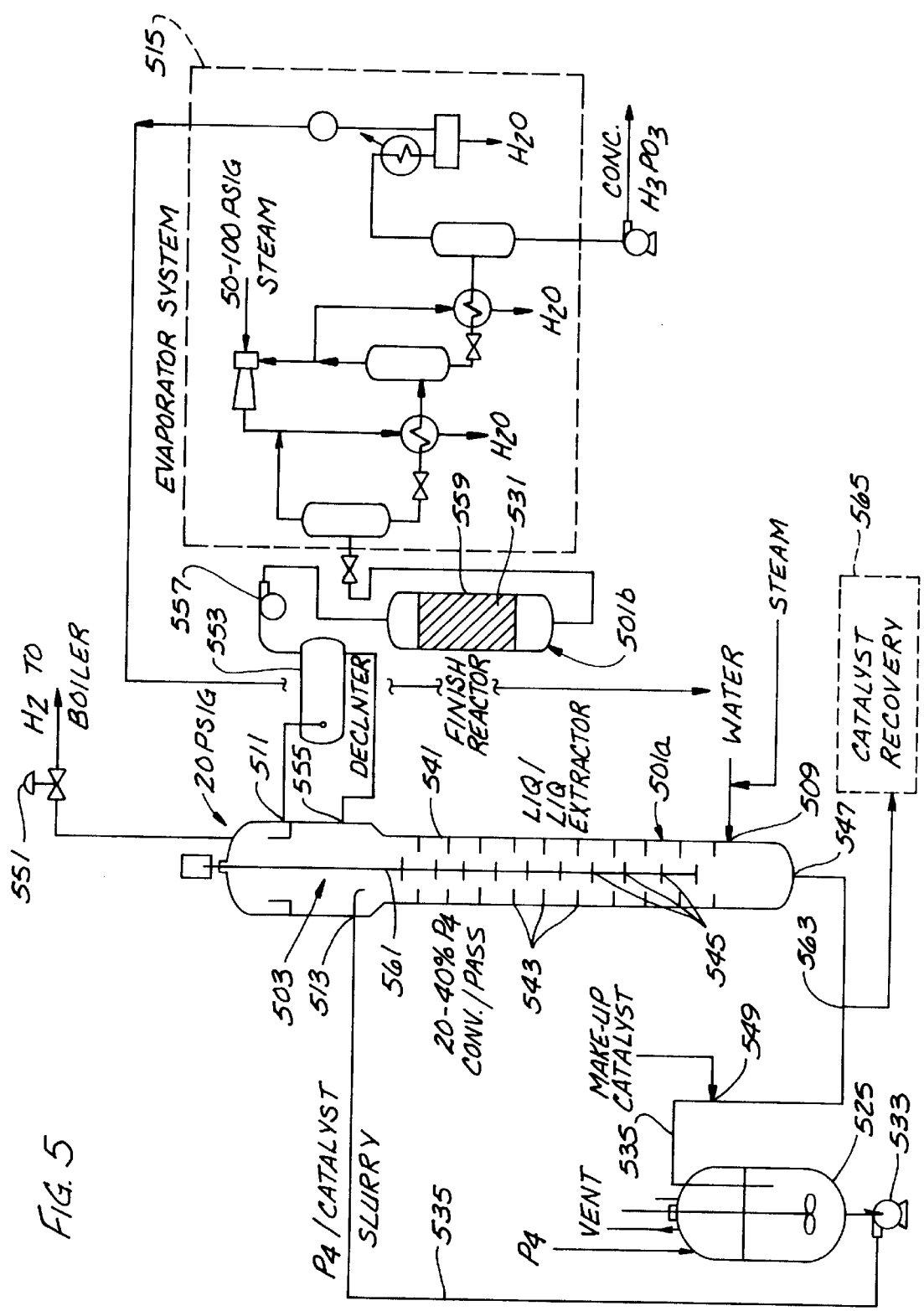

FIG. 5 illustrates another apparatus and process flowsheet of the invention. A phosphorus phase comprising a mixture of molten $P_4$ and noble metal or other catalyst is prepared in a catalyst slurry and pretreatment tank 525. The catalyst can be reduced by treatment with hydrogen introduced into the slurry prior to startup of the process. In operation of the process, the phosphorus phase comprising $P_4$ and catalyst is circulated between a phosphorus phase reservoir comprising tank 525 and a heterogeneous liquid phase reactor 501a by circulating means comprising a pump 533 and a line 535. Reactor 501a comprises a vertical column 541 having a series of annular baffles 543 vertically spaced along the inside wall thereof. An agitator 503 comprises a shaft 561 on the centerline of the column. Shaft 561 carries a series of impellers 545, each impeller being positioned between a pair of successive baffles, with the agitated zone between each such baffle pair defining a contact stage of a multistage liquid/liquid contact zone. The phosphorus phase comprising the $P_4$/catalyst mixture is introduced into the top of reactor 501a via an inlet 513 and flows downwardly through the column countercurrently to an aqueous phase flowing upwardly. Water or other aqueous liquid is introduced near the bottom of the column at an inlet 509. Water is transferred to the phosphorus phase in the liquid/liquid contact zone and reacts with $P_4$ to produce phosphorus oxyacids which are transferred from the phosphorus phase to the aqueous phase. Preferably agitator 503 is rotated at a speed which promotes mass transfer between the phases without significant entrainment of catalyst into the aqueous phase, so that the products of the reaction are primarily P(III) and P(I) acids. The temperature in reactor 501a is preferably maintained at between about 500 and about 200° C.

Phosphorus phase saturated with water is removed from reactor 501a via exit 547 at the bottom of the column and is returned to tank 525. Hydrogen produced by the reaction in column 541 is released through a pressure relief or control valve 551. Reaction continues in the recirculating phosphorus phase, and hydrogen produced in the return line and in tank 525 is vented from the tank. Makeup catalyst is introduced as needed into line 535 at port 549. A fraction of the catalyst is continuously or periodically purged from the process via a port 563 and transferred to a catalyst recovery operation 565.

Phosphorus oxyacid solution is removed from the column at an exit 511 near the top of the column and flows to a separator (decanter) 553 for separation of residual phosphorus phase that may be entrained in the aqueous phase. Phosphorus phase removed from the bottom of separator 553 is returned to the upper portion of reactor 501a at a recycle port 555. Aqueous phase, typically comprising 2–80% by weight $H_3PO_3$ and a substantial fraction of $H_3PO_2$ is decanted from the separator and passed through a finishing reactor 501b by a pump 557, gravity or other means for transfer. Reactor 501b comprises a finishing reaction zone comprising a fixed catalyst bed 531 contained within a reactor shell 559. Preferably, reaction is conducted in reactor 501b at a temperature between about 30° and about 160° C. The aqueous reaction solution exiting reactor 501b typically has a phosphorous acid concentration of at least about 2% by weight, preferably between about 20% and about 80% by weight, a phosphoric acid concentration no greater than about 15% by weight, a hypophosphorous acid concentration no greater than about 60% by weight, a molar ratio of phosphorous to phosphoric acid of at least about 5, a molar ratio of phosphorous acid to hypophosphorous acid of at least about 0.2, and a molar ratio of the sum of [P(III)+P(I)] acids to P(V) acid of at least about 5.

Countercurrent flow through reactor 501b preserves a significant driving force for mass transfer and $P_4$ oxidation throughout the column. Continuing reaction in tank 525 produces a high phosphorus oxyacid/water ratio in the phosphorus phase returning to column 541 at inlet 513, while the water phase entering at inlet 509 is substantially devoid of phosphorus oxyacids. Countercurrent flow maintains the phosphorus phase oxyacid/water ratio operating line significantly above the aqueous phase oxyacid/water ratio operating line across the entire liquid/liquid contact zone, promoting enrichment of the aqueous phase exiting the column and transfer of reactant water to the phosphorus phase.

Phosphorus oxyacid solution exiting reactor 501b may be used directly in other processes, or preferably further concentrated in an evaporation system 515. Preferably, evaporation system 515 comprises a double or triple effect vacuum evaporator. Depending on the concentration and temperature of the acid solution exiting reactor 501b, it may be feasible to remove part of the water in a flash tank upstream of the evaporator. Steam from a vacuum jet may be condensed in an indirect heat exchanger serving as a preheater for the solution the evaporator.

In a particularly preferred embodiment of the process of FIG. 5, reactor 501a is operated under pressure at a relatively elevated temperature effective for oxidation of elemental phosphorus, e.g., 110° to 150° C., and then let down through a pressure reducing valve to flash off water vapor in reactor 501b, which is preferably maintained under vaccuum. This procedure concentrates the phosphorus oxyacids in the aqueous phase and reduces the temperature of the aqueous phase to a temperature appropriate to the oxidation of P(I) acid to P(III) acid in reactor 501b, e.g., 50° to 90° C. preferably 50° to 70° C. If reactor 501a is operated at a high steady state concentration of P(I)+P(III) acid, e.g., 50% to 70% by weight, an even more concentrated solution of P(III) acid is produced in reactor 501b. This stratagem is particularly advantageous in a continuous reaction system, but can be used in any system comprising a finishing reactor, e.g., that of FIG. 3, regardless of whether it is operated on a batch or continuous basis.

Figure 10:
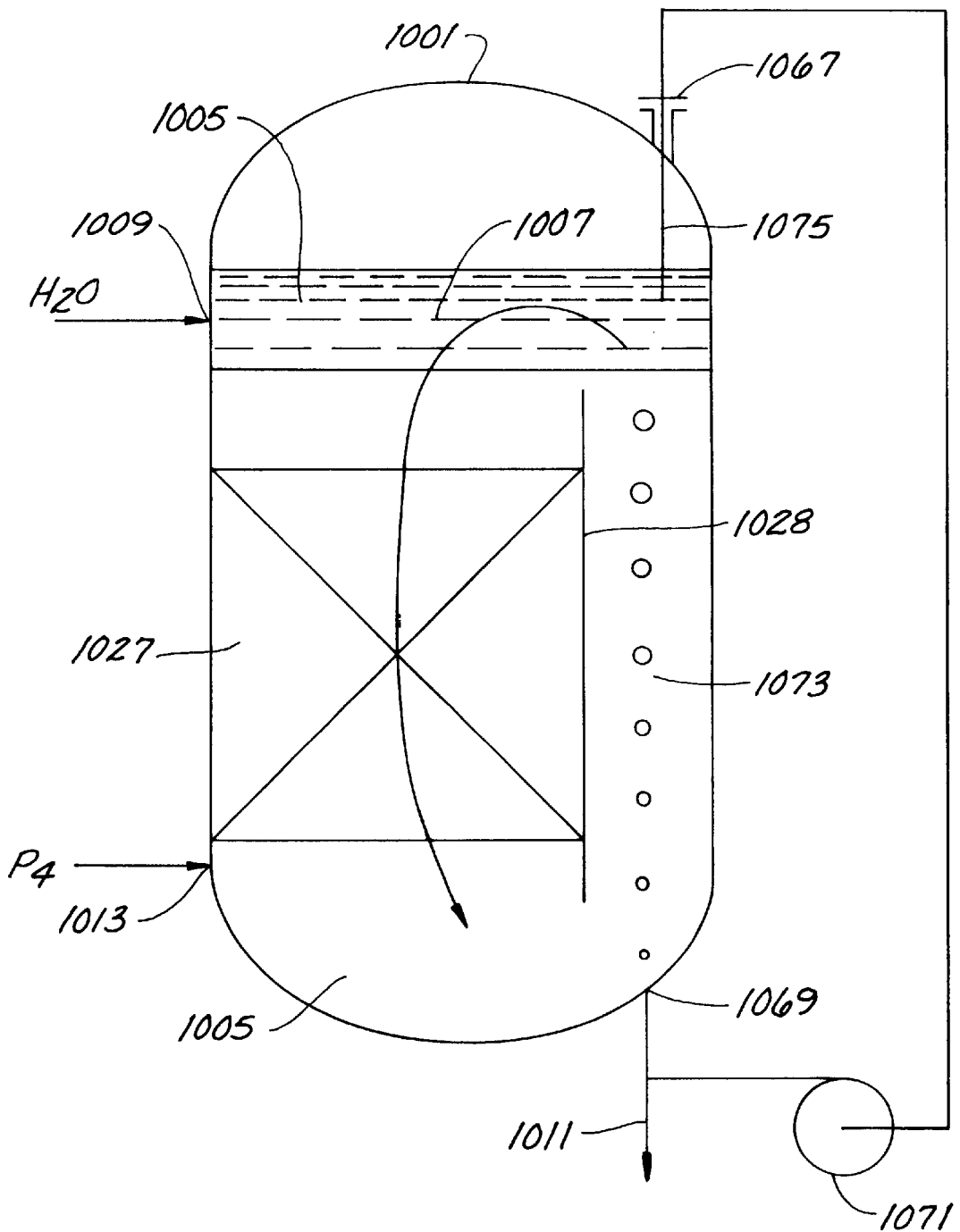

FIG. 10 illustrates a further preferred embodiment of the invention in which the catalytic oxidation of phosphorus is conducted in a lift reactor. Within reactor 1001 is a catalytic reaction zone comprising a fixed catalyst bed 1027 containing a noble metal or other catalyst for the oxidation reaction. Bed 1027 is partitioned from the remainder of the reactor interior by a wall or baffle 1028. The reactor is charged with a phosphorus phase, preferably molten phosphorus, and an aqueous liquid so that catalyst bed 1027 is immersed in a phosphorus phase pool 1005 below the interface between the phosphorus phase and the aqueous phase 1007. No mechanical agitator is necessarily provided, but aqueous phase is continually withdrawn from the upper portion of the reactor through an exit nozzle 1067 and returned to the bottom of reactor 1001 through a return nozzle 1069 via an aqueous phase circulating pump 1071. Both nozzles are in direct communication with a zone 1073 of the reactor defined by the interior wall of the reactor and a side of baffle 1028 opposite from catalyst bed 1027. Return nozzle 1069 is positioned at the lower end of zone 1073, and exit nozzle 1067 carries a dip leg 1075 having its lower end positioned within the aqueous phase above the $P_4$/aqueous interface. Optionally, the return line may extend upwardly from nozzle 1069 by some vertical distance into the zone 1073, and may have a frit or other device on the end thereof for dispersing the returning aqueous phase and thereby increasing the interfacial area between the returning aqueous phase and the phosphorus phase into which it is introduced. In any event, zone 1073 is oriented to comprise a liquid lift leg for circulation of phosphorus between the catalyst bed and the leg, the upper end of the lift leg being in liquid flow communication with the top of the catalyst bed and the lower end of the leg being in liquid flow communication with the bottom of the catalyst bed. The leg is sized and configured so that the phosphorus phase at the bottom of the catalyst bed has access to the lower portion of the leg, and the velocity of the aqueous phase rising therein is sufficient to draw phosphorus phase from the bottom of the bed and circulate it through and over the top of the leg to the upper portion of the bed, promoting liquid/liquid contact between the liquid phases and circulation of phosphorus phase through the bed. The lift leg may be defined by the contours of zone 1073, or may comprise a draft tube or a baffled vertical passage within said zone. Pump 1071 is sized and operated to promote mass transfer between the phases and circulation of phosphorus phase through the catalyst bed, but the pumping rate is maintained low enough to preserve the integrity of the phases and avoid drawing aqueous phase through the catalyst bed.

Although treatment to reduce the catalyst is generally desirable to limit affinity of the catalyst for the aqueous phase and thereby contribute to selectivity to P(I) and P(III) oxyacids, some catalysts may have a preferential affinity for the phosphorus phase without being subjected to any reductive treatment prior to use in the phosphorus oxidation reaction. For example, it has been observed that certain catalysts, e.g. $CuCl_2$, provide enhanced productivity in the oxidation of $P_4$ without pre-treatment by a reducing agent, though it remains possible that the presence of elemental phosphorus may in some instances be effective to reduce the catalyst during the course of the reaction, e.g., in formation of a catalytically active copper phosphide. In the various embodiments of the process as described hereinabove, it may be desirable to continually introduce fresh or non-reduced phosphophilic catalyst into contact with the phosphorus phase, preferably in a manner that minimizes the occasion for contact of the catalyst with the aqueous phase before the catalyst is assimilated into the phosphorus phase. By thus "bleeding" catalyst into the reaction zone, productivity of the reaction may be enhanced without significant sacrifice of selectivity.

The process of the invention can be operated to provide very high yields of phosphorus oxyacids. Modest formation of phosphine by-product has been observed, especially early in the reaction using certain catalysts such as copper, but where the desired product is phosphoric acid, yields approaching 100% can be readily achieved. Where the desired product is phosphorous acid, yield is limited by selectivity, but very high selectivities are achievable as discussed above. Regardless of whether selectivity to phosphorous acid may decline at high conversions in the presence of $P_4$, favorable selectivity and yield can nonetheless be preserved by use of the process as illustrated in FIG. 3 or FIG. 5. The process of FIGS. 3 and 5 are also effective where high conversions of elemental phosphorus are achieved in the primary reactor, but a substantial fraction of the aqueous product exiting the primary reactor is P(I) rather than P(III) acid.

In commercial operation of the process of the invention, it is particular preferred that a high concentration of P(I)+P(III) acid be obtained in the initial reaction between elemental phosphorus and water. Thus, in a continuous process according to FIG. 24, it is preferred that the reactants be fed to the primary reaction system at relative rates sufficient to provide a concentration of P(I)+P(III) oxyacids in the primary aqueous reaction product that is as close to the target concentration of P(III) acid (or P(I)+P(III) acid) in the ultimate product as selectivity considerations permit.

Consistent with preservation of requisite selectivity, the primary reaction product preferably has a concentration of P(I)+P(III) at least about 0.15, more preferably at least about 0.45, most preferably at least about 0.60, times the concentration of P(I)+P(III) in the ultimate product. Not only does a high concentration of P(I)+P(III) acid in the primary aqueous reaction product minimize the capital and operating costs of an evaporator (or other system) for concentrating the reaction product, it also minimizes the requisite size and capital cost of both a primary reaction system for conversion of elemental phosphorus to P(I)+P(III) acid and a finishing reaction system for conversion of P(I) acid in a crude reaction product to P(III) acid. For example, for the ultimate preparation of 85% by weight phosphorous acid, it is preferable that the primary reaction system be operated to provide a reaction product having a concentration of at least 15% by weight, more preferably at least about 35% by weight, most preferably at least about 50% by weight P(I)+P(III) acid. Optimal acid concentration exiting the primary reaction system is between about 60% and about 85% by weight. As noted, concentrations in this range can be realistically achieved even in, or especially in, a continuous back mixed reaction zone. Conversions per pass are generally less critical than concentration in high volume operations, but in a continuous reaction system of the type illustrated in FIG. 24 the optimal conversion per pass may be as low as 3 to 6%. Whatever reaction system is used in conducting the process of the invention, the reaction vessel, and other piping and equipment which comes in contact with a water/phosphorus/catalyst mixture under reactive conditions, is preferably constructed of a material which does not release trace metals into the mixture. Metals such as Fe and Ni at concentrations in the aqueous phase as low as 10 to 50 ppm or even lower, and other trace metals, have been observed to catalyze conversion of P(III) oxyacid to P(V). Accordingly, it is particularly preferred that the oxidation reactor be glass lined. Consistently high selectivities to P(I)+P(III) have been demonstrated in glass reactors.

The process of the invention is especially advantageous in eliminating the need for halogenated phosphorus substrates in the preparation of phosphorous acid. Not only does the process avoid the expense associated with consumption of molecular chlorine or other halogen raw material, but it further avoids the handling of highly toxic halogens and phosphorus halides, contamination of the phosphorous acid product with halogenated by-products, the need for operations which separate halogenated by-products from the phosphorous acid, and problems associated with disposal of such by-products, which typically are not saleable.

The process of the invention is particularly suited to prepare phosphorous acid for use in phosphonomethylation reactions, especially phosphonomethylations conducted in the manufacture of N-phosphonomethylglycine ("glyphosate"). Glyphosate is manufactured by any of a variety of processes in which a mono-N-substituted glycine (e.g., iminodiacetic acid) salt thereof (cf. U.S. Pat. Nos. 5,292,936, 5,367,112, 5 5,627,125, and 5,689,000) is reacted with phosphorous acid and formaldehyde to produce N-substituted glyphosate (e.g. N-phosphonomethyliminodiacetic acid), and the N-substituted glyphosate subjected to oxidation to cleave the original N-substituent yielding glyphosate. Phosphorous acid used in the preparation of glyphosate has typically been prepared by hydrolysis of $PCl_3$, a process which is effective for the purpose but which yields a phosphorous acid intermediate contaminated with chloride ions. Cumbersome and expensive process steps are required for the removal of chloride ions, typically in the form of NaCl, from the phosphorous acid intermediate or from the N-substituted glyphosate intermediate or glyphosate product. The process of the invention provides a source of phosphorous acid that is entirely free of chlorides, so that the use of this intermediate in the manufacture of glyphosate eliminates the need for removal of salt in downstream processing.

Phosphorous acid produced in accordance with the invention can be used in any of the various phosphonomethylation processes known to the art. Preferred phosphonomethylation processes are described for example in U.S. Ser. No. 09/022, 967, filed Feb. 12, 1998 (MTC 6450), U.S. Pat. Nos. 5,292,936, 5,367,112, 5,627,125, and 5,689,000, the texts of which are expressly incorporated herein by reference.

The following examples illustrate the invention:

EXAMPLE 1

Water (50 ml, which had been purged for 30 minutes with argon), tetraphosphorus (1.626 g; 0.013 moles), and palladium black (0.111 g; 0.001 moles; 2 mole % with respect to phosphorus atoms) were placed in a 3-neck 100 ml round bottom flask which had been purged with nitrogen to before charging. The flask was placed in a 75° C. oil bath for 68 hours under a nitrogen blanket, after which the temperature was increased to 90° C. and held at that temperature for 8 hours. A nitrogen atmosphere was maintained throughout the course of reaction. A sample of the aqueous phase was then withdrawn and analyzed by ion exchange chromatography (IC) and found to contain the following yields of $PO_x$ species: 0.86% $H_3PO_2$; 13.1% $H_3PO_3$; 0.23% $H_3PO_4$, thereby providing a P(I)+P(III) selectivity of 98%. Throughout the reaction, hydrogen evolution was observed.

EXAMPLE 2

Water (150 ml, which had been purged for 30 minutes with argon), tetraphosphorus (1.05 g; 0.0085 moles), and palladium black (0.54 g; 0.00507 moles; 15 mole % with respect to phosphorus atoms) were charged to a 300 ml Hastelloy C autoclave. The autoclave was closed and purged of oxygen. The reactor was then warmed to 150° C. and held for 2 hours. Pressure in the closed reactor rose steadily over this period and the pressure increase was found to be predominantly due to hydrogen evolution. After 2 hours at 150° C., a liquid sample was withdrawn and analyzed by IC for phosphorus oxyacids. Phosphoric acid was found, the concentration of which accounted for about 80% of the tetraphosphorus initially charged to the reactor. No phosphorous acid or hypophosphorous acid was identified in the product sample.

EXAMPLE 3

Water (160 ml) was charged to a 300 ml autoclave which had been purged with argon. In sequence following the addition of water, white phosphorus (1.501 g; 0.01212 moles) and palladium black powder (2.511 g; 0.02360 moles; 49% based on phosphorus atoms) were introduced into the autoclave. The reactor was then closed and purged of oxygen. The autoclave was heated to 75° C. and stirred at 1,100 rpm for 7.5 hours. Reaction progressed, during the course of which the pressure increased to about 130 psig (i.e., about 998 kPa). A sample was removed from the reaction mixture and analyzed by IC and found to yield 20.9% $H_3PO_3$ and 66.1% $H_3PO_4$. Conversion to phosphorus oxyacids was determined to be about 87%. The P(III) selectivity was 24%.

EXAMPLE 4

Palladium black powder (0.140 g; 0.00132 moles; 2% based on phosphorus atoms) was heated to 100° C. under vacuum for two days, and thereafter added in small portions to molten white phosphorus (1.939 g; 0.01565 moles) in a test tube at 50° C. Each addition of palladium was followed by a small flash of yellow light and evolution of small quantities of a white gas, believed to be phosphorus vapor. The phosphorus/palladium mixture was allowed to cool until it solidified and was then placed in a 200 ml 3-neck flask that had previously been charged with water (100 ml). The resulting reaction mixture was heated to 90° C. for 3 days under moderate agitation. The intensity of agitation was moderate enough to preserve the phosphorus phase as a pool below the aqueous phase at the bottom of the reactor, but was sufficiently vigorous to continually break off phosphorus phase globules of approximately 1 mm diameter, the globules being continually reabsorbed by the phosphorus phase as new globules were formed. During the course of the ensuing reaction, hydrogen was detected in the head space gases. A sample was removed from the reaction mixture and analyzed by IC and found to yield 0.44% $H_3PO_2$, 21.4% $H_3PO_3$ and 2.2% $H_3PO_4$, thereby providing a P(I)+P(III) selectivity of 91%. The conversion data is represented graphically in FIG. 12.

EXAMPLE 5

Palladium black powder (0.140 g; 0.00132 moles; 2 mole % based on phosphorus atoms) was heated under vacuum as described in Example 4, then added in small portions to the molten white phosphorous (2.069 g; 0.0167 moles) in a test tube at 50° C. Each addition of palladium was followed by a flash of yellow light and evolution in small quantities of a white gas, believed to be phosphorus vapor. The phosphorus/palladium mixture was allowed to cool until it solidified and was then placed in a 200 ml 3-neck flask that had been previously charged with water (100 ml). The resulting reaction mixture was heated to 90° C. for 6 days under moderate agitation as described in Example 4. During the course of the reaction, hydrogen was detected in the head space gases. A sample was removed from the reaction mixture and analyzed by IC and found to yield 0.7% $H_3PO_2$, 65.1% $H_3PO_3$, and 5.6% $H_3PO_4$ with P(I)+P(III) selectivity of 94%. The conversion data is represented graphically in FIG. 12.

EXAMPLE 6

Water (50 ml), white phosphorus (1.612 g; 0.0130 moles) and palladium black powder (0.109 g; 0.00104 moles; 2 mole % based on phosphorus atoms) were placed in a 3-neck 100 ml flask. This charge mixture was heated at 50° C. for 20 hours at which time the temperature was raised to 75° C. for 93 hours, after which the reaction temperature was raised to 90° C. for 7 hours. The progressive increase in the reaction temperature was intended to allow incorporation of Pd into the phosphorus phase at low temperature, thereby minimizing oxidation of P(III) to P(I) acid during incorporation. The reaction mixture was subjected to moderate agitation as described in Example 4. During the course of the reaction, hydrogen was detected in the head space gases. A sample was removed from the reaction mixture and analyzed by IC and found to yield 3.1% $H_3PO_2$, 13.0% $H_3PO_3$, and 2.0% $H_3PO_4$. P(I)+P(III) selectivity was 89%.

EXAMPLE 7

Water (50 ml), white phosphorus (1.853 g; 0.1496 moles) and palladium black (0.128 g; 0.00120 moles; 2 mole % based on phosphorous atoms) were placed in a 3-neck 100 ml flask. The reaction mixture was heated at 75° C. for 18½ hours under moderate agitation which preserved the phosphorus phase as a pool at the bottom of the reactor but with continual break-off of phosphorus globules from the phosphorus phase and reabsorption thereof into the pool. After 18½ hours, all the water covering the molten phosphorus/palladium pool was removed. The water phase that was removed was observed to contain a majority of the palladium that was originally charged. The phosphorus/palladium pool was then washed with water (30 ml) and stirred for about 5½ minutes. The spent wash water was removed with the intent of removing the remaining suspended palladium. The surface of the phosphorus/palladium pool was observed to have a silvery, metallic appearance when not covered with water. A fresh aliquot of water (50 ml) was then added to the reactor and the temperature increased to 90° C. After 78 hours, the sample was removed and analyzed by IC and found to yield 0.19% $H_3PO_2$, 1.6% $H_3PO_3$, and 0.29% $H_3PO_4$. Selectivity to P(I)+P(III) was 86%.

EXAMPLE 8

Water (50 ml), 50% hypophosphorous acid (8.55 g; 0.0648 moles) and palladium black powder (0.142 g; 0.00133 moles; 2 mole % based on phosphorus atoms) were added to a 3-neck 100 ml flask. This reaction mixture was heated at 75° C. for 30 minutes at which time the hypophosphorous acid in the charge was substantially oxidized to phosphorous acid. Tetraphosphorus (1.932 g; 0.01560 moles) was then added to the mixture re-establishing a 2% mole ratio of palladium to phosphorus. The reaction mixture was stirred under moderate agitation at 75° C. for 66 hours at which time the palladium charge had been entirely absorbed into the phosphorus phase. The temperature was increased to 90° C., the reaction mixture was subjected to moderate agitation as described in Example 4, and the conversion of elemental phosphorus was monitored. After about 8 days, the sample was removed and analyzed by IC and found to reflect a conversion of the initial phosphorus charge to phosphorus oxyacids of 57%. A noteworthy feature of this Example is that after elemental phosphorus was added, the rate of formation of phosphoric acid was dramatically reduced by two orders of magnitude.

EXAMPLE 9 (comparative)

Water (50 ml) and white phosphorus (2.075 g; 0.01675 moles) were placed in a 3-neck 100 ml flask and the resulting mixture heated to 90° C. for about 2 days. At this time, a sample was removed from the reaction mixture and analyzed by IC and found to yield 0.019% $H_3PO_2$, 0.070% $H_3PO_3$, and 0.082% $H_3PO_4$. P(I)+P(III) selectivity was 52%. This example illustrates the substantial non-reactivity of tetraphosphorus with water in the absence of a catalyst for the reaction, as well as the poor selectivity obtained in whatever reaction does occur.

EXAMPLE 10

Hypophosphorous acid (50% strength; 123.97 g; 0.939 moles) and palladium black (1.70 g; 0.160 moles; 1.73 mole %) were charged to a 500 ml, 3-neck, round bottom flask equipped with a nitrogen purge, a stir bar, and a reflux condenser. The flask was placed in an oil bath at 75° C. for 2 hours at which time hydrogen evolution had subsided. The reaction mixture was then allowed to cool and was filtered. The reaction flask and catalyst were washed with two small portions of deionized water (about 15 ml). The water washes were added to the filtrate and analyzed.

Palladium black in the filter was returned to a round bottom flask that had been already charged with hypophosphorous acid (50% by weight strength; 119.88 g; 0.908 moles). The flask was then placed in an oil bath at 75° C. for 2 hours at which time hydrogen evolution had subsided. The reaction mixture was allowed to cool and was filtered. The reaction flask and catalyst were washed with two small portions of deionized water (about 15 ml). The water washes were added to the filtrate and analyzed.

Results of the analyses are set forth in Table 1 below:

TABLE 1

| | Selectivity to $H_3PO_3$ | | |
|---|---|---|---|
| | $^{31}$P NMR | IC | Mass Balance |
| Cycle 1 | 99.2% | 99.9% | 99% |
| Cycle 2 | 99.5% | 99.9% | 101% |

EXAMPLE 11

Palladium black used in this Example had been heated to 100° C. under vacuum for 2 days. Palladium (black) powder (0.32 g, 0.00301 moles, 6 mole % based on P atoms) was added in small portions to molten white phosphorus (1.58 g, 0.0129 moles) in a test tube at 50° C. Each addition of palladium was followed by a flash of yellow light and the evolution of small quantities of a white gas. The phosphorus/palladium mixture was allowed to cool until it solidified and was then placed in a 100 mL 3-necked flask that had been previously charged with 70 mL of water. The reaction mixture was then heated to 90° C. for 2 days. During the course of the reaction hydrogen was detected in the head space gases. A sample was removed from the reaction mixture and analyzed by IC and found to yield 0.59% $H_3PO_2$, 52.9% $H_3PO_3$, and 5.61% $H_3PO_4$ with a P(I)+P(III) selectivity of 91%.

EXAMPLE 12

Palladium black used in this Example had been heated to 100° C. under vacuum for 2 days. Palladium (black) powder (0.24 g, 0.00226 moles, 6 mole % based on P atoms) was added in small portions to molten white phosphorus (1.16 g, 0.00936 moles) in a test tube at 50° C. Each addition of palladium was followed by a flash of yellow light and the evolution of small quantities of a white gas. The phosphorus/palladium mixture was allowed to cool until it solidified and was then placed in a 100 mL 3-necked flask that had been previously charged with 49.1 mL of water. The reaction mixture was then heated to 100° C. for 1 day. During the course of the reaction, hydrogen was detected in the head space gases. A sample was removed from the reaction mixture and analyzed by IC and found to yield 0.54% $H_3PO_2$, 43.2% $H_3PO_3$, and 5.29% $H_3PO_4$ with a P(I)+P(III) selectivity of 89%.

Figure 11:
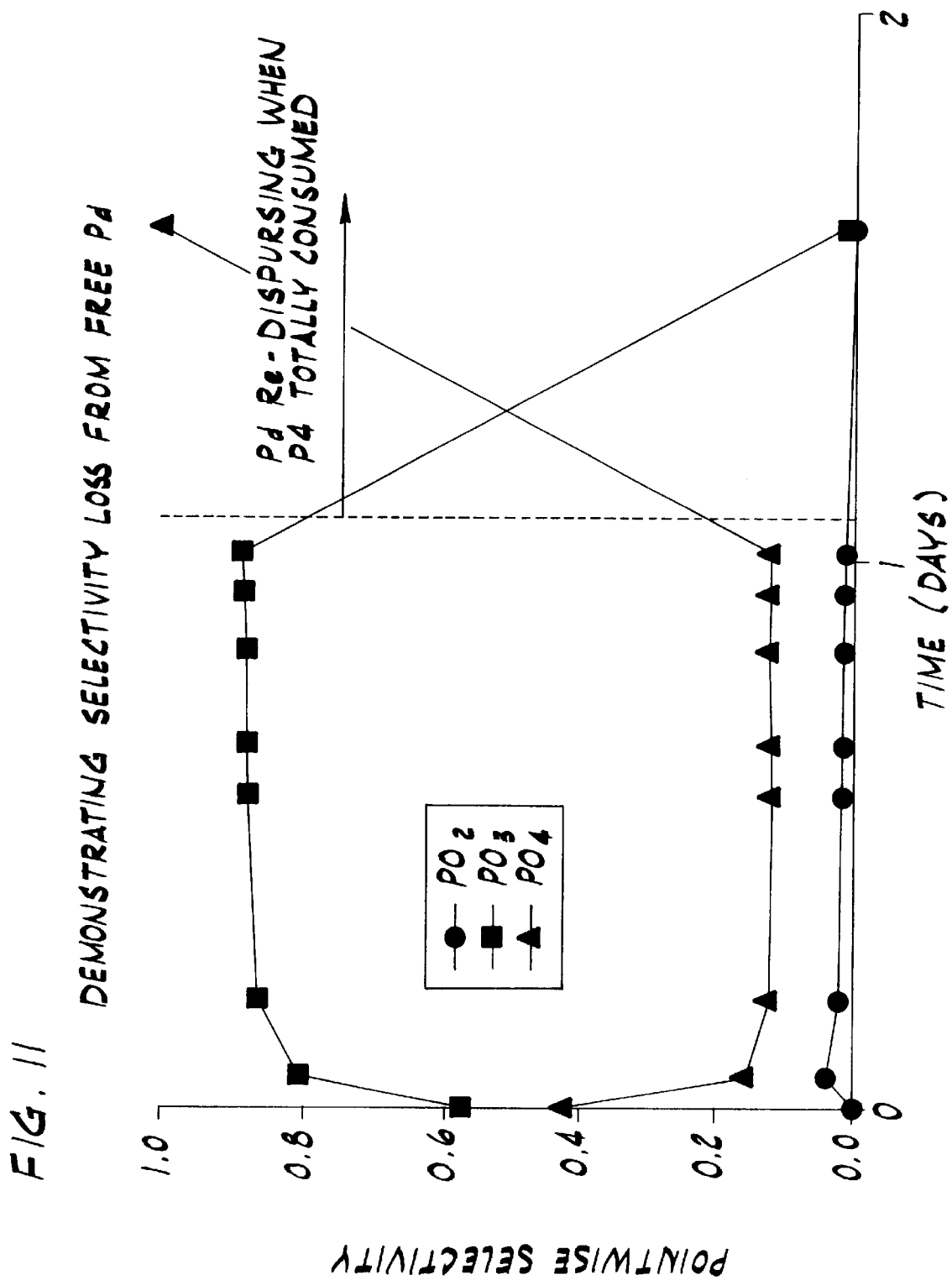
FIG. 11 is a plot of the cumulative selectivity of the reaction mixture in a heterogeneous reaction system comprising an aqueous phase, a tetraphosphorus phase and a Pd catalyst, showing the progress of the reaction both before and after exhaustion of $P_4$.

Tetraphosphorus was reacted with water in the presence of a Pd catalyst under the conditions described above until all tetraphosphorus had been exhausted (about 23 hours after the reaction began). Reaction was continued for another 12 hours after exhaustion of phosphorus. A sample was taken from the reaction mixture to monitor the progress of the reaction. The cumulative selectivities are plotted in FIG. 11. It may be seen that the reaction was highly selective for P(III) oxyacid until all $P_4$ had been consumed and Pd redispersed into the aqueous phase, after which the P(III) acid was progressively and totally converted to P(V) acid.

EXAMPLE 13

Palladium black used in this Example had been heated to 100° C. under vacuum for 2 days. Palladium (black) powder (0.29 g, 0.00273 moles, 2 mole % based on P atoms) was added in small portions to molten white phosphorous 4.249 g, 0.0343 moles) in a test tube at 50° C. Each addition of palladium was followed by a flash of yellow light and the evolution of small quantities of a white gas. The phosphorus/palladium mixture was allowed to cool until it solidified and was then placed in a 300 mL Ace Glass hydrogenation bottle that had been equipped with a claisen head adapter that was fitted with a pressure gauge and a ball valve. The bottle was charged with 99.48 mL of water. The reaction mixture was then heated to 110° C. for 8 hours. During the course of the reaction, the pressure increased to 50 psig. A sample was removed from the reaction mixture and analyzed by IC and found to yield 0.1% $H_3PO_2$, 8.7% $H_3PO_3$, and 1.18% $H_3PO_4$ with a P(I)+P(III) selectivity of 88%.

A summary of the reaction conditions of Examples 11 to 13 is set forth below:

| Example | Catalyst Loading | Temperature |
|---|---|---|
| 13 | 2 mole % vs. P | 110° C. |
| 11 | 6 mole % vs. P | 90° C. |
| 12 | 6 mole % vs. P | 100° C. |

The progress of the reaction under each combination of conditions was monitored over a period of one to three days. The yield of total to $PO_x$ as a function of time is set forth in FIG. 12. Selectivity to P(III) declined moderately with the severity of the conditions, as follows:

| Example | Relative Selectivity Among $PO_x$ Species |
|---|---|
| 13 | $PO_2$: 1%; $PO_3$: 87%; $PO_4$: 12% |
| 11 | $PO_2$: 1%; $PO_3$: 89%; $PO_4$: 10% |
| 12 | $PO_2$: 1%; $PO_3$: 88%; $PO_4$: 11% |

Figure 12:
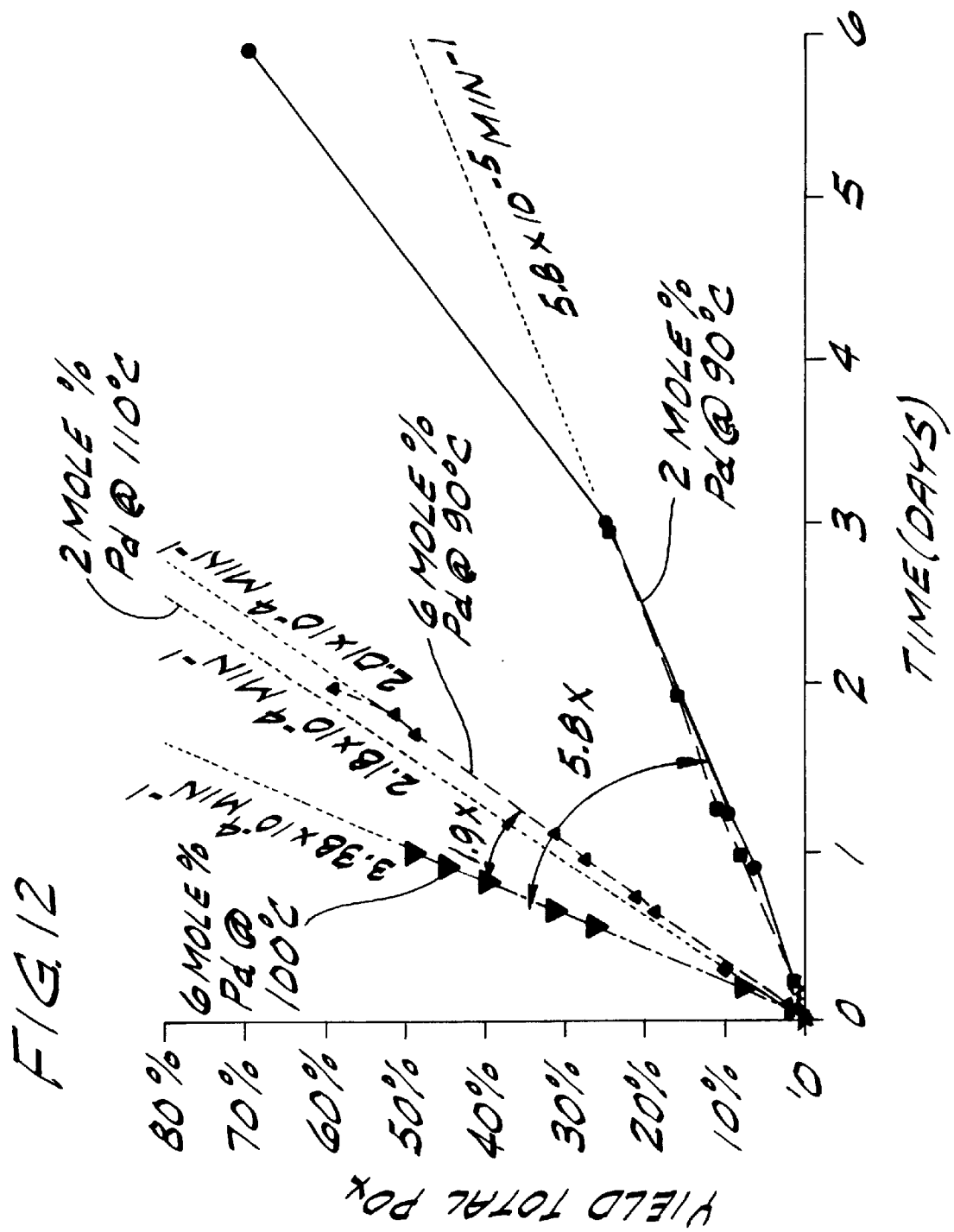
FIG. 12 is a plot of yield of $PO_x$ from tetraphosphorus as a function of time for reaction at various combinations of temperature and Pd catalyst loading in a heterogeneous reaction system comprising an aqueous phase and a tetraphosphorus phase with the catalyst incorporated in the phosphorus phase.

As indicated in FIG. 12, reaction rates tended to increase linearly with catalyst concentration and exponentially with temperature according to the conventional 10° C. rule. Thus, for the experiments of these examples, the rate of reaction was apparently limited by reaction kinetics, not by mass transfer between phases.

EXAMPLE 14

Figure 13:
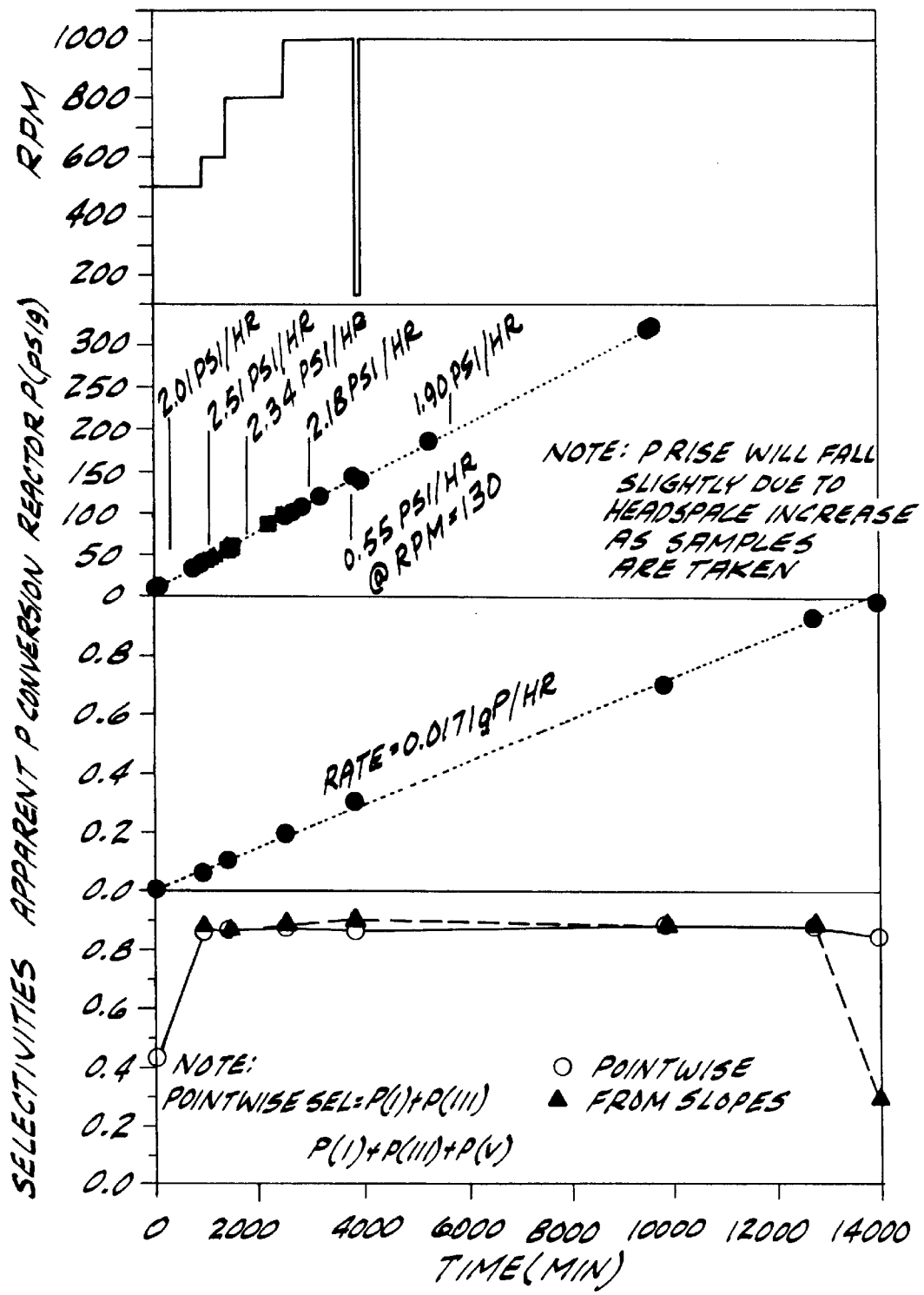
FIG. 13 comprises a plot of agitation rate as a function of time and a plot of reactor pressure and conversion as a function of time in a closed autoclave at a reaction temperature of 90° C. and Pd catalyst loading of 2 mole % based on phosphorus atoms in a heterogeneous reaction system comprising an aqueous phase and a tetraphosphorus phase.

Palladium black used in this Example had been heated to 100° C. under vacuum for two days. Pd black powder (2.80 g; 0.00263 moles; 2 mole % based on P atoms) was added in small portions to molten white phosphorus (3.936 g; 0.03177 moles) in a test tube at 50° C. The phosphorus/palladium mixture was allowed to cool until it solidified and was then placed in a 300 ml Hastelloy-C autoclave that had been previously charged with rigorously degassed water (156 ml). The reaction mixture was then heated to 90° C. for 10 days. A pumping impeller was employed for agitation and the stir speed of the impeller was varied from 500 to 1000 rpm with no substantial effects on the observed rate of reaction. The progress of the reaction was monitored by the pressure buildup in the autoclave and by taking samples of the aqueous phase of the reaction mixture. Both pressure buildup and conversion showed zero order behavior. Towards the end of the reaction a sample was removed from the reaction mixture and analyzed by IC. Conversion of $P_4$ to $PO_x$ was substantially quantitative; and the yields of $H_3PO_3$ and $H_3PO_4$ were calculated to be 81.8% and 11.2%, respectively. The selectivity to P(III) was 88%. Samples taken during the reaction cycle indicated no significant effect of pressure on selectivity. Selectivity dropped off at the end of the reaction as tetraphosphorus was exhausted. Plots of agitation rate, total reaction pressure, conversion and selectivity to P(I)+P(III) oxyacid vs. time are set forth in FIG. 13.

Palladium black used in the above examples was analyzed and determined to have a mean particle size of about 48$\mu$, a median particle size of about 41.5$\mu$ and a mode of about 72.5$\mu$. About 2.4% by weight of the catalyst was constituted of particles of a size below 1$\mu$, 7.3% below 2$\mu$, 11.0% below 5$\mu$, 14.0% below 7$\mu$ and 54.3% below 60$\mu$.

EXAMPLES 15–34

The following generic procedure pertains to the list of catalysts found in Table 2 (Examples 15–34). In an inert atmosphere, the appropriate catalyst was mixed with white phosphorus at 50° C. The phosphorus/catalyst mixture was allowed to cool and placed in a round bottom flask that had been equipped with a stir bar, a nitrogen blanket and charged with water that had been previously degassed with argon for ~30 minutes. The reaction mixtures were then heated to 90° C. In each example, a heterogeneous reaction system was maintained, comprising an aqueous phase over a pool of molten phosphorus. Moderate agitation was imposed, which was sufficient to promote mass transfer of water and phosphorus oxyacid reaction products between the aqueous and phosphorus phases. Yield of POx species P(I)+P(III), selectivities and mole % catalyst charged are reported.

TABLE 2

| EXAMPLE | CATALYST | Mole & Cat. based on P atoms) | % Yield PO2 | % Yield PO3 | % Yield PO4 | P(I) + P(III) Selectivity |
|---|---|---|---|---|---|---|
| 15 | Pd on Alumina | 0.52 | 0.7 | 6.7 | 1.7 | 81 |
| 16 | 30% Pd on activated carbon | 1.6 | 1.7 | 8.9 | 1 | 89 |
| 17 | PdO | 2 | 0.1 | 56.9 | 15 | 79 |
| 18 | PdCl2 | 2 | 1.2 | 57.4 | 6.4 | 92 |
| 19 | Raney Nickel | 6 | 0 | 25.2 | 12.3 | 57 |
| 20 | Cr powder | 6 | 0.1 | 0.3 | 0.4 | 56 |
| 21 | Ag2O | 6 | 1.4 | 3.5 | 0.7 | 93 |
| 22 | Cu powder | 6 | .1 | 0.4 | 0.3 | 60 |
| 23 | Cu2O | 6 | .3 | 1.3 | 0.6 | 75 |
| 24 | Raney Copper | 6 | 0.16 | 0.96 | 0.38 | 75 |
| 25 | 17.5% Cu/3% Pd on SA-30 | 1.08 | 2.8 | 7.3 | 0.3 | 98 |
| 27 | PbO | 6 | 0.09 | 0.34 | 0.08 | 84 |
| 28 | NiO | 6 | 0 | 11 | 2 | 85 |
| 29 | Ni2P | 6 | 0.07 | 2.26 | 0.57 | 80 |
| 30 | Cu3P | 6 | 0.16 | 0.38 | 0.26 | 68 |
| 31 | CUCl2*2H2O | 10 | 5.6 | 61.1 | 2.7 | 96–97 |
| 32 | CUCl2*2HCO | 10 | 5.8 | 22.7 | 2.2 | 93 |
| 33 | 2:1 Pd(black)CuCl 2*2H2O | 6 | 2.1 | 19.7 | 1.3 | 94 |
| 34 | Ni(cod)2 | 2 | 0.3 | 29.4 | 4.9 | 86 |

A preferred carbon support is the SA-30 support used in Example 25. The preparation of SA-30 is described in Example 1 of U.S. Pat. No. 5,689,000, expressly incorporated herein.

Figure 16:
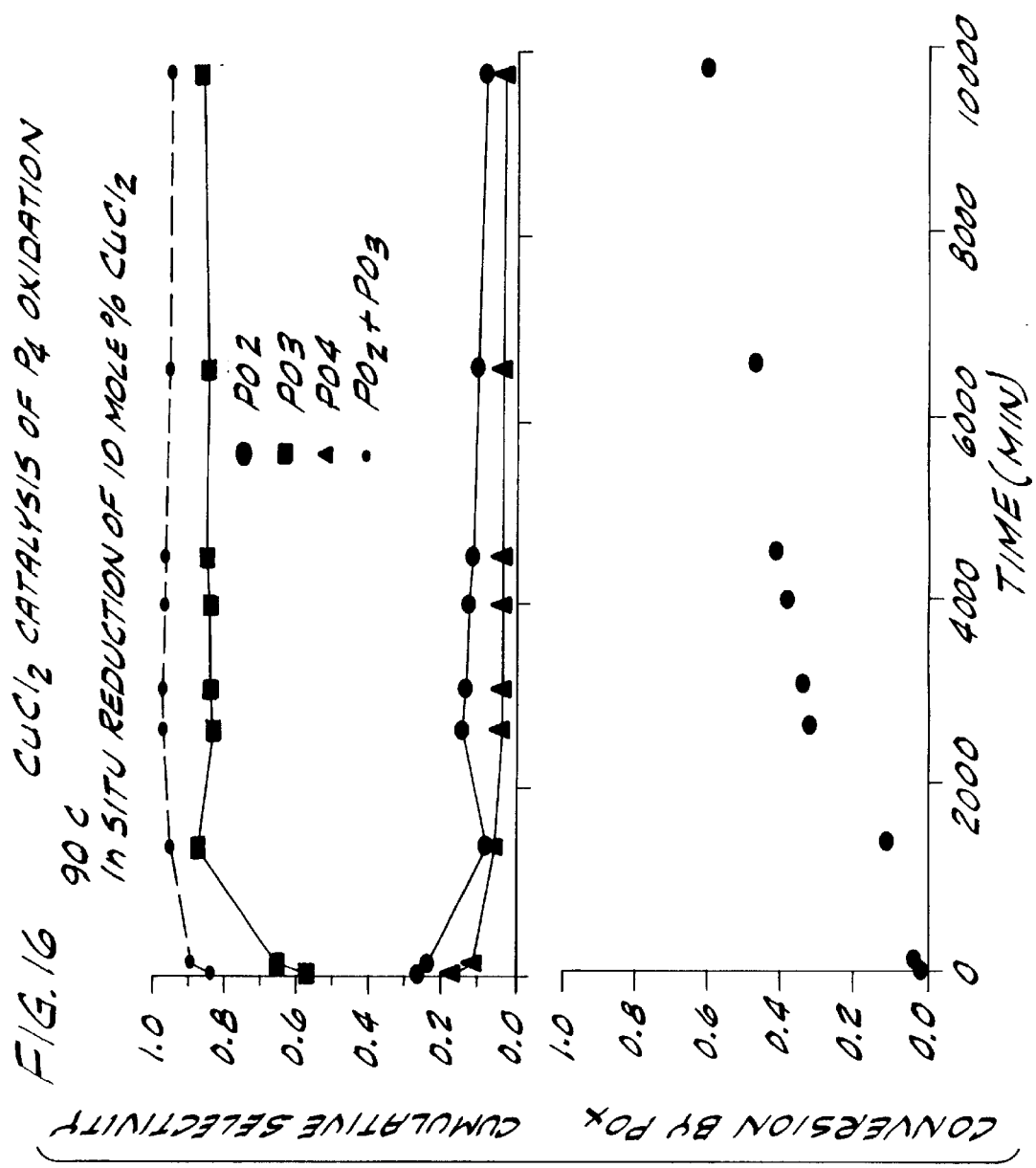
FIG. 16 presents plots of cumulative selectivity and yield vs. time for catalytic oxidations of tetraphosphorus with water at 90° C. using a $CuCl_2$ hydrate catalyst that is reduced in situ by tetraphosphorus.

In carrying out the run of Example 31, a saturated solution of copper chloride was prepared and mixed with molten tetraphosphorus at 65° C., at which point an incipient reduction of the copper salt occurred with substantial incorporation of the copper into the phosphorus phase. After one hour the water phase had substantially disappeared, resulting in the formation of a black/green liquid mass containing chunks of black appearing material. The catalyst/phosphorus mixture was then treated as described above. During the early stages of the reaction, a silvery pool of phosphorus+catalyst was formed under moderate agitation at the bottom of the reactor. After a lengthy period, this pool broke up into what appeared to be a black powder or sand. FIG. 16 contains plots of selectivity of the $PO_x$ species and the conversion vs. time. The data reported in Table 2 were based on a sample taken after approximately 7.86 days.

The reaction of Example 32 was carried out in the same manner as Example 31 except that the reaction temperature was 107° C. The catalyst/phosphorus mixture appeared to undergo substantially the same transformations described above in the case of Example 31, except that the "black sand" stage was reached much earlier in the reaction of Example 32 than in the reaction of Example 31. The analytical data presented in Table 2 for Example 32 were based on a sample taken after 504 minutes of reaction. Thus, the reaction of Example 32 proceeded at a highly productive rate.

Example 33 was performed similarly to Example 31 in that palladium black was initially admixed with the phosphorus phase followed by addition of a saturated solution of copper chloride hydrate.

EXAMPLE 35

Figure 14:
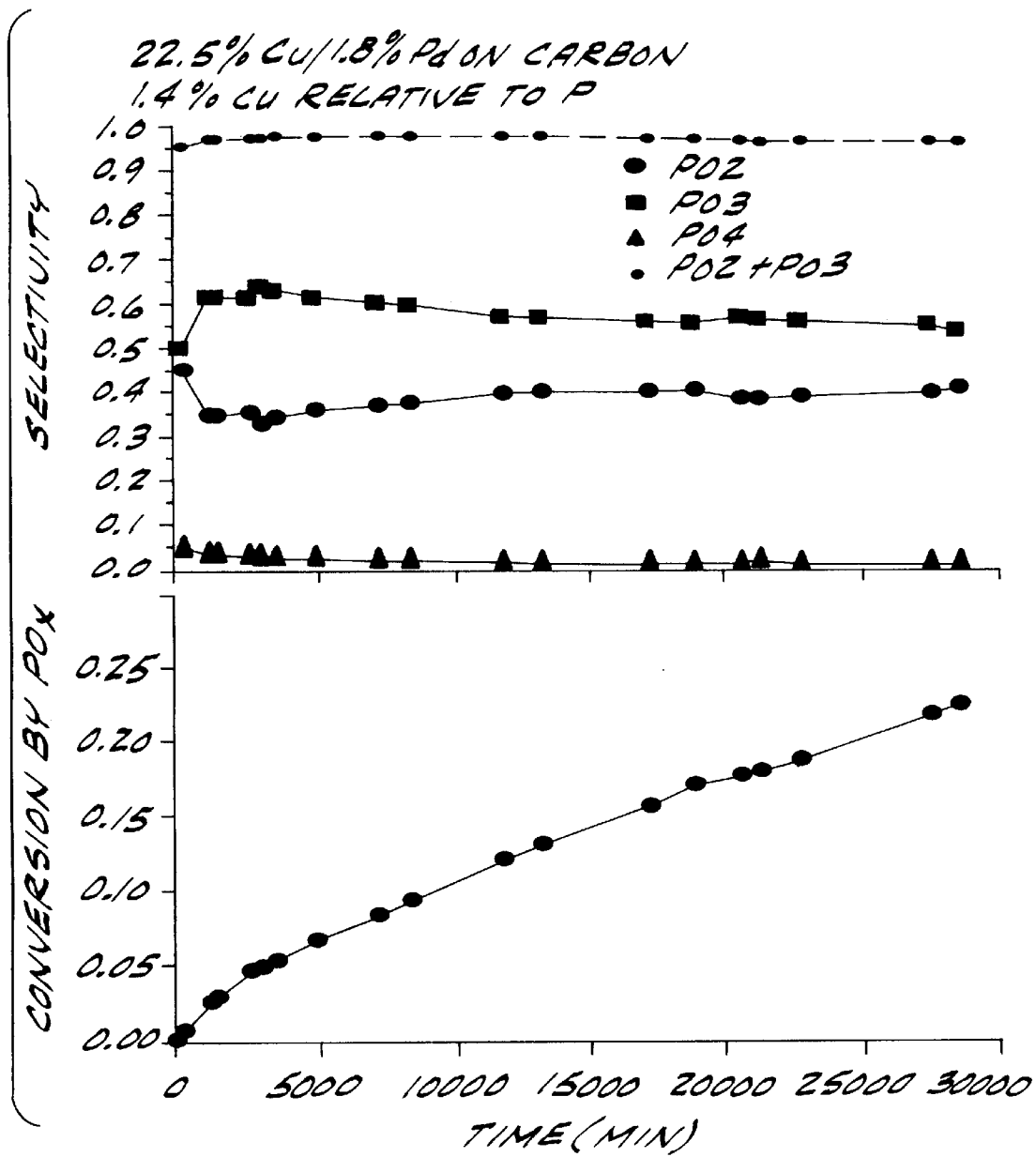
FIG. 14 presents plots of both selectivity and yield vs. time in the catalytic oxidation of tetraphosphorus with water at 90° C. using a 22.5% Cu/1.8% Pd on carbon catalyst at a catalyst loading of 1.4 mole % Cu based on phosphorus atoms.

In a further experiment, $P_4$ was oxidized by reaction with water at 90° C. in the presence of 1.4 mole % (basis $P_4$) of the catalyst comprising 22.5% Cu/1.8% Pd carbon. The reaction temperature, reactor pressure, instantaneous selectivity, and cumulative selectivity for the reaction of this example are set forth in FIG. 14. A sustained selectivity to P(I)+P(III) was realized, with particularly high proportions of hypophosphorous acid in the reaction product.

EXAMPLE 36

Figure 15:
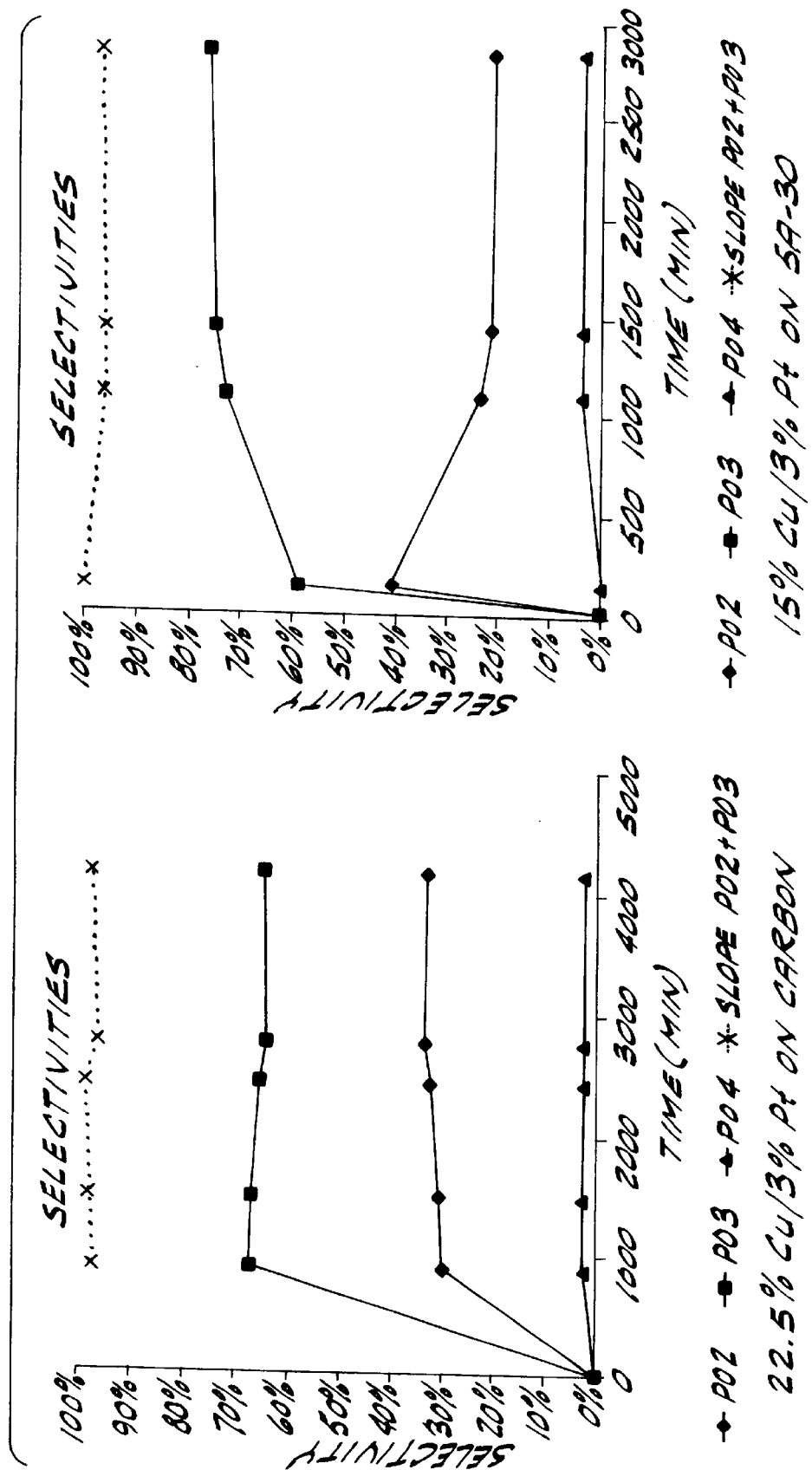
FIG. 15 presents two plots comparing the selectivity vs. time data of FIG. 14 with selectivity vs. time data for a reaction run otherwise under the conditions of FIG. 14 but using a catalyst comprising 15% Cu/3% Pt on a carbon support similar to that of the FIG. 14 catalyst.

Two supported copper catalysts were compared with respect to their effectiveness in the catalytic oxidation of tetraphosphorus with liquid water. Catalysts tested were 22.5% Cu/3% Pt on carbon and 15% Cu/3% Pt on carbon SA-30. The reactions were carried out substantially according to the protocol of Example 4 at a catalyst loading of 2 mole % Cu and a temperature of 90° C. Each catalyst gave a conversion of about 11% after 2700 minutes. Set forth in FIG. 15 are plots comparing the selectivity vs. time data for the two catalysts. As indicated, the 22% Cu/3% Pt on carbon catalyst exhibited a steady 98% [P(I)+P(III)] selectivity with the specific selectivities for P(I) and P(III) remaining constant as a function of time. The SA-30 supported catalyst showed a constant [P(I)+(III)] selectivity of 97%, but the selectivity to P(III) species increased and the selectivity to P(I) species declined as a function of time. The decline in P(I) selectivity may have resulted from barriers to transport of P(I) acid from the $P_4$ phase to the aqueous phase resulting from the higher viscosity of the phosphorus pool in the SA-30 supported catalyst experiment. Because this catalyst had a lower Cu loading, a higher weight fraction of catalyst was needed to provide the same molar concentration of Cu. Since the catalyst is concentrated in the phosphorus phase, the higher solids concentration may have contributed to a higher phosphorus phase viscosity and thus to a barrier to mass transfer.

EXAMPLE 37

Studies were conducted to determine the effect of temperature on oxidations of phosphorus by catalytic reaction with water. The reactions were conducted in a 300 cc autoclave at a constant stir rate of 1000 rpm.

The catalyst used was 22.5% Cu/1.8% Pd on a carbon support.

Figure 17:
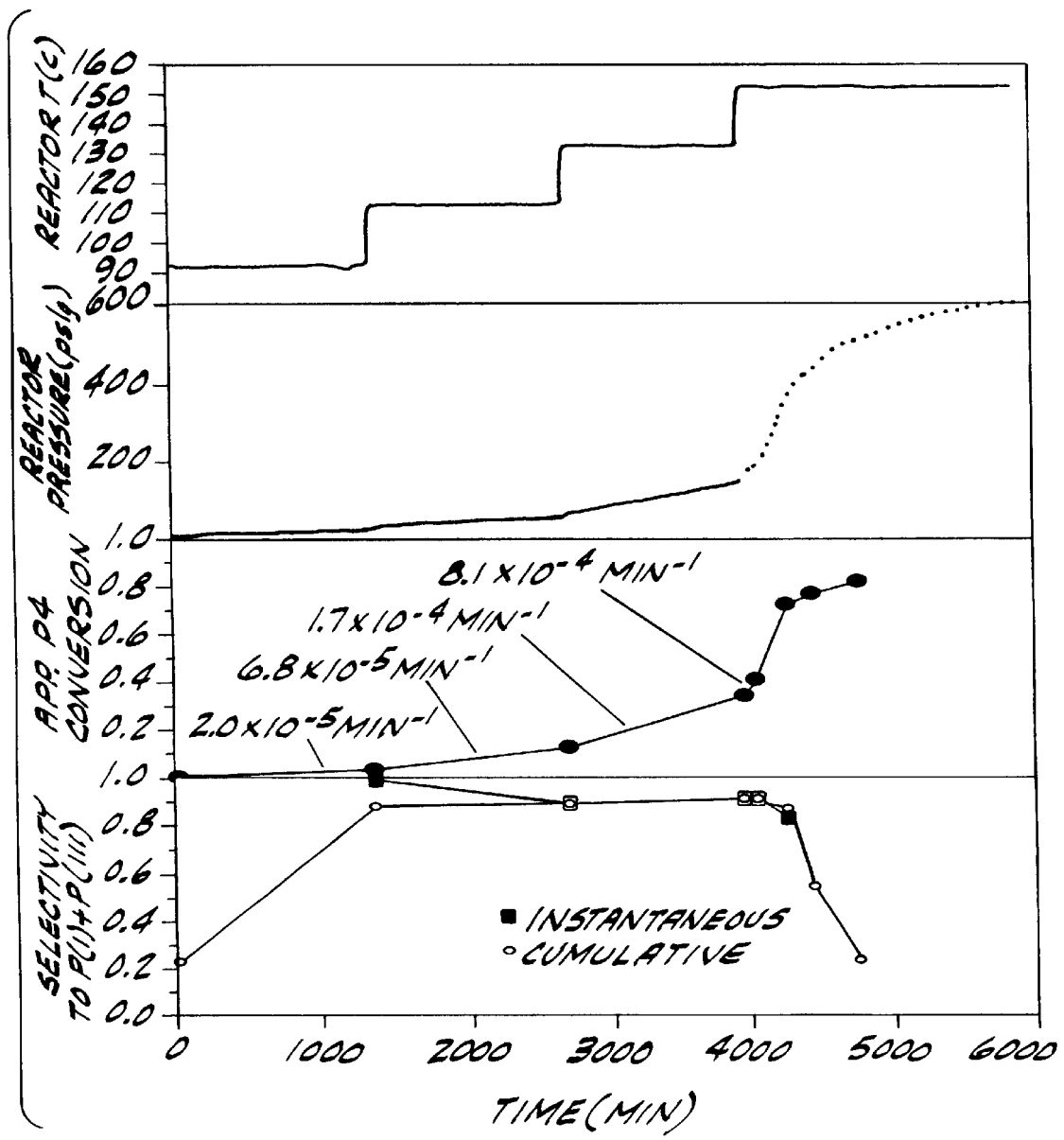
FIG. 17 presents plots of temperature, rate of $P_4$ conversion and selectivity vs. time for experiments conducted to determine the effect of temperature on productivity and selectivity using 22.5% Cu/1.8% Pd on carbon at a catalyst loading of 1.8 mole % Cu based on phosphorus atoms.

Catalyst loading was 1.8 mole %. The reaction temperature was systematically raised in 20° C. increments from an initial temperature of 90° C. to a final temperature of 150° C. Reactor pressure was monitored continuously, and liquid samples were withdrawn at the end of each temperature stage. FIG. 17 is a plot of temperature, rate of $P_4$ conversion and selectivity vs. time for the reactions of this Example. A conversion of 82% was determined from the $PO_x$ species produced by the end of the temperature study. As exemplified by the progressive increase in reactor pressure, during the reaction, the oxidation exhibited the expected zero order behavior over most of the reaction. However, it may be seen that, early in the 150° C. phase, the rate sharply increased and the reaction shifted to more of a first order profile. This phenomenon may have been attributable to redispersion of the catalyst so that active sites of the catalyst were in significant contact with the aqueous phase. In fact, the catalyst may have started to come off the support. Alternatively, loss of selectivity may have resulted from catalytic activity of the autoclave walls and internals (agitator, coil, etc.) at temperatures above 150° C. The presence of phosphine was also detected in the reactor at temperatures above 150° C. In any event, a significant decrease in selectivity accompanied the increased reaction rate about 150° C.

Figure 18:
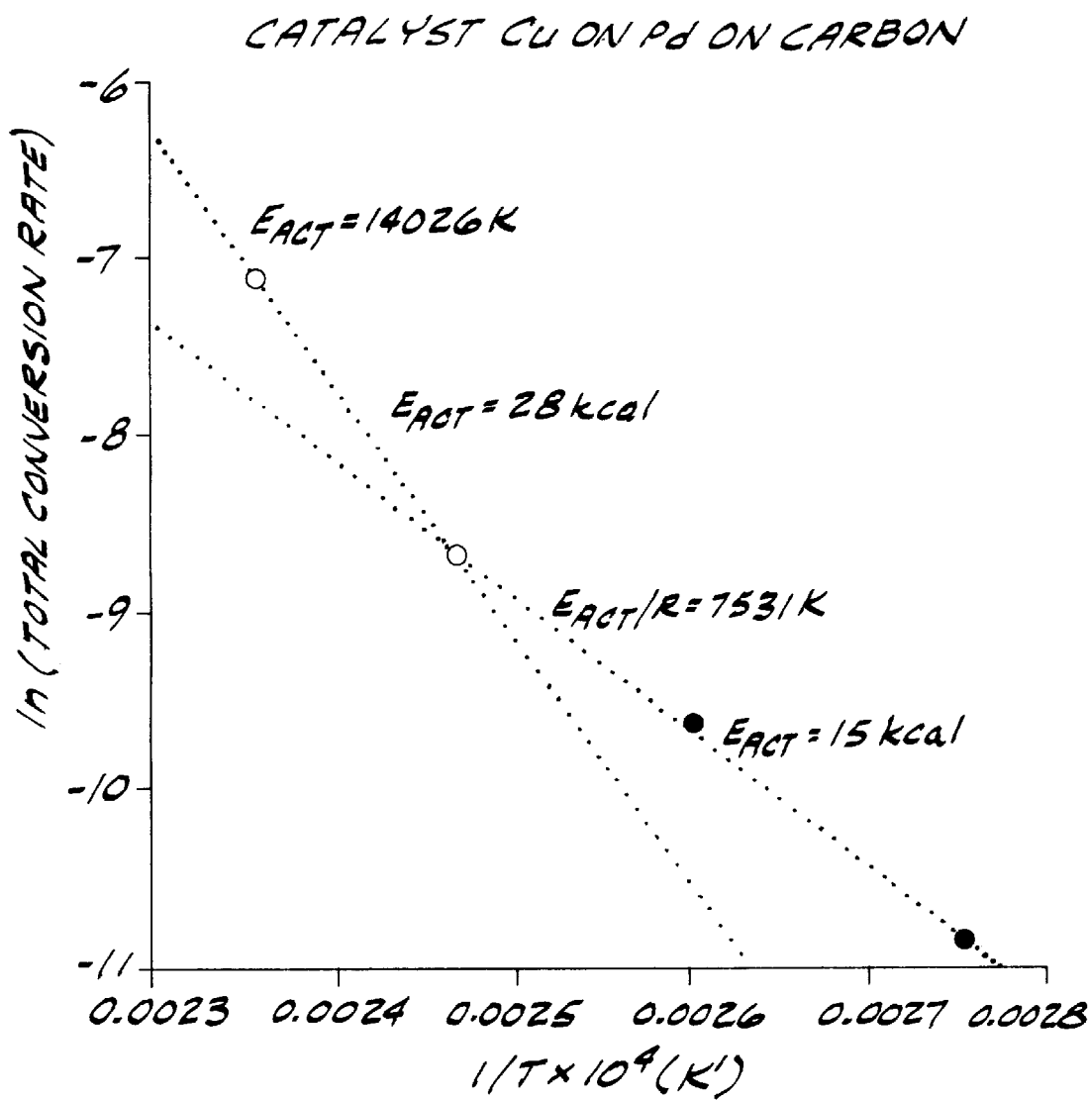
FIG. 18 plots ln(conversion rate) vs. reciprocal temperature for the reactions illustrated in FIG. 17.

The rate constant for consumption of $P_4$ was computed at several temperatures. FIG. 18 is a plot of $\ln(P_4$ conversion rate) vs. reciprocal temperature. The first three data points show a reasonably consistent log plot of the apparent zero order rate constant, the slope of this plot yielding an activation energy of 15 kcal. in the range of 90° C. to 130° C. However, a sharp increase in activation energy appears at about 150° C.

Figure 19:
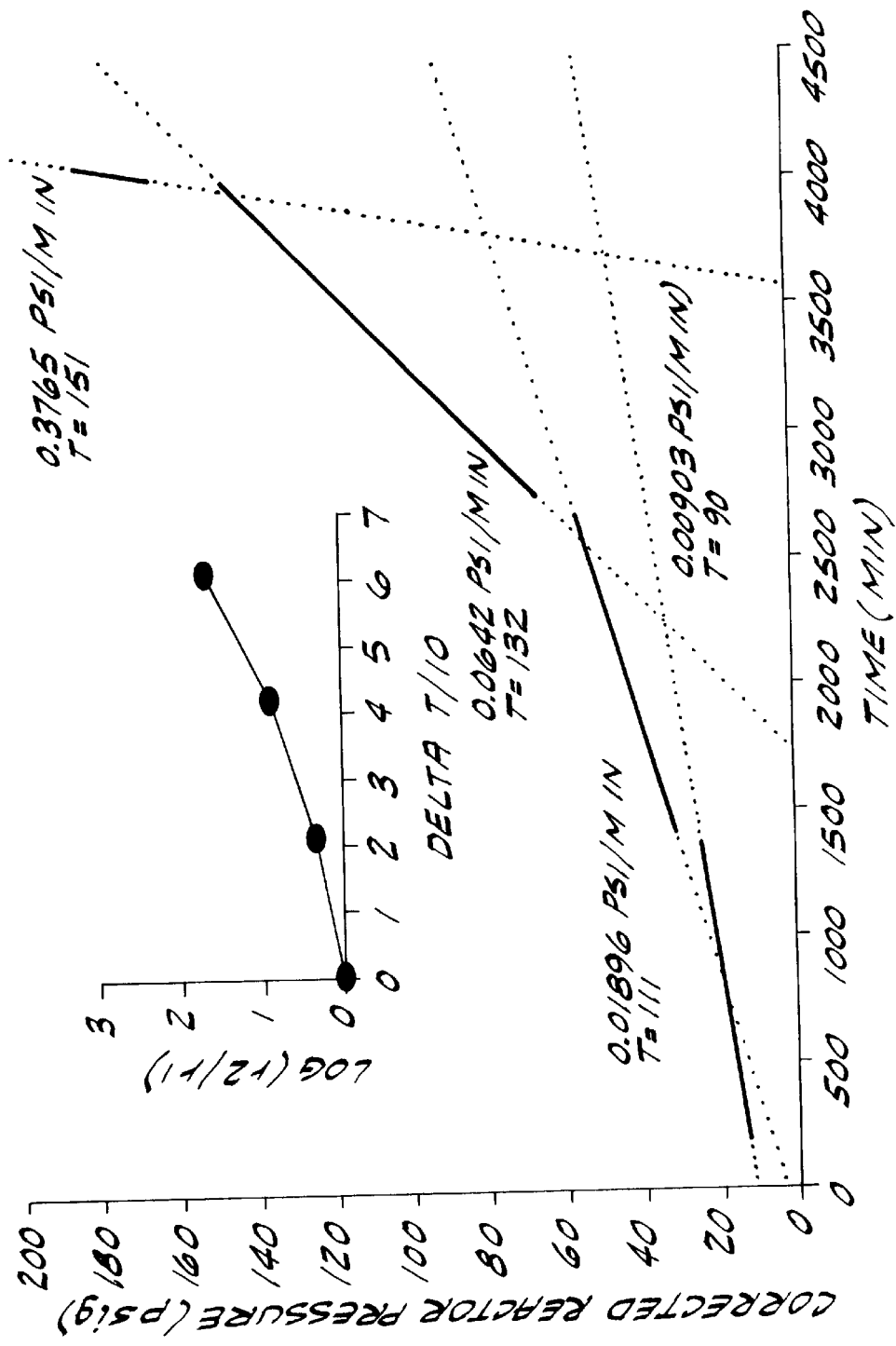
FIG. 19 plots corrected reaction pressure vs. time for the reactions illustrated in FIG. 17, the inset in FIG. 19 constituting a plot of the log($r_1/r_2$) vs. one tenth of the increase from the starting temperature wherein $r_1$ is the rate of oxidation of $P_4$ at the starting temperature and $r_2$ is the rate of oxidation at the temperature determined from the temperature increase value indicated on the abscissa.

FIG. 19 is a plot of the rate of pressure increase in the reactor as a function of time, after removing temperature change transients and adjusting for head-space volume increases due to sampling. Only the initial portion of the 150° C. region appears in FIG. 19. The pressure build remains strikingly zero order, but there is an unexpected exponential increase in the apparent rate of pressure build. The inset in FIG. 19 reflects the increase in reaction rate as a function of temperature, as expressed by the base 10 logarithm of the ratio of $r_{1/2}$ vs. $\Delta T \times 10^{-1}$, where $r_1$=the phosphorus oxidation reaction rate at the starting temperature, $\Delta T$=the increase in temperature from the starting temperature, and $r_2$=the phosphorus oxidation rate at the temperature corresponding to the starting temperature+$\Delta T$.

EXAMPLE 38

Figure 20:
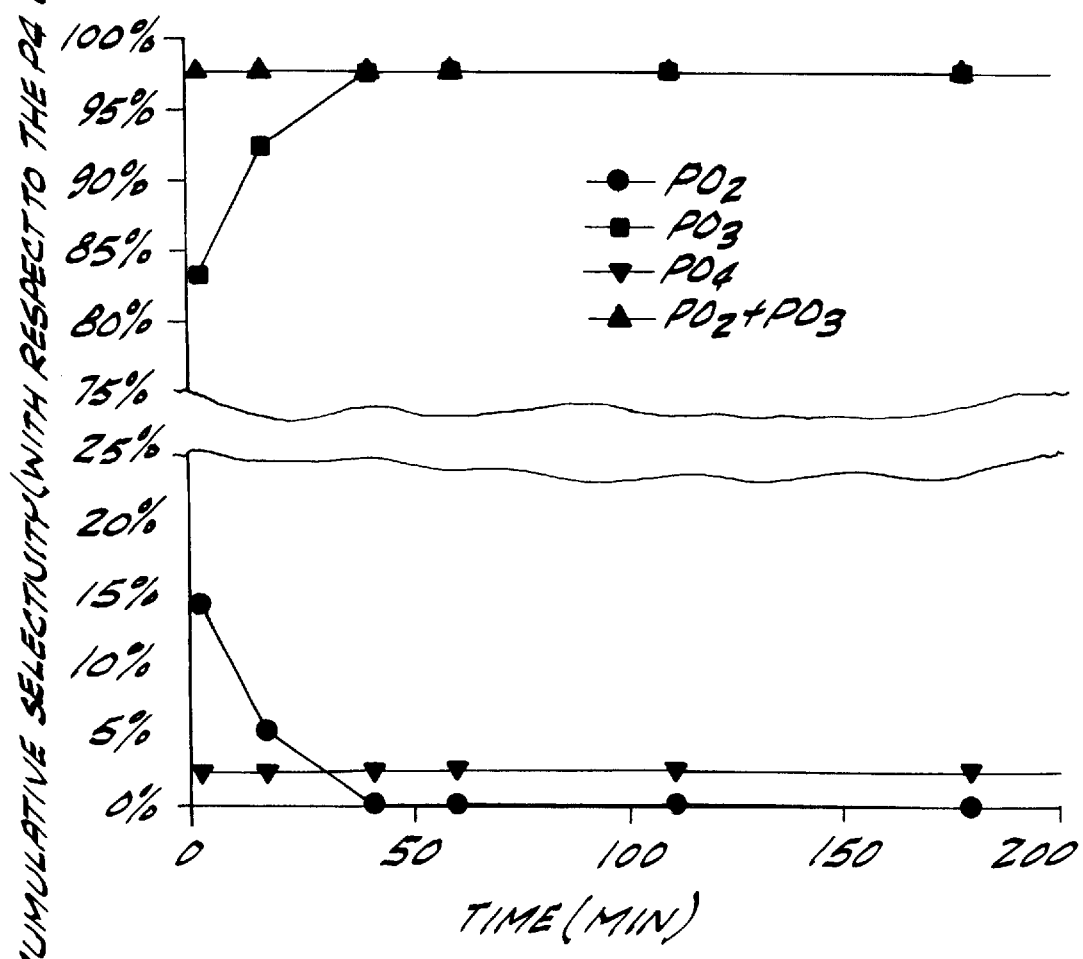
FIG. 20 plots cumulative selectivity and point-wise as a function of time in a finishing reaction for conversion of hypophosphorous acid to phosphorous acid by catalytic aqueous phase oxidation with water using Pd as a catalyst.

A tetraphosphorus oxidation reaction was conducted substantially in the manner described in Example 25. By use of a syringe, the aqueous phase from this reaction mixture containing significant proportions of hypophosphorous acid was removed from the reaction vessel and transferred to a separate flask that had been charged with Pd black in a proportion of about 4 mole % based on the hydrophosphorous acid substrate in the transferred aqueous phase. The resulting mixture was heated to 65° C. and the contents were analyzed by ion chromatography at appropriate time intervals. As illustrated in FIG. 20, the data showed complete conversion of $H_3PO_2$ to $H_3PO_3$ within 40 minutes, and a sustained selectivity to P(I)+P(III) acids of 97+% over a period of more than 3 hours, even after all P(I) acid had been consumed. As may further be noted from FIG. 20, the concentration of P(V) acid remained substantially unchanged during the oxidation of hypophosphorous acid to phosphorous acid. Selectivity did not begin to deteriorate until the reaction mixture had been held at 65° C. for more than 19 hours.

EXAMPLE 39

Figure 21:
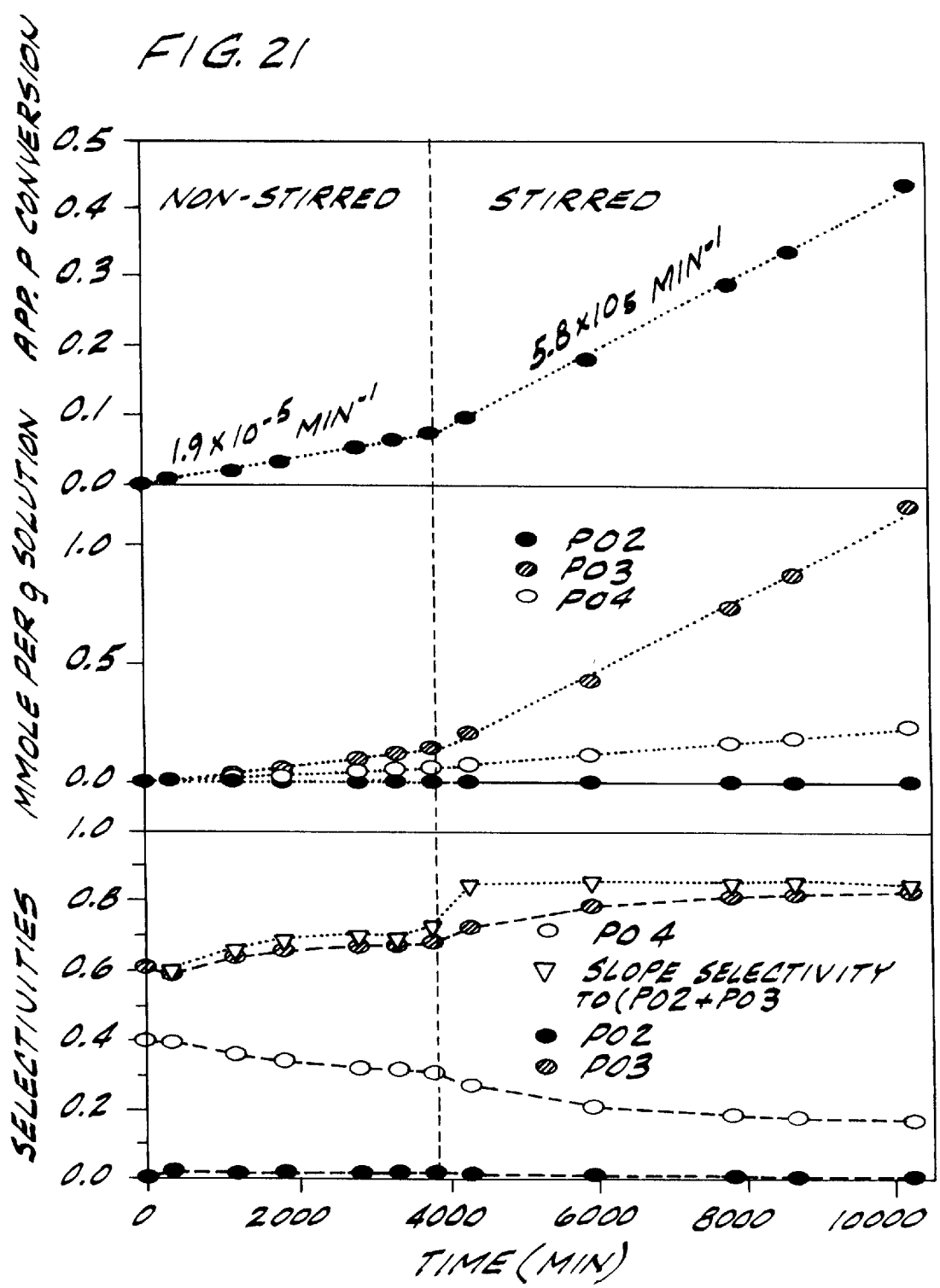
FIG. 21 presents plots of $P_4$ conversion, cumulative concentrations of P(I), P(III) and P(V) species in the aqueous phase, and cumulative selectivities in the oxidation of tetraphosphorus by catalytic reaction with water under initial non-agitated and subsequently agitated conditions.
Figure 22:
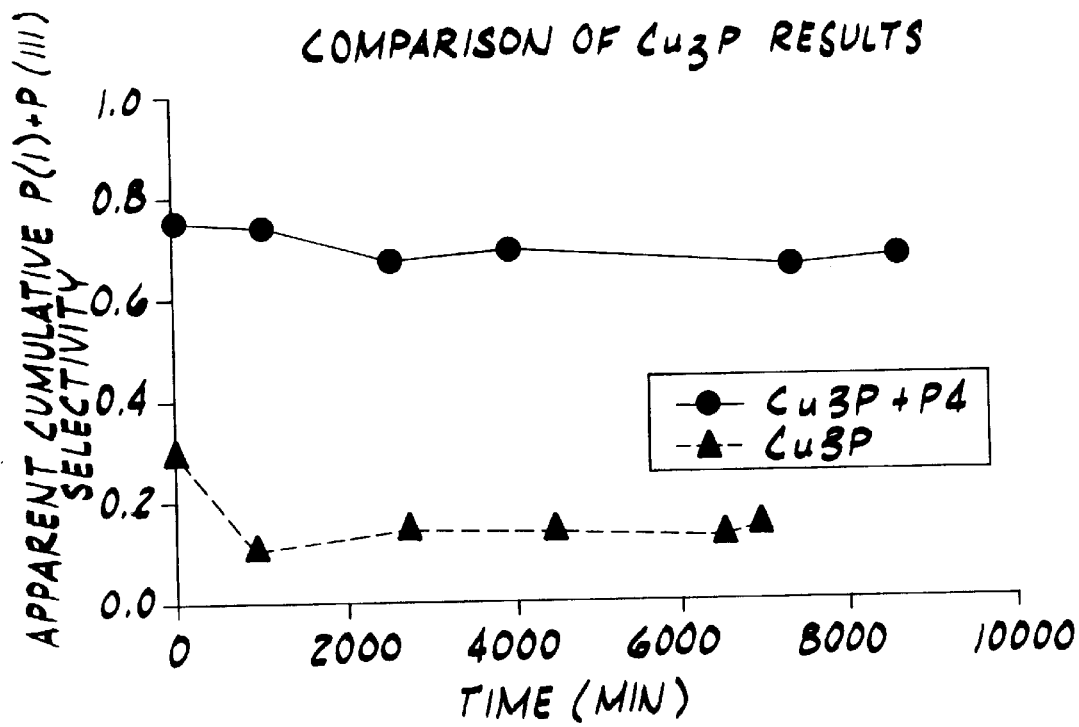
FIG. 22 contains plots of P(I)+P(III) selectivity vs. time for two separate reaction conditions, one produced by agitating a mixture of copper (I) phosphide and water at 90° C. in the presence of $P_4$, the other produced under similar conditions but in the absence of $P_4$.
Figure 23:
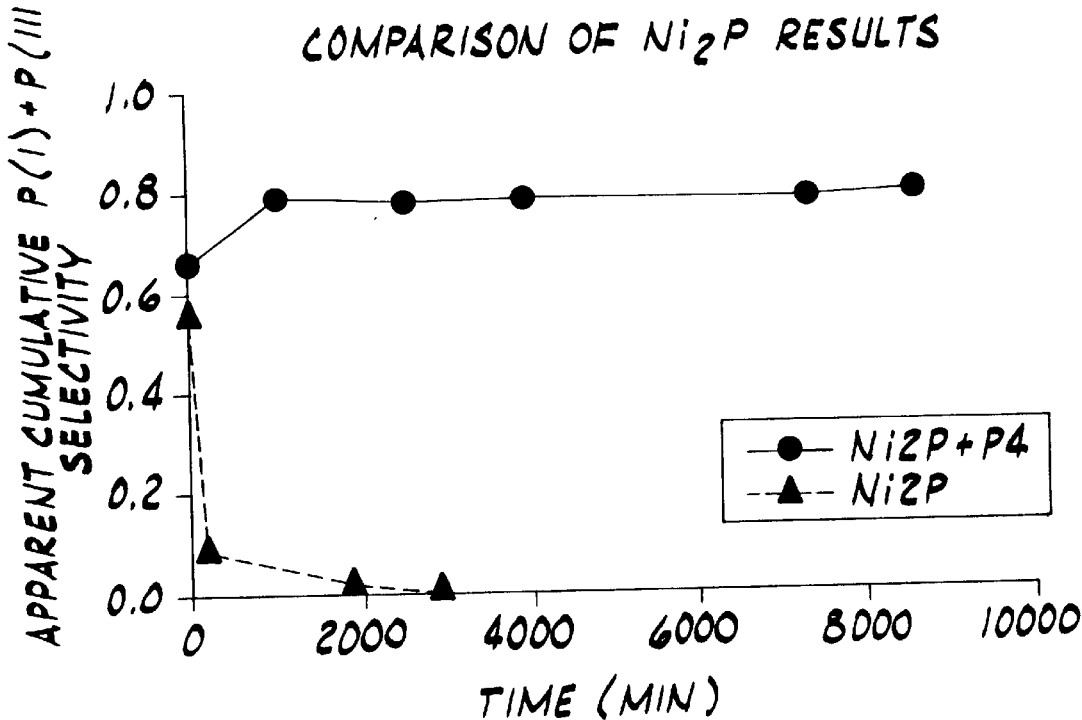
FIG. 23 contains plots generated in substantially the same manner as those of FIG. 22 but using nickel phosphide instead of copper phosphide in the reactions.

To explore the effect of agitation in a heterogeneous reaction system comprising a phosphorous pool in contact with a supernatant aqueous phase, a reaction was conducted initially in a quiescent condition and continued under conditions of moderate agitation. Tetraphosphorus (3.91 g) and Pd black (6 mole % based on phosphorus atoms) were charged to a long cylindrical approximately 1" diameter Schlenck flask along with about 50 ml water. The flask was equipped with a nitrogen blanket and a stir bar. A magnet was also attached to the exterior wall at the top of the flask so that the internal stir bar could be suspended at the top of the flask during the experiment. For the non-stirred portion of the experiment, prior to sampling the water phase, the stir bar was dropped into the phosphorus pool and stirred for two minutes to assure efficient extraction of the phosphorus phase so a representative sample could be obtained. During an initial reaction period of 4000 minutes, the reaction was carried out under essentially quiescent conditions, i.e., without continuous stirring. At 4000 minutes, the stir bar was activated and the reacting mixture subjected to moderate agitation during the remainder of the reaction period. Agitation was sufficient to promote mass transfer between the phosphorus and aqueous phases, but not vigorous enough to cause either phase to be dispersed in the other, or for the catalyst to be transferred from the phosphorus phase to the aqueous phase. The $P_4$ conversion, cumulative concentrations of P(I), P(III) and P(V) species in the aqueous phase, and cumulative selectivities for the reaction of this Example are plotted in FIG. 21. It may be seen that imposition of moderate agitation increased the reaction rate approximately 3× as compared to reaction under quiescent conditions. An immediate and significant increase in selectivity to P(I)+P(III) oxyacids was also observed when agitation was applied. The results of this Example suggest that attainment of maximum selectivity is dependent in part on adequate rates of mass transfer of phosphorus oxyacid reaction product from the phosphorus phase, where the reaction product is in contact with the catalyst, to the aqueous phase which is substantially out of contact with active catalyst sites under moderate agitation conditions.

EXAMPLE 40

A glass sleeve plated with silver using Tollen's Reagent was placed into a 300 mL Hastelloy C autoclave equipped with a disperamax impeller and fitted with Hastelloy C internals. The autoclave was then charged with water (85.2 g) and phosphorus (28.13 g; 0.91 moles P atoms) and the resulting mixture was heated to 200° C. with vigorous agitation. After 1.7 hours, the water phase was analyzed by IC and determined to contain 0.0% $H_3PO_2$, 11.1% $H_3PO_3$, and 6.5% $H_3PO_4$. Selectivity to P(I)+P(III) was 63%.

EXAMPLE 41

Tetraphosphorus (1.094 g; 0.0353 moles P atoms) was melted in a test tube in a glove box. Carbon supported catalyst (0.14 g) comprising 17.5% Cu/3% Pd on SA-30 was added and mixed into the molten phosphorus (1 mole % Cu relative to P atoms). The mixture was allowed to cool and solidify, and was then transferred to a flask containing degassed water (47.4 g). This flask was then immersed in a sonicating water bath (Bransonic Model 5210, 47 MHz) and heated to 61° C. As soon as the $P_4$ phase had melted, the sonication was turned on and maintained for a period of 75 minutes. The inititally clear aqueous phase of this reaction mixture became gradually cloudy during the sonication, although a molten $P_4$/catalyst phase remained at the bottom of the flask. The reaction was sampled two times during this period. Analysis of the second sample, obtained at the end of the initial 75 minute sonication, indicated 0.12% conversion of the phosphorus with 100% selectivity to P(I)+P(III). The apparent $P_4$ conversion rate was $1.6 \times 10^{-5}$ min$^{-1}$, which is similar to the rate observed for the same catalyst and catalyst concentration in a previous run at 90° C. without sonication (see Example 25, Table 2). The reactor was then stirred gently with a stir bar for a period of 120 minutes, still in the heated water bath but without sonication. A sample obtained at the end of this "silent" reaction period indicated no additional $P_4$ conversion. At this point the sonication was restarted and allowed to continue for another 120 minutes. A sample obtained from the reactor at the end of this second sonication treatment indicated a final $P_4$ conversion of 0.4%, again with 100% yield of P(I)+P(III). Conversion rate during the second sonication period was similar to that observed in the first sonication treatment.

Run conditions and sample analyses of this Example are set forth in Table 3. Cumulative Selectivities, Slope Selectivity, Apparent $P_4$ Conversion, Zero Order Rate, and Normed Rate are set forth in Table 4. Plots of sample concentrations, conversion, reaction rate and selectivity vs. run time are set forth in FIGS. 25, 26, 27 and 28, respectively.

TABLE 3

Conditions - 17.5% Cu/3% Pd/carbon ~60° C. Sonicator Bath

| | $H_2O$ | $P_4$ | $H_3PO_2$ | $H_3PO_3$ | $H_3PO_4$ | Catalyst | g cat metal/g P |
|---|---|---|---|---|---|---|---|
| Charges (g) | 47.35 | 1.094 | 0 | 0 | 0 | 0.14 | 0.02239488 |

| | | | | Sample Concentration Wt % | | |
|---|---|---|---|---|---|---|
| | Run Time | T | Reactor P | | | |
| Sample # | (min) | (C) | (psig) | $PO_2$ | $PO_3$ | $PO_4$ |
| (pre-run) 1 | | | — | | | |
| 2 | 1.0 | 60 | — | 0.000 | 0.000 | 0.000 |
| 3 | 20.0 | 60 | — | 0.001 | 0.000 | 0.000 |
| 4 | 75.0 | 60 | — | 0.003 | 0.004 | 0.000 |
| 5 | 187.0 | 60 | — | 0.003 | 0.003 | 0.000 |
| 6 | 312.0 | 60 | — | 0.012 | 0.010 | 0.000 |

EXAMPLES 42–44

Using the method of Examples 15–34, a series of reactions was conducted in which tetraphosphorus was oxidized by catalytic reaction with water. The results of these reaction runs are set forth in Table 5.

EXAMPLES 45

A mixture of phosphorus and $CuMoO_4$ catalyst was prepared substantially in the manner described for Examples 15–34. This mixture was transferred to a 300 mL Ace Glass reactor provided with a magnetic stir bar, and fitted with an internal thermocouple, pressure gauge, a block valve (for purge and pressure release) and an internal frit connected to a sample line/valve assembly used to sample the reactor and monitor the progress of the reaction. Reaction was conducted at a temperature maintained at 130° C. For the reaction of this Example, the aqueous phase remained blue/black for the duration of the experiment. This coloration persisted even after filtration. The dark blue species are believed to be partially reduced molybdic oxide species containing both oxide and hydroxide functionality. Analysis of the reaction mixture is tabulated in Table 5.

EXAMPLES 46–50

A series of catalyst/phosphorus mixtures was prepared in the manner described for Examples 15–34. This mixture was charged to the apparatus described in Example 45 and a phosphorus oxidation reaction conducted in the manner described in the latter example. Analysis of the reaction mixture is tabulated in Table 5.

EXAMPLE 51

A catalyst/phosphorus mixture was prepared in the manner described for Examples 15–34. The catalyst was 17.5% Cu on a 3% Pd/SA-30 support. The reaction was conducted generally in the manner described for Examples 15–34, but the internal reaction temperature was maintained at 130° C. Analysis of the reaction mixture is set forth in Table 5.

EXAMPLE 52

A catalyst/phosphorus mixture was prepared in the manner described in Example 51. Using the apparatus described in Example 45, oxidation of tetraphosphorus by catalytic reaction with water was carried out generally in the manner described in the latter example, except that the internal reaction temperature was maintained at 150° C.

TABLE 4

| | Cumulative Selectivities | | | Slope Selectivity | Apparent $P_4$ conversion | Zero Order Rate (Min $^{-1}$) | | Normed Rate mole P/mole metal/min | |
|---|---|---|---|---|---|---|---|---|---|
| | | | | $PO_2$ + $PO_3$ | | From t = 0 | From Last Point | From t = 0 | From Last Point |
| Sample # | $PO_2$ | $PO_3$ | $PO_4$ | | sion | | | | |
| (pre-run) 1 | | | | | | | | | |
| 2 | | | | | 0.000% | 0.00E+00 | — | 0.00E+00 | — |
| 3 | 0.001 | 0.000 | 0.000 | 1.000 | 0.029% | 1.45E−05 | 1.53E−05 | 1.32E−03 | 1.39E−03 |
| 4 | 0.534 | 0.466 | 0.000 | 1.000 | 0.122% | 1.63E−05 | 1.69E−05 | 1.48E−03 | 1.54E−03 |
| 5 | 0.556 | 0.444 | 0.000 | 1.000 | 0.110% | 5.89E−06 | −1.07E−06 | 5.35E−04 | −9.75E−05 |
| 6 | 0.595 | 0.405 | 0.000 | 1.000 | 0.405% | 1.30E−05 | 2.36E−05 | 1.18E−03 | 2.14E−03 |

TABLE 5

| Ex. | Catalyst | Mole % Cat. (based on P atoms) | % Yield PO2 | % Yield PO3 | % Yield PO4 | P(I) + P(III) Selectivity |
|---|---|---|---|---|---|---|
| 42* | AuCl3 | 2 | 0.74 | 1.44 | 0.93 | 72 |
| 43* | Cu(3,5-diisopropyl salicilate)2 | 2 | 0.25 | 0.84 | 0.52 | 92 |
| 44* | CuMoO4 | 2 | 4.3 | 6.6 | 1.21 | 97 |
| 45* | CuMoO4 | 10 | 2.9 | 25.2 | 11.8 | 71 |
| 46* | CuWO4 | 2 | 2 | 4.7 | 0.5 | 96 |
| 47* | Ag8(WO)4 | 2 | 0.87 | 4.2 | 3.9 | 73 |
| 48* | Cu(SO)4 | 2 | 2.2 | 11.3 | 2.8 | 95 |
| 49* | K2MoO4 | 2 | 0.12 | 0.27 | 0.22 | 62 |
| 50 | 3Na2WO4.9WO3 × H2O | 2 | 0.056 | 0.22 | 0.22 | 55 |
| 51 | 17.5% Cu/3% Pd on SA-29 | 1.2 | 17.3 | 16.4 | 0.94 | 98 |
| 52** | 17.5% Cu/3% Pd on SA-30 | 2 | 4.3 | 7.2 | 1.3 | 70–97** |

*Catalyst was dissolved in a minimum amount of water before being added to molten P4.
** Selectivity increased to 97% and after ~10% conversion selectivity sharply dropped to 73.

EXAMPLES 53–114

Two general procedures were used for the catalytic oxidation of tetraphosphorus by reaction with water in the presence of a coordination catalyst.

In Procedure A, a portion of tetraphosphorus (1 g) was cut from a 10 g tetraphosphorus ingot under water and transferred to a tared jar filled with water. The $P_4$ sample was weighed in the tared jar and transferred to an Ar filled glove box. In the glove box, the $P_4$ sample was removed from the jar, placed in an 18×150 mm test tube and heated to melting with a temperature controlled oil bath. Solid catalyst was added to the molten $P_4$ in portions accompanied by thorough mixing. When catalyst addition was completed, the $P_4$/catalyst mixture was cooled until it became solid and the test tube was capped and removed from the glove box. The $P_4$/catalyst mixture was then removed from the test tube under water and transferred to a 50 mL round bottom flask charged with deionized water (50 mL) and provided with a teflon stir bar. The flask was fitted with an in-line septum-inlet adapter attached to a nitrogen bubbler and fitted with a rubber septum. The water/catalyst/$P_4$ charge mixture was stirred and heated to reaction temperature typically 90° C. using a temperature controlled oil bath. Samples were periodically taken from the aqueous phase of the reaction mixture using an Ar purged disposable syringe equipped with a 0.2 μm nylon filter. Samples of the aqueous reaction product were tested for pH using colorpHast® pH 0–14 pH indicator strips obtained from EM Science, Gibbstown, N. J. 08027, and tested for concentrations of phosphorus oxyacids by ion chromatography.

Procedure B was substantially identical to Procedure A except that the $P_4$ sample was removed from the tared jar in the glove box and placed directly in a 50 mL round bottom flask and heated to melting in the temperature controlled bath. Solid catalyst was then added in portions to the molten $P_4$ in the 50 mL flask, accompanied by thorough mixing. When catalyst addition was completed, the $P_4$/catalyst mixture was cooled until solid after which water (50 mL) sparged with Ar was added to the flask and the flask was capped with a rubber septum and removed from the glove box. Reaction sample analysis then proceeded as in Procedure A.

Results of the experimental reactions of Examples 53–114 are set forth in Table 6.

The legend for ligands of the coordination catalyst used in the runs of this Example are set forth below.

acac=acetylacetonate, [$CH_3C(O)CHC(O)CH_3$]
$PPh_3$=triphenylphosphine, $P(C_6H_5)_3$
$PEt_3$=triethylphosphine, $P(C_2H_5)_3$
dppe=1,2-bis(diphenylphosphino)ethane, $(C_6H_5)_2PCH_2CH_2P(C_6H_5)_2$
Cp=cyclopentadienyl, [$C_5H_5$]
nbd=norbornadiene
cod=cis, cis-1,5-cyclooctadiene
bipy=2,2'-bipyridyl
DMSO=dimethylsulfoxide

TABLE 6

| Ex. # | Procedure | Catalyst | Mole % metal | Run T (C) | Final Conv. by POx (%) | Conv. Rate (min −1) | Turnover # | Ave. Slope Select to (PI + PIII) | Average Normalized Rate mole P/Mole M/min | Cumulative Selectivity to (PI + PII) |
|---|---|---|---|---|---|---|---|---|---|---|
| 53 | A | Cu(II) (acac)2 | 2.00 | 90 | 3.50 | 5.66E−06 | 1.75 | 93.3 | 3.59E−04 | 88.30 |
| 54 | A | Pd2(dibenzylideneacetone) | 2.00 | 90 | 12.20 | 3.14E−05 | 6.09 | 82.3 | 1.57E−03 | 82.50 |
| 55 | A | PdCl2(PPh3)2 | 2.00 | 90 | 3.50 | 7.62E−06 | 1.75 | 88.0 | 3.80E−04 | 89.60 |
| 56 | A | Cp2Fe | 2.0 | 90 | 0.20 | 5.69E−07 | 0.10 | 37.6 | 2.85E−05 | 45.90 |
| 57 | A | Co(acac)2 | 2.02 | 90 | 5.50 | 1.88E−05 | 2.72 | 86.1 | 7.06E−04 | 87.50 |
| 58 | A | [CpMo(CO)3]2 | 2.01 | 90 | 1.10 | 1.82E−06 | 0.55 | 48.0 | 9.06E−05 | 40.30 |
| 59 | A | [(nbd)RhCl]2 | 2.02 | 90 | 23.30 | 6.67E−05 | 11.50 | 86.8 | 3.26E−03 | 82.00 |
| 60 | A | W(CO)6 | 2.04 | 90 | 0.80 | 2.0SE−06 | 0.39 | 51.8 | 1.01E−04 | 48.60 |
| 61 | A | NiCl2(dimethoxyethane) | 2.00 | 90 | 7.20 | 1.79E−05 | 3.60 | 80.3 | 8.94E−04 | 84.70 |
| 62 | A | RUCl2(bipy)2 2H2O | 2.00 | 90 | 2.50 | 7.12E−06 | 1.25 | 88.5 | 3.57E−04 | 87.80 |
| 63 | A | 5,10,15,20-tetraphenyl-21H,23H-porphine Co(II) | 2.02 | 90 | 0.50 | 1.50E−06 | 0.25 | 63.6 | 7.36E−05 | 61.90 |
| 64 | B | Pd(dppe)2 | 2.00 | 90 | 0.90 | 1.48E−06 | 0.45 | 91.5 | 7.40E−05 | 87.80 |
| 65 | B | RuCl2(DMSO)4 | 2.00 | 90 | 7.80 | 2.03E−05 | 3.90 | 97.1 | 1.02E−03 | 95.90 |

TABLE 6-continued

| Ex. # | Pro-cedure | Catalyst | Mole % metal | Run T (C) | Final Conv. by POx (%) | Conv. Rate (min −1) | Turnover # | Ave. Slope Select to (PI + PIII) | Average Normalized Rate mole P/Mole M/min | Cumulative Select-ivity to (PI + PII) |
|---|---|---|---|---|---|---|---|---|---|---|
| 66 | B | Ni(PPh3)4 | 1.84 | 90 | 9.60 | 2.02E−05 | 5.23 | 86.7 | 1.10E−03 | 84.70 |
| 67 | B | [CpNi(CO)]2 | 2.00 | 90 | 79.20 | 1.45E−04 | 39.60 | 86.0 | 7.26E−03 | 86.00 |
| 68 | B | Co2(CO)8 | 2.00 | 90 | 5.00 | 1.42E−05 | 2.50 | 91.2 | 7.11E−04 | 91.90 |
| 69 | B | Co(CO)6 (PPh3)2 | 2.00 | 90 | 0.40 | 3.92E−06 to (−7.5E−07) | 0.20 | 84.6 | 1.96E−4 to (−3.75E−5) | 78.60 |
| 70 | B | RuCl2(PPh3)3 | 2.00 | 90 | 1.80 | 6.17E−06 | 0.90 | 97.0 | 3.09E−04 | 94.60 |
| 71 | B | RnCl(PPh3)3 | 2.00 | 90 | 10.50 | 1.47E−05 | 5.25 | 97.2 | 7.33−04 | 97.70 |
| 72 | B | Ni(cod)2 (Strem) | 2.00 | 90 | 39.10 | 3.78E−05 | 19.60 | 88.2 | 1.89E−03 | 89.50 |
| 73 | B | Ru(CO)3 (PPh3)2 | 2.00 | 90 | 0.40 | 6.68E−07 | O#2O | 72.4 | 3.34E−05 | 71.90 |
| 74 | B | RhCl(CO) (PPh3)2 | 2.00 | 90 | 3.00 | 5.12E−06 | 1.50 | 91.1 | 2.56E−04 | 93.90 |
| 75 | B | IrCl(CO) (PPh3)2 | 2.00 | 90 | 1.20 | 3.13E−06 | 0.60 | 86.3 | 1.57E−04 | 79.60 |
| 76 | B | Ni(II) stearate | 2.00 | 90 | 31.10 | 7.38E−05 | 15.55 | 91.8 | 3.69E−03 | 90.10 |
| 77 | B | Mn(II)phthalo-cyanine | 2.00 | 90 | 0.20 | 4.40E−07 | 0.10 | 90.7 | 3.67E−05 | 83.90 |
| 78 | B | RhCl(PPh3)3 | 2.00 | 110 | 15.40 | 1.07E−04 | 7.70 | 98.2 | 5.32E−03 | 97.90 |
| 79 | B | CPNiCl(PPh3) | 2.00 | 90 | 66.40 | 1.42E−04 | 33.19 | 86.8 | 7.09E−03 | 86.90 |
| 80 | B | CpRuCl(PPh3)2 | 2.00 | 90 | 2.30 | 8.57E−06 | 1.1S | 88.7 | 4.28E−04 | 88.60 |
| 81 | B | RhCl(PPh3)3 | 2.00 | 130 | 17.00 | 1.58E−04 | 8.50 | 87.9 | 7.93E−03 | 87.90 |
| 82 | B | Cu(PPh3) (NO) | 2.00 | 90 | 3.50 | 9.93E−06 | 1.66 | 87.2 | 4.71E−04 | 86.50 |
| 83 | B | Cu(2-ethyl-hexanoate | 2.00 | 90 | 3.90 | 7.6SE−06 | 1.95 | 78.1 | 3.82E−04 | 70.40 |
| 84 | B | Cu(2-ethyl-hexanoate + 2 mol % pyridine | 2.00 | 90 | 4.20 | 8.48E−06 | 2.10 | 85.1 | 4.23E−04 | 77.10 |
| 85 | B | Ag (O2CC6H4CF3) | 2.00 | 90 | 1.90 | 3.41E−06 | 0.94 | 76.9 | 1.68E−04 | 69.70 |
| 86 | B | Au colloid polyvinyl-pyrrolidone supported-0.3 mol % | 0.30 | 90 | 3.70 | 6.86E−06 | 11.97 | 99.6 | 2.23E−03 | 87.10 |
| 87 | B | [RnCl(cod)]2 | 2.00 | 90 | 18.30 | 4.32E−05 | 9.17 | 93.1 | 93.40 | |
| 88 | B | Rh colloid polyvinyl-pyrrolidone supported | 1.4S | 90 | 10.70 | 2.41E−05 | 9.02 | 81.7 | 2.03E−03 | 83.90 |
| 89 | B | Ni(CO)2(PPh3)2 | 2.00 | 90 | 75.10 | 7.98E−06 to 2.14E−04 | 37.42 | 90.2 | 5.56E−03 | 84.20 |
| 90 | B | Ni(CO)2(PPh3) 2 + 2 eq. PPh3 | 2.00 | 90 | 83.20 | 1.00E−04 | 41.58 | 89.6 | 5.96E−03 | 81.80 |
| 91 | B | Ni(CO)2(PPh3) 2 + 1.14 eq methyl-viologen | 2.00 | 90 | 37.40 | 7.12E−05 | 18.71 | 91.8 | 3.56E−03 | 89.50 |
| 92 | B | Zr powder | 10.00 | 90 | 0.40 | 8.27E−07 | 0.04 | 75.1 | 8.27E−06 | 69.30 |
| 93 | B | Mn(III) (acac)3 | 2.06 | 90 | 0.60 | 8.13E−07 | 0.29 | 100.0 | 93.90 | |
| 94 | B | Au colloid-polyvinyl-pyrrolidone supported-1.3 mol % | 1.30 | 90 | 13.80 | 1.87E−05 | 9.61 | 68.8 | 1.31E−03 | 77.10 |
| 95 | B | Ti powder | 10.00 | 90 | 0.40 | 7.14E−07 | 0.04 | 77.5 | 6.97E−06 | 67.70 |
| 96 | B | Rh(NO)(PPh3)3 | 2.00 | 90 | 10.70 | 9.48E−06 | 5.77 | 92.6 | 5.11E−04 | 91.60 |
| 97 | B | Cr(C6H6)2 | 2.00 | 90 | 0.60 | 1.10E−06 | 0.30 | 100.0 | 5.50E−05 | 93.20 |
| 98 | B | Cr(C6H6)(CO)3 | 2.00 | 90 | 0.20 | 1.26E−07 | 0.10 | 100.0 | 6.27E−06 | 77.8O |
| 99 | B | MnBr2 | 2.00 | 90 | 0.30 | 2.27E−07 | 0.15 | 100.0 | 1.14E−05 | 85.40 |
| 100 | B | (C5H5)2Ni | 2.00 | 90 | 79.30 | 2.51E−04 | 39.90 | 87.0 | 1.26E−02 | 84.70 |
| 101 | B | Co(C5H5)(CO)2 | 2.00 | 90 | 1.40 | 3.01E−06 | 0.66 | 76.9 | 1.43E−04 | 75.80 |
| 102 | B | (C5Me5)2Ni | 2.00 | 90 | 34.90 | 3.42E−05 | 17.46 | 86.2 | 1.71E−03 | 87.50 |
| 103 | B | [(C5Me5)Mo (CO)2]2 | 2.00 | 90 | 0.90 | 1.71E−06 | 0.31 | S0.4 | 5.83E−05 | 54.90 |
| 104 | B | NiTiO3 | 2.00 | 90 | 0.40 | 1.02E−06 | 0.20 | 46.1 | 5.05E−05 | 57.30 |
| 105 | B | Ni3S2 | 2.00 | 90 | 23.00 | 3.24E−05 | 11.64 | 87.1 | 1.64E−03 | 87.70 |
| 106 | B | [(C5H5)Fe (CO)2 (CH2CMe2)]BF4 | 1.30 | 90 | 3.50 | 3.76E−06 | 2.66 | 90.0 | 2.84E−04 | 95.60 |

TABLE 6-continued

| Ex. # | Procedure | Catalyst | Mole % metal | Run T (C) | Final Conv. by POx (%) | Conv. Rate (min −1) | Turnover # | Ave. Slope Select to (PI + PIII) | Average Normalized Rate mole P/Mole M/min | Cumulative Selectivity to (PI + PII) |
|---|---|---|---|---|---|---|---|---|---|---|
| 107 | B | [(C5H5)Fe(CO)2(CH2C(OEt)2)]BF4 | 1.80 | 90 | 4.10 | 3.12E−06 | 2.27 | 100.0 | 1.73E−04 | 98.90 |
| 108 | B | NiCl2(dppe) | 1.70 | 90 | 3.90 | 4.58E−06 | 2.30 | 84.4 | 2.72E−04 | 83.10 |
| 109 | B | [(C5H5)Fe(CO)2]2 | 2.00 | 90 | 0.20 | 1.48E−07 | 0.10 | 100.0 | 1.44E−05 | 75.00 |
| 110 | B | (C5H5)Fe(CO)21 | 2.00 | 90 | 0.50 | 6.18E−07 | 0.24 | 100.0 | 3.02E−05 | 83.70 |
| 111 | B | NiCl2(PPh3)2 | 2.00 | 90 | 91.90 | 1.47E−04 | 44.68 | 87.4 | 7.13E−03 | 87.00 |
| 112 | B | (C5H5)Cu(PEt3) | 2.00 | 90 | 43.20 | 2.86E−05 | 22.96 | 97.7 | 1.34E−03 | 97.70 |
| 113 | A | Cp-100 carbon | 0.20 | 90 | 0.20 | 8.61E−07 | 0.0050 | 73.4 |  | 68.30 |
| 114 | A | Graphite Flakes | 0.21 | 90 | 0.20 | 1.74E−06 | 0.0040 | 50.6 |  | 56.50 |

EXAMPLES 115–118

In the experimental oxidation runs of Examples 116–118, a teflon covered stir bar was placed in a glass liner for 300 cc autoclave and the liner placed in a 65° C. oil bath within a glove box maintained under an Ar atmosphere. A mass of tetraphosphorus was placed in the liner and allowed to melt with slow stirring. A predetermined charge of $CuCl_2 \cdot 2H_2O$ (dry powder) was weighed and added to a standard test tube. Distilled, degased water (500 µL) was added to the $CuCl_2$ in the test tube and the resulting solution was warmed in the 65° C. oil bath within the glove box for 5 minutes as an aid to dissolution of the $CuCl_2$. The extent of dilution was about 90%. The resulting dark green catalyst solution was pipetted onto the molten $P_4$ in the glass liner with slow stirring. The test tube containing residual $CuCl_2$ and minor amounts of undissolved $CuCl_2$ was washed with distilled, degased water (400 µL) and this wash solution was transferred into the glass liner containing the molten phosphorus.

Stirring of the $P_4/CuCl_2/H_2O$ mixture was continued for about 5 minutes during which time the molten $P_4$ mass gradually mixed with the catalyst solution, then progressively thickened until it set up into a solid mass. Various color changes accompanied this transition. Initially, there was a distinct green aqueous phase and a yellow $P_4$ phase. This was followed by a brown aqueous phase together with a silvery phosphorus phase. By the time the solid mixed $P_4$/catalyst phase had developed, there was very little aqueous phase observable. After the solid catalyst/$P_4$ mass had formed, the glass liner containing this mixture was allowed to stand in the oil bath for an additional 25 minutes after which it was removed from the oil bath and allowed to cool for about 5 minutes.

A predetermined amount of distilled, degased water (about 125 mL) was then added to the liner and the liner sealed with a large rubber stopper. The solid $P_4$/catalyst phase had no apparent miscibility with the aqueous phase. The liner containing the water and $P_4$/catalyst charge mixture was transferred to the autoclave which was maintained under Ar purge. The rubber stopper was not removed from the glass liner until immediately prior to placement in the reactor and securing of the reactor head. After securing the head, leak testing, and establishing appropriate thermocouple, and liquid sampling connections, the reactor was wrapped with heating tape and insulated. The final state of the reactor immediately before heat up to reaction temperature was room temperature and 0 psig Ar. The Ar connection was above the liquid level.

The reactor body and the head heaters were turned on and the temperature ramped up gradually to the run temperature of 110° C. in the charge mixture. The reactor head was kept roughly 10° C. higher than the reactor through most of the heat up phase. Total time required to reach 110° C. was about 50 minutes. In the various runs of these Examples, the heat up time was maintained as close as possible to the same time for each run. Generally, there was a minor temperature overshoot of 3–5° C. lasting about 20 minutes. The run clock was started when the reactor contents initially reached 110° C. Reactor liquid contents were sampled periodically over the duration of each run. At the end of the run, the reactor was allowed to cool and a sample of the head space gas was captured before venting the reactor.

The procedure for Example 115 differed slightly from the procedure described above in that the liner was placed in the reactor prior to charging distilled water and the $P_4$/catalsyt charge was initially prepared in a test tube rather than in the reactor liner. Immediately prior to this run, the test tube was broken under water (outside the reactor) and the solid $P_4$/catalyst mass was removed and transferred by hand quickly and directly into the reactor after the water (125° C.) had been added to the liner.

Example 118 was a special run which was conducted in the manner described above except that after 2 hours at 110° C. the reactor was cooled and vented, the head space was purged, and the reactor was reheated. The purpose of that procedure was to determine if the "interrupted" reaction would recommence at the same rate that it had been progressing immediately prior to the interruption.

A summary of the $P_4/CuCl_2 \cdot 2H_2O$ and water charged to each of the reactions of this Example is set forth in Table 7.

TABLE 7

| MW | | Grams | | | | moles | | | |
|---|---|---|---|---|---|---|---|---|---|
| | | Ex. 115 | Ex. 116 | Ex. 117 | Ex. 118 | Ex. 115 | Ex. 116 | Ex. 117 | Ex. 118 |
| $P(asP_4)$ | 30.97 | 1.21 | 2.43 | 1.80 | 1.37 | 0.0391 | 0.0785 | 0.0581 | 0.0442 |
| $CuCl_2 \cdot 2H_2O$ | 170.47 | 0.67 | 0.67 | 0.67 | 0.75 | 0.0039 | 0.0039 | 0.0039 | 0.0044 |
| $H_2O$ (total) | 18.02 | 126.41 | 125.36 | 126.50 | 128.50 | 7.02 | 6.96 | 7.02 | 7.13 |
| Initial Cu/P Molar Ratio | | | | | | 0.101 | 0.050 | 0.068 | 0.099 |
| Initial P/Cu Molar Ratio | | | | | | 9.941 | 19.964 | 14.788 | 10.055 |

Figure 29:
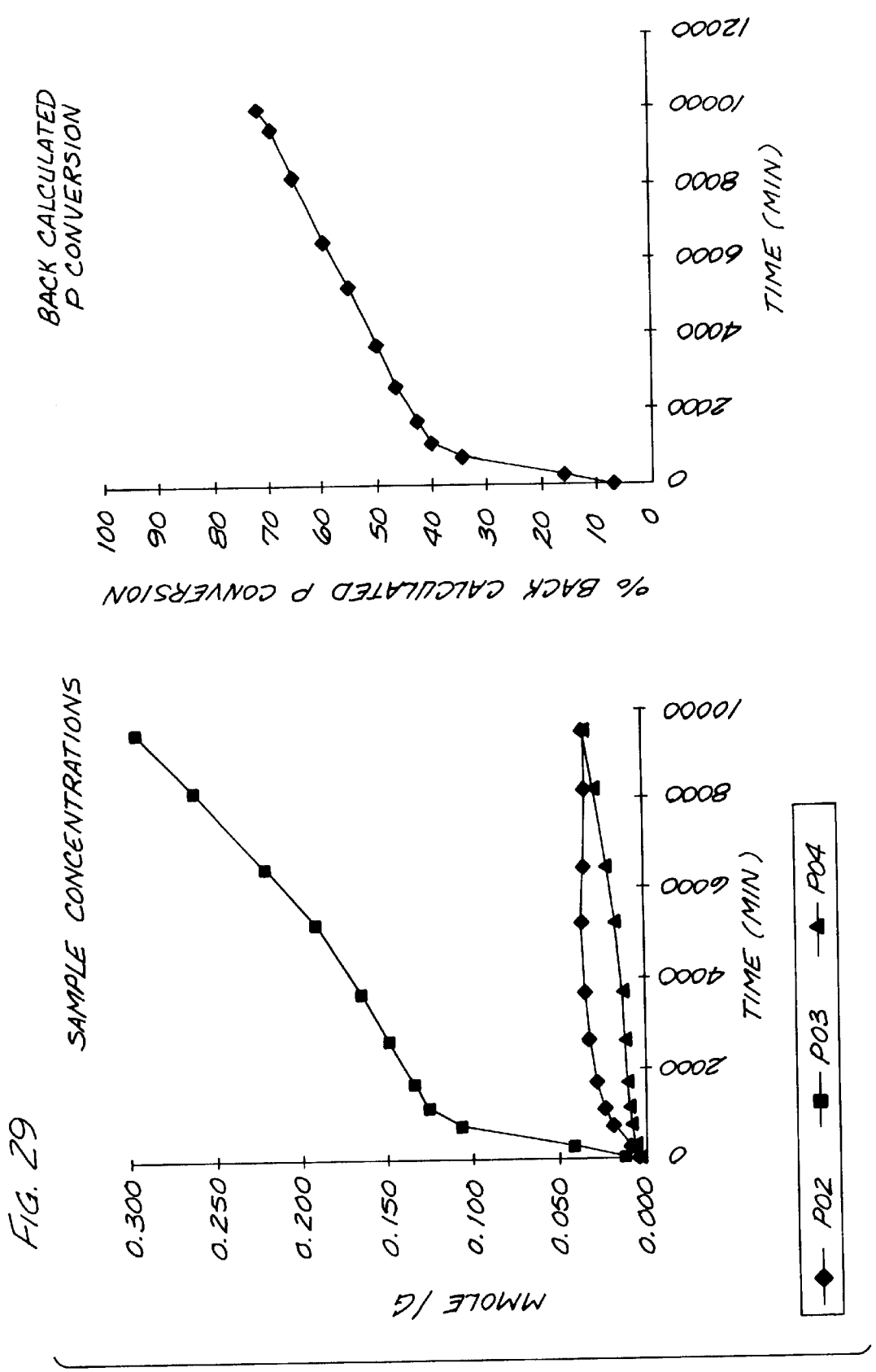
FIGS. 29/29A to 32/32A contain series of plots of sample concentrations, back calculated phosphorus conversions, selectivities, and rates vs. time for the experimental runs of Examples 115–118, respectively.
Figure 29A:
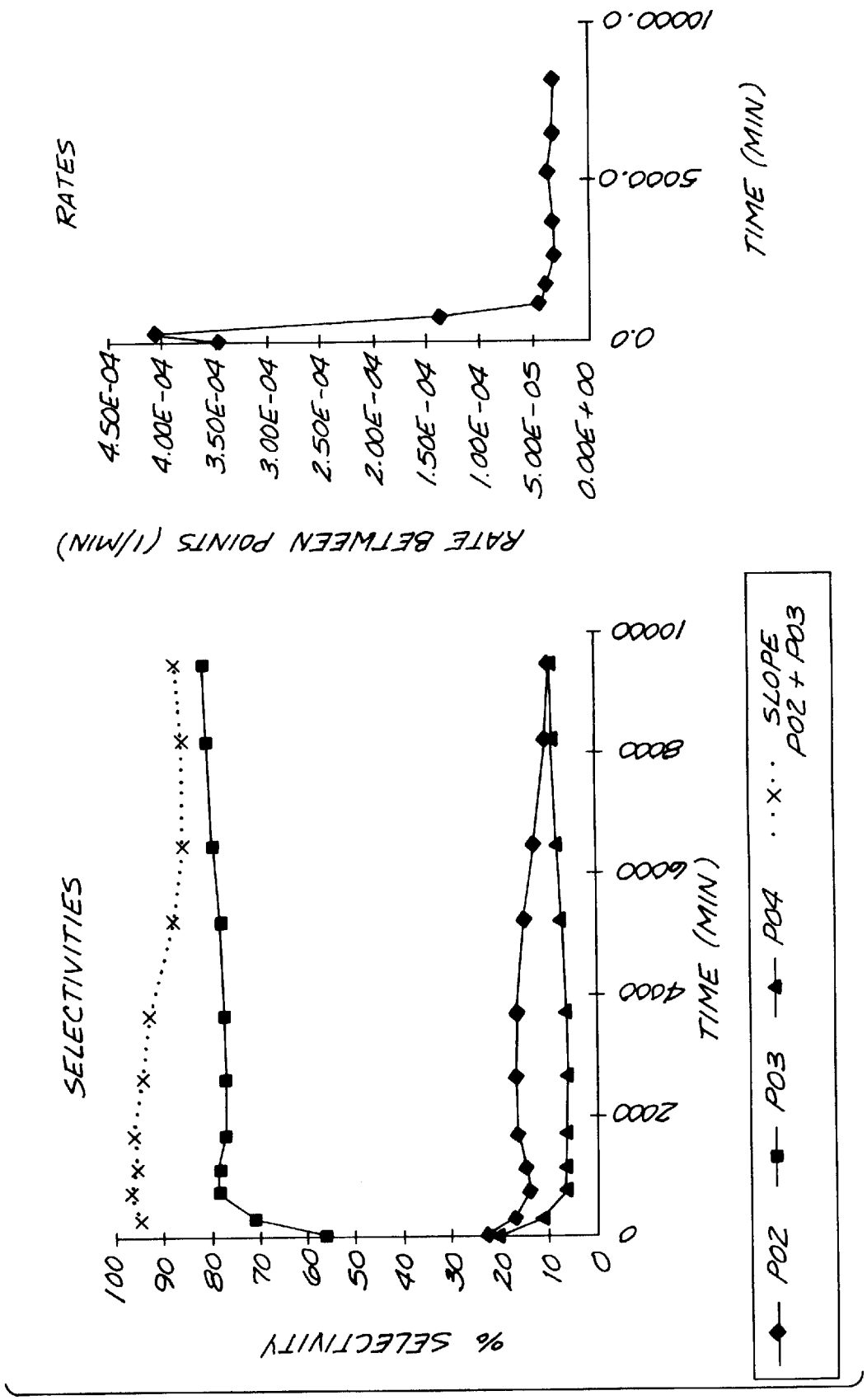
Figure 30A:
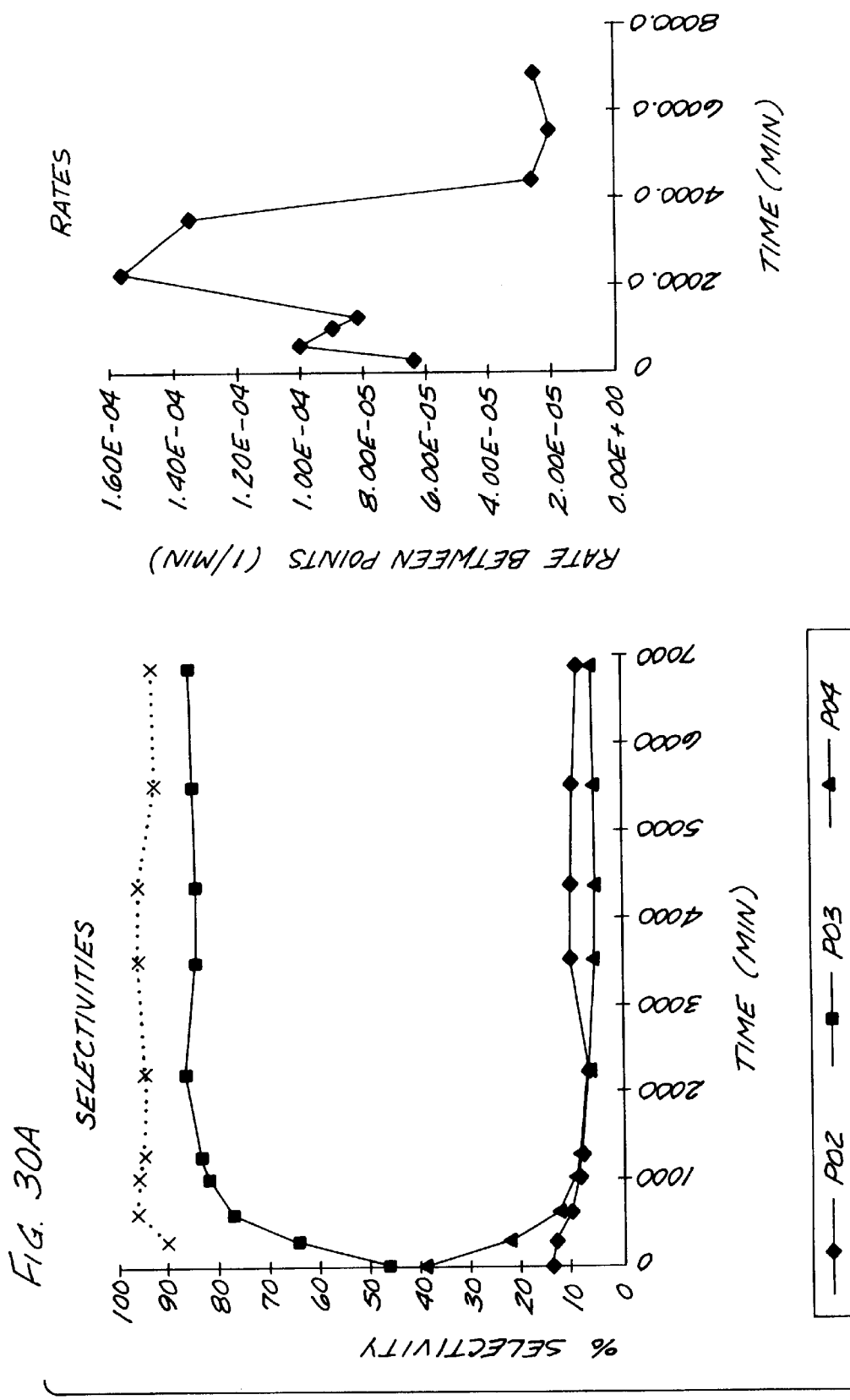
Figure 31:
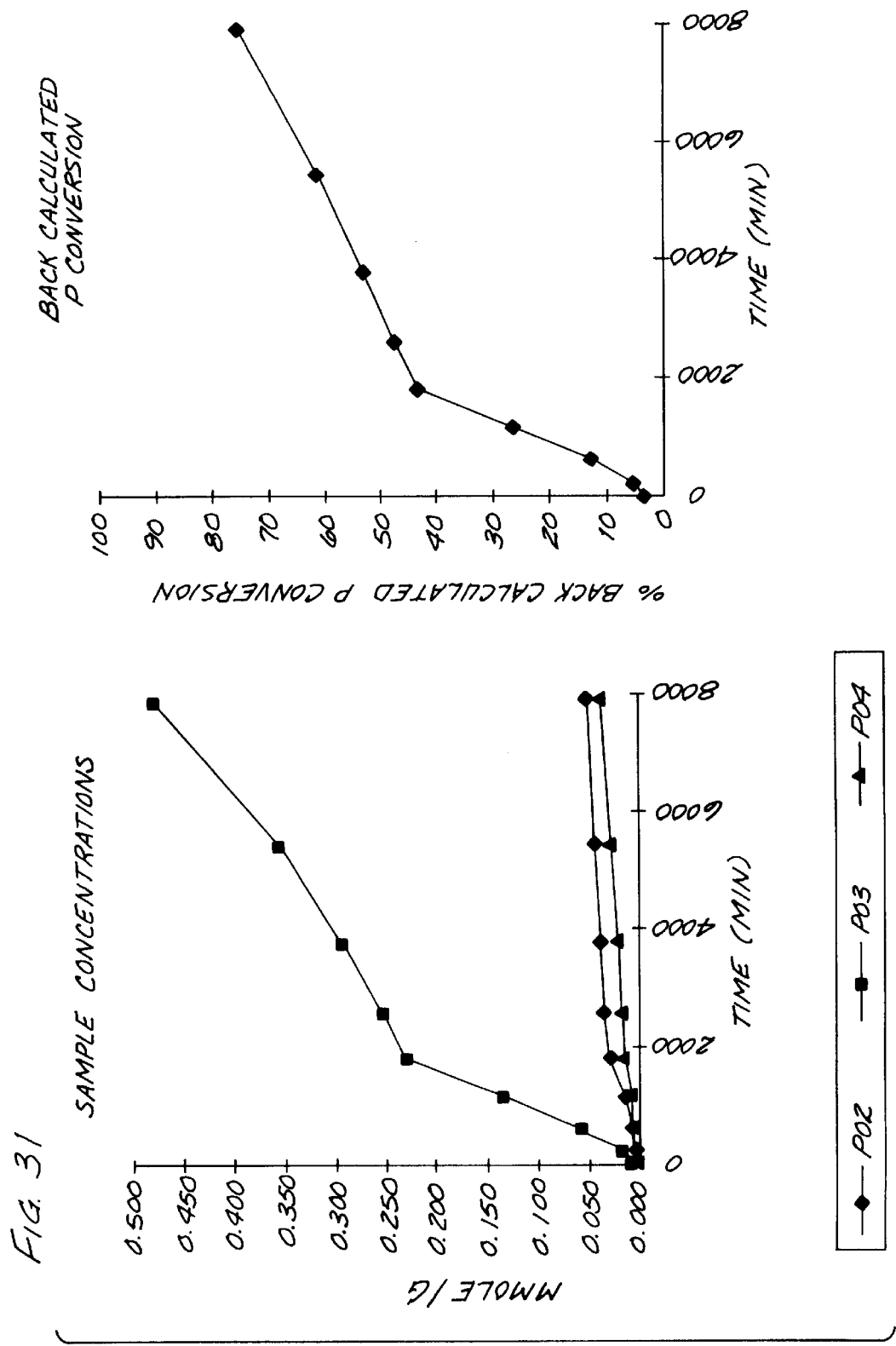
Figure 31A:
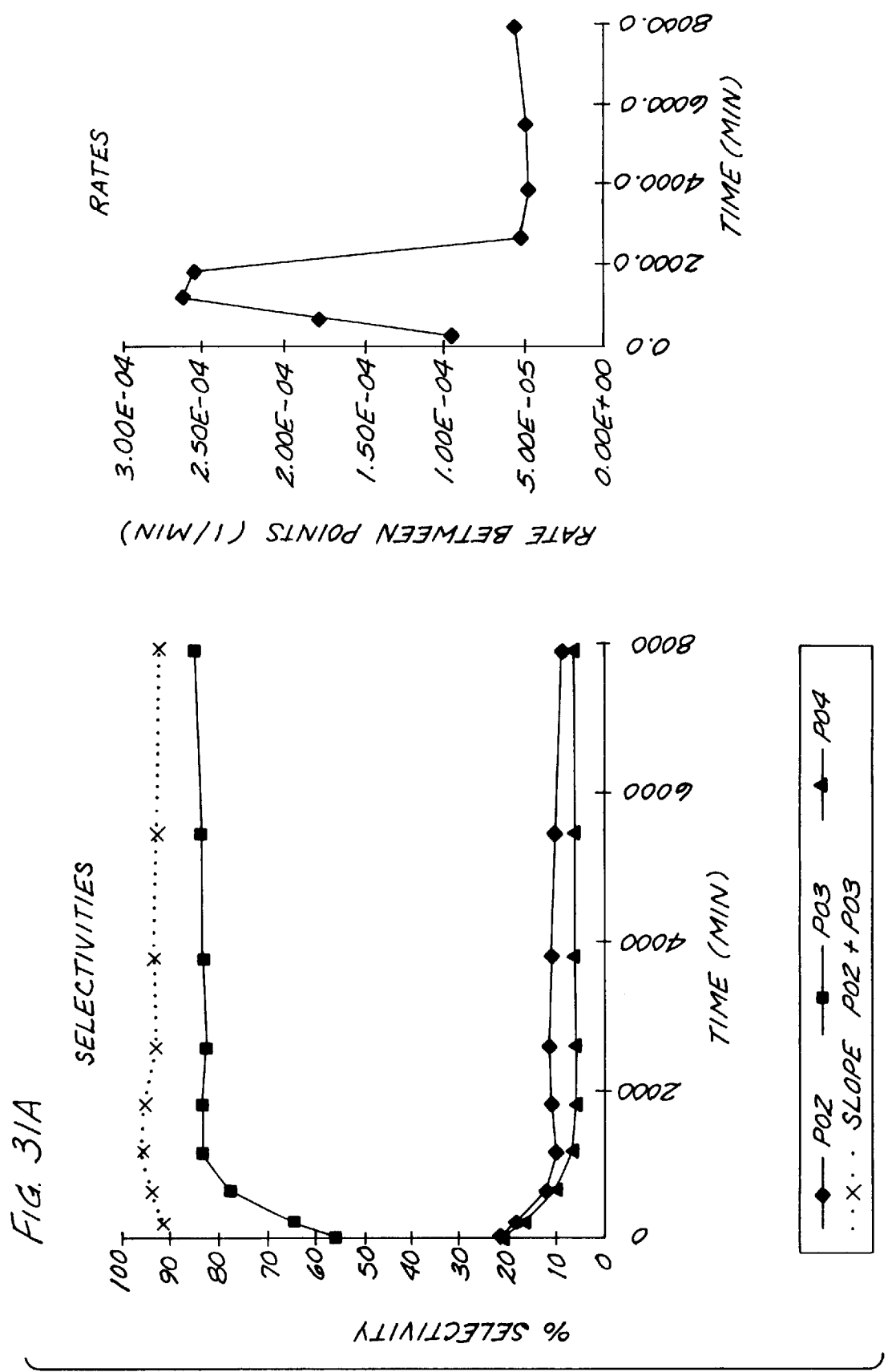

A summary of temperature reactor pressure, sample analyses, cummulative selectivities, slope selectivity, apparent $P_4$ conversion, zero order rate and normed rate for the runs of these Examples are set forth in Tables 8–11A. Set forth in FIG. 29/29A are plots of sample concentrations, back calculated phosphorus conversion, selectivities and rates against time for the runs of Example 115. Similar plots for Examples 116–118 are set forth in FIGS. 30/30A to 32/32A, respectively.

FIG. 33 sets forth the apparent instantaneous rates (average rates) between points as a function of time for 3 different catalyst loadings of Examples 115–117, respectively.

TABLE 8

Example 115
Comments: 10% CuCl2.2H2O Preform 110° C. in Inerted Autoclave

| Sample # | | $H_2O$ | $P_4$ | $H_3PO_2$ | $H_3PO_3$ | $H_3PO_4$ | Catalyst | g cat metal/ g P |
|---|---|---|---|---|---|---|---|---|
| Charges (g) | | 110.8 | 1.21 | 0 | 0 | 0 | 0.67 | 0.20661157 |

| | Run Time | T | Reactor P | Sample Concentrations Wt % | | |
|---|---|---|---|---|---|---|
| Sample # | (min) | (C) | (psig) | $PO_2$ | $PO_3$ | $PO_4$ |
| (pre-run) 1 | | | — | | | |
| 2 | 35.0 | 110.3 | 16.9 | 0.035 | 0.110 | 0.049 |
| 3 | 298.0 | 110.9 | 29.6 | 0.064 | 0.336 | 0.066 |
| 4 | 755.0 | 110.4 | 40.6 | 0.122 | 0.849 | 0.090 |
| 5 | 1148.0 | 111.6 | 42.9 | 0.150 | 0.997 | 0.100 |
| 6 | 1718.0 | 112.5 | 46.2 | 0.179 | 1.059 | 0.105 |
| 7 | 2661.0 | 110.7 | 51.1 | 0.204 | 1.175 | 0.116 |
| 8 | 3705.0 | 110.5 | 56.9 | 0.219 | 1.297 | 0.129 |
| 9 | 5253.0 | 111.3 | 66.1 | 0.228 | 1.511 | 0.167 |
| 10 | 6472.0 | 110.8 | 72.3 | 0.221 | 1.741 | 0.212 |
| 11 | 8217.0 | 110.9 | 77.9 | 0.211 | 2.071 | 0.277 |
| 12 | 9479.0 | 110.5 | 82.4 | 0.219 | 2.327 | 0.324 |
| 13 | 10007.0 | 109.9 | 81.2 | 0.187 | 2.521 | 0.383 |

| | Cumulative Selectivities | | | Slope Selectivity $PO_2 + PO_3$ | Apparent $P_4$ Conversion | Zero Order Rate (Min^-1) | | Normed Rate mole P/mole metal/min | |
|---|---|---|---|---|---|---|---|---|---|
| Sample # | $PO_2$ | $PO_3$ | $PO_4$ | | | Last From t = 0 | From Point | Last From t = 0 | From Point |
| (pre-run) 1 | | | | | | | | | |
| 2 | 0.227 | 0.564 | 0.209 | | 7.1% | 2.03E-03 | — | 2.01E-02 | — |
| 3 | 0.171 | 0.713 | 0.116 | 0.949 | 16.2% | 5.44E-04 | 3.46E-04 | 5.40E-03 | 3.44E-03 |
| 4 | 0.142 | 0.789 | 0.069 | 0.967 | 34.8% | 4.61E-04 | 4.07E-04 | 4.57E-03 | 4.04E-03 |
| 5 | 0.148 | 0.786 | 0.066 | 0.955 | 40.2% | 3.50E-04 | 1.39E-04 | 3.48E-03 | 1.38E-03 |
| 6 | 0.164 | 0.773 | 0.064 | 0.961 | 42.9% | 2.49E-04 | 4.61E-05 | 2.48E-03 | 4.58E-04 |
| 7 | 0.167 | 0.770 | 0.063 | 0.944 | 46.6% | 1.75E-04 | 3.96E-05 | 1.74E-03 | 3.94E-04 |
| 8 | 0.164 | 0.772 | 0.064 | 0.927 | 49.9% | 1.35E-04 | 3.18E-05 | 1.34E-03 | 3.15E-04 |
| 9 | 0.148 | 0.780 | 0.072 | 0.876 | 55.0% | 1.05E-04 | 3.30E-05 | 1.04E-03 | 3.27E-04 |
| 10 | 0.126 | 0.793 | 0.080 | 0.856 | 59.6% | 9.21E-05 | 3.74E-05 | 9.14E-04 | 3.72E-04 |
| 11 | 0.103 | 0.807 | 0.090 | 0.856 | 65.4% | 7.95E-05 | 3.31E-05 | 7.90E-04 | 3.28E-04 |
| 12 | 0.096 | 0.810 | 0.094 | 0.870 | 69.4% | 7.32E-05 | 3.19E-05 | 7.27E-04 | 3.17E-04 |
| 13 | 0.076 | 0.820 | 0.104 | 0.761 | 71.8% | 7.18E-05 | 4.61E-05 | 7.13E-04 | 4.57E-04 |

TABLE 9

Example 116
Comments: 5 mole % CuCl2.2H2O Preform, Inerted Clave, 110° C.

| | $H_2O$ | $P_4$ | $H_3PO_2$ | $H_3PO_3$ | $H_3PO_4$ | Catalyst | g cat metal/ g P |
|---|---|---|---|---|---|---|---|
| Charges (g) | 111.567 | 2.43 | 0 | 0 | 0 | 0.67 | 0.102757202 |

| Sample # | Run Time (min) | T (C) | Reactor P (psig) | Sample Concentrations Wt % | | |
|---|---|---|---|---|---|---|
| | | | | $PO_2$ | $PO_3$ | $PO_4$ |
| (pre-run) 1 | | | — | | | |
| 2 | 10.0 | 114.6 | 18.1 | 0.009 | 0.037 | 0.038 |
| 3 | 285.0 | 110.8 | 28.4 | 0.019 | 0.119 | 0.050 |
| 4 | 624.0 | 110.2 | 36.9 | 0.032 | 0.309 | 0.060 |
| 5 | 1032.0 | 111.3 | 45.8 | 0.044 | 0.530 | 0.072 |
| 6 | 1291.0 | 111.8 | 49.3 | 0.051 | 0.668 | 0.082 |
| 7 | 2231.0 | 110.2 | 66.4 | 0.103 | 1.694 | 0.157 |
| 8 | 3518.0 | 111.8 | 87.2 | 0.277 | 2.913 | 0.230 |
| 9 | 4364.0 | 112 | 90.3 | 0.294 | 3.102 | 0.241 |
| 10 | 5522.0 | 111.8 | 96.5 | 0.302 | 3.332 | 0.264 |
| 11 | 6868.0 | 111.2 | 103.9 | 0.297 | 3.739 | 0.301 |

| Sample # | Cumulative Selectivities | | | Slope Selectivity PO2 + PO3 | | P4 Conversion | Zero Order Rate (Min^-1) | | Normed Rate mole P/mole metal/min | |
|---|---|---|---|---|---|---|---|---|---|---|
| | $PO_2$ | $PO_3$ | $PO_4$ | Cum | Slope | Apparent | From $t = 0$ | From Last Point | From $t = 0$ | From Last Point |
| (pre-run) 1 | | | | | | | | | | |
| 2 | 0.138 | 0.466 | 0.395 | 0.605 | | 1.4% | 1.43E-03 | — | 2.86E-02 | — |
| 3 | 0.130 | 0.644 | 0.226 | 0.774 | 0.903 | 3.2% | 1.12E-04 | 6.41E-05 | 2.24E-03 | 1.28E-03 |
| 4 | 0.100 | 0.774 | 0.126 | 0.874 | 0.960 | 6.6% | 1.06E-04 | 1.01E-04 | 2.12E-03 | 2.01E-03 |
| 5 | 0.086 | 0.821 | 0.093 | 0.907 | 0.960 | 10.3% | 9.97E-05 | 9.01E-05 | 1.99E-03 | 1.80E-03 |
| 6 | 0.080 | 0.835 | 0.085 | 0.915 | 0.948 | 12.4% | 9.61E-05 | 8.20E-05 | 1.92E-03 | 1.64E-03 |
| 7 | 0.066 | 0.867 | 0.067 | 0.933 | 0.946 | 27.2% | 1.22E-04 | 1.57E-04 | 2.43E-03 | 3.13E-03 |
| 8 | 0.101 | 0.844 | 0.055 | 0.945 | 0.959 | 44.5% | 1.27E-04 | 1.35E-04 | 2.53E-03 | 2.70E-03 |
| 9 | 0.100 | 0.845 | 0.055 | 0.945 | 0.960 | 46.8% | 1.07E-04 | 2.63E-05 | 2.14E-03 | 5.25E-04 |
| 10 | 0.096 | 0.848 | 0.056 | 0.944 | 0.925 | 49.2% | 8.90E-05 | 2.06E-05 | 1.78E-03 | 4.11E-04 |
| 11 | 0.086 | 0.857 | 0.057 | 0.943 | 0.929 | 52.7% | 7.68E-05 | 2.64E-05 | 1.53E-03 | 5.28E-04 |

TABLE 10

Example 117
Comments: 6.8 mole % CuCl2.2H2O Preform, Inerted Clave, 110° C.

| | H2O | P4 | H3PO2 | H3PO3 | H3PO4 | Catalyst | g cat metal/g P |
|---|---|---|---|---|---|---|---|
| Charges (g) | 110.9 | 1.8 | 0 | 0 | 0 | 0.67 | 0.138888889 |

| Sample # | Run Time (min) | T (C) | Reactor P (psig) | Sample Concentrations Wt % | | |
|---|---|---|---|---|---|---|
| | | | | PO2 | PO3 | PO4 |
| (pre-run) 1 | | | — | | | |
| 2 | 20.0 | 110.5 | 19.3 | 0.025 | 0.081 | 0.037 |
| 3 | 225.0 | 111.1 | 30.2 | 0.034 | 0.149 | 0.046 |
| 4 | 650.0 | 110.2 | 44.6 | 0.056 | 0.456 | 0.072 |
| 5 | 1173.0 | 110.3 | 61.2 | 0.101 | 1.059 | 0.106 |
| 6 | 1827.0 | 110.6 | 74.8 | 0.190 | 1.812 | 0.155 |
| 7 | 2602.0 | 110.5 | 80.8 | 0.224 | 1.994 | 0.175 |
| 8 | 3792.0 | 110.7 | 91.1 | 0.242 | 2.308 | 0.203 |
| 9 | 5453.0 | 110.2 | 104.9 | 0.274 | 2.799 | 0.252 |
| 10 | 7940.0 | 111.7 | 126.2 | 0.311 | 3.766 | 0.350 |

TABLE 10-continued

Example 117
Comments: 6.8 mole % CuCl2.2H2O Preform, Inerted Clave, 110° C.

| Sample # | Cumulative Selectivities | | | Slope Selectivities PO2 + PO3 Cum | Slope | Apparent P4 Conversion | Zero Order Rate (min ^−1) | | Normed Rate mole P/mole metal/min | |
|---|---|---|---|---|---|---|---|---|---|---|
| | PO2 | PO3 | PO4 | | | | From t = 0 | From Last Point | From t = 0 | From Last Point |
| (pre-run) 1 | | | | | | | | | | |
| 2 | 0.219 | 0.565 | 0.217 | 0.783 | | 3.5% | 1.75E−03 | — | 2.58E−02 | — |
| 3 | 0.185 | 0.648 | 0.166 | 0.834 | 0.918 | 5.5% | 2.42E−04 | 9.57E−05 | 3.58E−03 | 1.41E−03 |
| 4 | 0.120 | 0.778 | 0.102 | 0.898 | 0.939 | 13.1% | 2.01E−04 | 1.79E−04 | 2.97E−03 | 2.65E−03 |
| 5 | 0.099 | 0.832 | 0.069 | 0.931 | 0.959 | 26.8% | 2.28E−04 | 2.62E−04 | 3.37E−03 | 3.88E−03 |
| 6 | 0.109 | 0.832 | 0.059 | 0.941 | 0.955 | 43.5% | 2.38E−04 | 2.56E−04 | 3.52E−03 | 3.78E−03 |
| 7 | 0.116 | 0.824 | 0.060 | 0.940 | 0.931 | 47.6% | 1.83E−04 | 5.26E−05 | 2703E−03 | 7.76E−04 |
| 8 | 0.109 | 0.830 | 0.061 | 0.939 | 0.935 | 53.3% | 1.40E−04 | 4.75E−05 | 2.07E−03 | 7.02E−04 |
| 9 | 0.103 | 0.835 | 0.062 | 0.938 | 0.929 | 61.5% | 1.13E−04 | 4.94E−05 | 1.66E−03 | 7.30E−04 |
| 10 | 0.088 | 0.847 | 0.065 | 0.935 | 0.925 | 75.5% | 9.51E−05 | 5.63E−05 | 1.40E−03 | 8.32E−04 |

TABLE 11

Example 118
Comments: 10 mole % Cu by CuCl2.2H2O, 110° C., Clave, Aborted Run Trail

| | H2O | P4 | H3PO2 | H3PO3 | H3PO4 | Catalyst | g cat metal/g P |
|---|---|---|---|---|---|---|---|
| Charges (g) | 113.5 | 1.37 | 0 | 0 | 0 | 0.75 | 0.204379562 |

| Sample # | Run Time (min) | T (C) | Reactor P (psig) | Sample Concentrations Wt % | | |
|---|---|---|---|---|---|---|
| | | | | PO2 | PO3 | PO4 |
| (pre-run) 1 | | | — | | | |
| 2 | 87.0 | 111.2 | 20.2 | 0.033 | 0.135 | 0.057 |
| 3 | 126.0 | 111.4 | 21.5 | 0.040 | 0.159 | 0.060 |
| 4 | 311.0 | 34.5 | 0 | 0.043 | 0.193 | 0.062 |
| 5 | 1176.0 | 111.6 | 46.2 | 0.186 | 1.438 | 0.131 |
| 6 | 1317.0 | 110.3 | 45.8 | 0.338 | 1.501 | 0.143 |

| Sample # | Cumulative Selectivities | | | Slope Selectivities PO2 + PO3 Cum | Slope | Apparent P4 Conversion | Zero Order Rate (min ^−1) | | Normed Rate mole P/mole metal/min | |
|---|---|---|---|---|---|---|---|---|---|---|
| | PO2 | PO3 | PO4 | | | | From t = 0 | From Last Point | From t = 0 | From Last Point |
| (pre-run) 1 | | | | | | | | | | |
| 2 | 0.184 | 0.603 | 0.213 | 0.787 | | 7.3% | 8.37E−04 | — | 8.40E−03 | — |
| 3 | 0.193 | 0.614 | 0.193 | 0.807 | 0.935 | 8.3% | 6.61E−04 | 2.67E−04 | 6.63E−03 | 2.68E−03 |
| 4 | 0.181 | 0.645 | 0.173 | 0.827 | 0.953 | 9.4% | 3.04E−04 | 6.06E−05 | 3.05E−03 | 6.08E−04 |
| 5 | 0.131 | 0.808 | 0.061 | 0.939 | 0.962 | 48.6% | 4.14E−04 | 4.53E−04 | 4.15E−03 | 4.55E−03 |
| 6 | 0.207 | 0.735 | 0.058 | 0.942 | 0.962 | 54.9% | 4.17E−04 | 4.45E−04 | 4.18E−03 | 4.47E−03 |

The "apparent" or "back calculated" $P_4$ conversions are apparently low by about 10%, due to the presence of phosphine gas in the reactor headspace (not identified in liquid sample analyses). It appears that most of the $PH_3$ is formed during the initial "fast" portion of the reaction. Each run exhibited a break in the reaction rate. The divergence between the observed reactor pressure rise vs. that determined from stoichiometric and gas law calculations appeared to have occured during the initial fast portion of the reaction, after which the actual and computed pressure curve become parallel. This may reflect generation of $PO_x$ and $PH_3$ by a disproportionation reaction during the early part of the run.

In the run of Example 118, the initial catalyst loading was 10 mole % Cu. After two hours reaction time, the batch was interrupted, vented and cooled down as described hereinabove. When heated back to 100° C., the reaction proceeded at the high initial rate for 17 more hours, at which point heat was again removed. Analysis of the reaction head space after the second reaction period revealed no detectable $PH_3$, a notable result since it reflects rapid catalytic oxidation of $P_4$ without appreciable generation of $PH_3$.

What is claimed is:

1. A process for the preparation of $H_2$ and phosphorous acid, the process comprising catalytically oxidizing elemental phosphorus by reaction with water at a temperature below 200° C.

2. A process as set forth in claim 1 wherein the reaction is conducted in a reaction zone comprising a metal catalyst.

3. A process as set forth in claim 2 wherein the reaction is conducted in a reaction zone comprising a noble metal catalyst.

4. A process as set forth in claim 1 wherein said reaction is conducted in a reaction zone comprising a catalyst comprising a material selected from the group consisting of Group IB metals, Group VIII metals, oxides of Group IB metals, oxides of Group VIII metals, salts of Group IB metals, salts of Group VIII metals, phosphides of Group IB metals, phosphides of Group VIII metals, co-ordination compounds of Group IB metals, and co-ordination compounds of Group VIII metals.

5. A process as set forth in claim 1 wherein said reaction is conducted in a reaction zone comprising a catalyst comprising an organometallic compound.

6. A process as set forth in claim 1 wherein:
said elemental phosphorus comprises tetraphosphorus, and
said reaction is conducted in a heterogeneous reaction system in which a tetraphosphorus-containing phase is contacted with a separate aqueous phase.

7. A process as set forth in claim 6 wherein said catalyst is predominantly distributed to the phase comprising tetraphosphorus.

8. A process as set forth in claim 7 wherein said catalyst comprises a noble metal catalyst.

9. A process as set forth in claim 7 wherein said catalyst is substantially contained within said phase comprising tetraphosphorus.

10. A process as set forth in claim 9 wherein the reaction is conducted at a temperature of between the melting point of tetraphosphorus and about 200° C.

11. A process as set forth in claim 10 wherein the product of the reaction comprises a solution of phosphorous acid and phosphoric acid in the aqueous phase, the molar ratio of phosphorous acid to phosphoric acid in said reaction product being at least about five.

12. A process as set forth in claim 11 wherein:
the product of the reaction comprises a solution comprising phosphorous acid, hypophosphorous acid and phosphoric acid in the aqueous phase; and
the molar ratio of the sum of the phosphorous acid and the hypophosphorous acid content of the reaction product to the phosphoric acid content of the reaction product is at least about eight.

13. A process as set forth in claim 11 wherein said catalyst comprises a material selected from the group consisting of Group IB metals, Group VIII metals, oxides of Group IB metals, oxides of Group VIII metals, salts of Group EB metals, salts of Group VIII metals, phosphides of Group IB metals, phosphides of Group VIII metals, co-ordination compounds of Group IB metals, and co-ordination compounds of Group VIII metals.

14. A process as set forth in claim 13 wherein said catalyst comprises a platinum metal.

15. A process as set forth in claim 11 wherein said catalyst comprises palladium.

16. A process as set forth in claim 11 wherein said catalyst comprises a material selected from the group consisting of Group IB metals, oxides of Group IB metals, salts of Group IB metals, and phosphides of Group IB metals.

17. A process as set forth in claim 11 wherein said catalyst comprises copper metal, copper chloride, copper nitrate, copper sulfate, copper oxide, copper phosphide, or mixtures thereof.

18. A process as set forth in claim 11 wherein said catalyst comprises a metal selected from the group consisting of a noble metal, Cu, Co, and Ni.

19. A process as set forth in claim 11 wherein said catalyst comprises a ligated transition metal.

20. A process as set forth in claim 11 wherein said catalyst comprises a ligated metal homogeneous with said phosphorous phase.

21. A process as set forth in claim 7 wherein:
said catalyst comprises a heterogeneous catalyst; and
said reaction system is agitated at a rate sufficient to promote mass transfer between the aqueous phase and the phase comprising tetraphosphorus, but insufficient to cause entrainment of said heterogeneous catalyst in the aqueous phase to an extent that would cause the molar ratio of phosphorous acid to phosphoric acid in said reaction product to be less than about five.

22. A process as set forth in claim 21 wherein the phase comprising tetraphosphorus is present in the heterogeneous reaction system as a liquid pool positioned below at least a portion of said aqueous phase, and the agitation is sufficient to continually break globules of said tetraphosphorus phase off said liquid pool.

23. A process as set forth in claim 21 wherein:
the product of the reaction comprises a solution comprising phosphorous acid, hypophosphorous acid, and phosphoric acid in the aqueous phase; and
the molar ratio of the sum of the phosphorous acid and the hypophosphorous acid content of the reaction product to the phosphoric acid content of the reaction product is at least about eight.

24. A process as set forth in claim 21 wherein:
the catalyst comprises Pd, and
the Pd content of said aqueous phase is less than about 200 ppm substantially throughout the course of oxidation of tetraphosphorus with water.

25. A process as set forth in claim 7 wherein the combination of the effective concentration of active catalyst sites in contact with said phase comprising tetraphosphorus, the effective concentration of catalyst sites in contact with said aqueous phase, and the temperature of said system are effective to produce a reaction product containing at least five moles phosphorous acid per mole phosphoric acid.

26. A process as set forth in claim 7 wherein the combination of catalyst distribution within said reaction system, temperature, and agitation of said system are controlled to provide a reaction product containing at least five moles phosphorous acid per mole phosphoric acid.

27. A process as set forth in claim 26 wherein the molar ratio of phosphorous acid to phosphoric acid in said reaction product is at least about eight.

28. A process as set forth in claim 27 wherein the molar ratio of phosphorous acid to phosphoric acid in said reaction product is at least about nine.

29. A process as set forth in claim 26 wherein:
the product of the reaction comprises a solution of phosphorous acid, hypophosphorous acid, and phosphoric acid in the aqueous phase; and
the molar ratio of the sum of the phosphorous acid and the hypophosphorous acid content of the reaction product to the phosphoric content of the reaction product is at least about eight.

30. A process as set forth in claim 6 wherein said phase comprising tetraphosphorus comprises a solution of tetraphosphorus in an organic solvent.

31. A process as set forth in claim 6 wherein said catalyst comprises palladium.

32. A process as set forth in claim 31 wherein the palladium active sites are predominantly distributed to the phase comprising tetraphosphorus.

33. A process as set forth in claim 6 wherein:

a precursor mixture is prepared comprising an aqueous phase, a substantially water-immiscible liquid phase comprising tetraphosphorus, and a noble metal catalyst; and said precursor mixture is agitated to cause the noble metal catalyst to be substantially distributed to the phase comprising tetraphosphorus, tetraphosphorus being thereafter selectively oxidized to phosphorous acid by catalytic oxidation of tetraphosphorus with water.

34. A process as set forth in claim 33 wherein agitation of said precursor mixture causes noble metal catalyst initially contained within said aqueous phase to be transferred to said phase comprising tetraphosphorus.

35. A process as set forth in claim 34 wherein the agitation of said precursor mixture is effective to distribute noble metal catalyst to the phase comprising tetraphosphorus to an extent sufficient that catalytic oxidation of tetraphosphorus produces a reaction product in which the molar ratio of phosphorous acid to phosphoric acid is at least about five.

36. A process as set forth in claim 6 wherein a premixture is prepared by mixing a liquid comprising molten tetraphosphorus with said catalyst, and said premixture is thereafter contacted with an aqueous liquid to provide said heterogeneous reaction system.

37. A process as set forth in claim 36 wherein said catalyst comprises a noble metal catalyst.

38. A process as set forth in claim 36 wherein preparing said premixture and thereafter contacting said premixture with said aqueous liquid is effective to distribute the catalyst to the phase comprising tetraphosphorus to an extent sufficient that catalytic oxidation of tetraphosphorus produces a reaction product in which the molar ratio of phosphorous acid to phosphoric acid is at least about five.

39. A process as set forth in claim 38 wherein the liquid phase of said premixture is allowed to solidify before contact of said premixture with said aqueous liquid.

40. A process as set forth in claim 36 wherein said premixture is prepared under an inert atmosphere.

41. A process as set forth in claim 36 wherein said premixture is contacted with hydrogen for reduction of the catalyst contained therein.

42. A process as set forth in claim 6 wherein:

an initial precursor mixture is prepared comprising an aqueous phase, a substantially water-immiscible liquid phase comprising tetraphosphorus, and catalyst;

the liquid phases of said initial precursor mixture are separated, thereby removing catalyst that has become distributed to the aqueous phase; and the substantially water-immiscible liquid phase is further contacted with an aqueous liquid to provide said heterogeneous reaction system.

43. A process as set forth in claim 42 wherein, after separation of the liquid phases of said initial precursor mixture, said water-immiscible liquid phase is contacted with an aqueous liquid to provide a second precursor mixture, and the liquid phases of said second precursor mixture are separated prior to contacting said water-immiscible phase with an aqueous liquid to provide said heterogeneous reaction system.

44. A process as set forth in claim 42 wherein said water-immiscible liquid phase is contacted with aqueous liquid in a series of stages for purging of catalyst distributed to the aqueous phase, thereby producing a series of precursor mixtures, the liquid phases of each of the precursor mixtures being separated before the water-immiscible liquid phase is contacted with an aqueous liquid in any successive stage of said series of purging stages, the water-immiscible liquid phase from the last of said purging stages being mixed with an aqueous liquid to provide said heterogeneous reaction system.

45. A process as set forth in claim 42 wherein the concentration of active catalyst sites in contact with the aqueous phase of said heterogeneous reaction system is sufficiently low so that catalytic oxidation of tetraphosphorus produces a reaction product in which the molar ratio of phosphorous acid to phosphoric acid is at least about five.

46. A process as set forth in claim 6 wherein:

said catalyst comprises a noble metal catalyst, and said noble metal catalyst is in a substantially reduced state during the course of catalytic oxidation of tetraphosphorus by reaction with water.

47. A process as set forth in claim 46 wherein said catalyst is reduced prior to incorporation in said heterogeneous reaction system.

48. A process as set forth in claim 47 wherein said catalyst is reduced by contact with hydrogen.

49. A process as set forth in claim 48 wherein said catalyst is reduced by contact with hydrogen in a methanol or water medium.

50. A process as set forth in claim 48 wherein reduction of said catalyst comprises reacting hypophosphorous acid with water in a reaction zone comprising the catalyst.

51. A process as set forth in claim 50 comprising the steps of:

contacting an aqueous solution of hypophosphorous acid with said catalyst at a temperature effective for formation of hydrogen by conversion of hypophosphorous acid to phosphorous acid, thereby causing reduction of said catalyst by reaction with hydrogen; and mixing a phase containing tetraphosphorus with the reduced catalyst and an aqueous liquid to provide said heterogeneous reaction system wherein tetraphosphorus is oxidized.

52. A process as set forth in claim 51 wherein the aqueous liquid comprises a solution comprising phosphorous acid, hypophosphorous acid and phosphoric acid produced in the reduction of said catalyst.

53. A process as set forth in claim 48 wherein the product of the reaction comprises a solution of phosphorous acid in the aqueous phase, the process further comprising contacting the catalyst with hydrogen in a pretreatment zone before the catalyst is introduced into said heterogeneous reaction system, hydrogen generated in the oxidation of hypophosphorous acid to phosphorous acid in said heterogeneous reaction system being recycled to said pretreatment zone for reduction of said catalyst therein.

54. A process as set forth in claim 46 in which the product of the reaction comprises an aqueous solution comprising phosphorous acid, hypophosphorous acid and phosphoric acid in which the molar ratio of phosphorous acid to phosphoric acid is at least about five.

55. A process as set forth in claim 6 wherein:
the catalyst comprises a noble metal catalyst, and
the heterogeneous reaction system is agitated at a temperature effective to promote transfer of noble metal catalyst from the aqueous phase to the phase comprising tetraphosphorus.

56. A process as set forth in claim 1 wherein the phosphorus oxidation reaction product comprises a crude aqueous product phase further containing hypophosphorous acid, the process further comprising oxidation of hypophosphorous acid by reaction with water in a reaction zone comprising a catalyst in contact with said crude aqueous phase to produce a further aqueous oxidation reaction product comprising an aqueous solution of phosphorous acid in which the molar ratio of hypophosphorous acid to phosphorous acid is not greater than about 0.2.

57. A process as set forth in claim 56 wherein said molar ratio of hypophosphorous acid to phosphorous acid is not greater than about 0.05.

58. A process as set forth in claim 57 wherein said molar ratio of hypophosphorous acid to phosphorous acid is between about 0.01 and about 0.02.

59. A process as set forth in claim 56 wherein the reaction is conducted in a reaction zone comprising a catalyst comprising a metal selected from the group consisting a noble metal, Cu, Co, and Ni.

60. A process as set forth in claim 59 wherein said catalyst comprises a metal selected from the group consisting of Pd, Pt, and Rh.

61. A process as set forth in claim 1 wherein said elemental phosphorus comprises tetraphosphorus, and the tetraphosphorus is contacted with water under an inert atmosphere.

62. A process as set forth in claim 61 wherein the water with which said tetraphosphorus is contacted is purged with an inert gas before catalytic oxidation of tetraphosphorus.

63. A process as set forth in claim 61 wherein said reaction is conducted in a heterogeneous reaction system in which a tetraphosphorus-containing phase is contacted with a separate aqueous phase.

64. A process as set forth in claim 1 wherein said catalyst comprises palladium.

65. A process as set forth in claim 64 wherein said catalyst comprises palladium black.

66. A process as set forth in claim 1 wherein:
a phosphorus phase comprising a substantially water-immiscible feed composition comprising tetraphosphorus is contacted with an aqueous phase in a liquid/liquid contact zone for transfer of water to the phosphorus phase at the interface of the phases; and
the phosphorus phase containing water transferred from the aqueousphase is contacted with a catalyst for oxidation of tetraphosphorus by reaction with water contained in the phosphorus phase.

67. A process as set forth in claim 66 comprising contacting said water-containing phosphorus phase with noble metal catalyst in a catalytic reaction zone spaced from said interface.

68. A process as set forth in claim 67 wherein said catalytic reaction zone comprises a fixed or fluidized catalyst bed.

69. A process as set forth in claim 68 where said phosphorus phase is circulated between said liquid/liquid contact zone and said catalytic reaction zone.

70. A process as set forth in claim 69 wherein a product solution comprising phosphorous acid, hypophosphorous acid and phosphoric acid is continuously or intermittently removed from said liquid/liquid contact zone, and water is continuously or intermittently introduced into said liquid/liquid contact zone.

71. A process as set forth in claim 70 wherein tetraphosphorus is continuously or intermittently introduced into said liquid/liquid contact zone.

72. A process as set forth in claim 66 wherein said catalyst is contacted with said phosphorus phase in said liquid/liquid contact zone at a location remote from said liquid/liquid interface.

73. A process as set forth in claim 72 wherein a product solution comprising phosphorous acid, hypophosphorous acid and phosphoric acid is continuously or intermittently removed from said liquid/liquid contact zone, and water is continuously or intermittently introduced into said liquid/liquid contact zone.

74. A process as set forth in claim 73 wherein tetraphosphorus is continuously or intermittently introduced into said liquid/liquid contact zone.

75. A process as set forth in claim 72 wherein the reaction is carried out in a vessel comprising said liquid/liquid contact zone and said catalytic reaction zone, said reaction zone being disposed within said phosphorus phase or on a wall of the reactor with which the phosphorus phase is in contact.

76. A process as set forth in claim 72 said catalyst is disposed within said phosphorus phase.

77. A process as set forth in claim 76 wherein said catalyst is slurried in said phosphorus phase.

78. A process as set forth in claim 76 in which said catalyst is dissolved in said phosphorus phase.

79. A process as set forth in claim 76 wherein said catalyst is contained in a fixed bed disposed within said phosphorus phase.

80. A process as set forth in claim 66 wherein said feed composition comprises tetraphosphorus dissolved in an organic solvent.

81. A process as set forth in claim 1 wherein a phosphorus phase containing a noble metal catalyst is contacted with an aqueous phase in a countercurrent liquid/liquid contact zone.

82. A process as set forth in claim 81 wherein said phosphorus phase is circulated between said countercurrent liquid/liquid contact zone and reservoir for said phosphorus phase.

83. A process as set forth in claim 81 wherein an aqueous phase reaction product comprising phosphorous acid, hypophosphorous acid and phosphoric acid is withdrawn from said liquid/liquid contact zone and introduced into a finishing reaction zone containing a noble metal catalyst.

84. A process as set forth in claim 83 wherein said finishing reaction zone comprises a fixed catalyst bed comprising said noble metal catalyst.

85. A process as set forth in claim 83 wherein a finished solution comprising phosphorous acid, hypophosphorous acid and phosphoric acid exiting said finishing reaction zone is concentrated by evaporation of water therefrom.

86. A process as set forth in claim 81 wherein an aqueous phase reaction product comprising phosphorous acid, hypoqhosphorous acid and phosphoric acid is withdrawn from said liquid/liquid contact zone and introduced into a finishing reaction zone containing a carbon catalyst.

87. A process as set forth in claim 81 wherein an aqueous phase reaction product comprising phosphorous acid, hypophosphorous acid and phosphoric acid is withdrawn from said liquid/liquid contact zone and introduced into a liquid/liquid separator for separation of phosphorus phase entrained in said aqueous phase reaction product.

88. A process as set forth in claim 87 wherein phosphorus phase separated from said aqueous phase reaction product is recycled to said liquid/liquid contact zone.

89. A process as set forth in claim 1 wherein the reaction is conducted at a temperature between about 2° and about 10° C. below the threshold temperature at which selectivity to formation of phosphorous acid and hypophophorous acid versus phosphoric acid begins sharply to deteriorate.

90. A process as set forth in claim 1 wherein said reaction is conducted in a catalytic reaction zone comprising an aqueous phase, a phase comprising elemental phosphorus, and a catalyst for the reaction, and sonic and/or microwave energy is introduced into the reaction zone during the reaction.

91. A process as set forth in claim 1 wherein said reaction is contacted in a reaction system comprising an aqueous phase and a phase comprising phosphorus, said aqueous phase containing not more than between about 10 and about 50 ppm metals.

92. A process for the preparation of phosphorous acid comprising catalytically oxidizing elemental phosphorus by reaction with water in a reaction zone comprising a metal-containing catalyst under conditions effective to produce an oxidation reaction mixture comprising phosphorous acid, hypophosphorous acid and phosphoric acid, the molar ratio of the sum of the concentrations of phosphorous acid and hypoohosphorous acid to the concentration of phosphoric acid in said reaction mixture being least about five.

93. A process as set forth in claim 92 wherein the conversion of phosphorus to phosphorous acid, hypophosphorous acid and phosphoric acid is at least about 2%.

94. A process as set forth in claim 93 wherein the conversion of phosphorus to phosphorous acid, hytophosphorous acid and phosphoric acid is at least about 5%.

95. A process as set forth in claim 93 wherein the conversion of phosphorus to phosphorous acid, hypophosphorous acid and phosphoric acid is at least about 15%.

96. A process as set forth in claim 133 wherein the conversion of phosphorus to phosphorous acid, hypophosphorous acid and phosphoric acid is at least about 25%.

97. A process as set forth in claim 92 wherein said ratio is at least about eight.

98. A process for the preparation of phosphorous acid, the process comprising contacting condensed phase elemental phosphorus with water at a pressure below about 20 atm in a reaction zone comprising a metal-containing catalyst for the oxidation of phosphorus by reaction with water.

99. A process for the preparation of phosphorous acid, the process comprising contacting elemental phosphorus with water in a reaction zone comprising a solid phase catalyst for the oxidation of phosphorus by reaction with water, wherein said catalyst comprises an active phase having a B.E.T. surface area of at least about 60 $m^2/g$.

100. A process for the preparation of phosphorous acid, the process comprising catalytically oxidizing elemental phosphorus by reaction with water in a catalytic reaction zone comprising a metal-containing catalyst to produce a lower phosphorus oxidation product at a rate of at least 0.01 kg/hr per unit volume of said reaction zone as expressed in $m^3$.

101. A process as set forth in claim 100 wherein an oxidation reaction mixture is produced in which the molar ratio of the sum of the concentrations of phosphorous acid and hypophosphorous acid to the concentration of phosphoric acid is at least about five.

102. A process for the preparation of phosphorous acid, the process comprising catalytically oxidizing elemental phosphorus in a catalytic reaction zone comprising a metal-containing catalyst to produce an oxidation product comprising phosphorous acid and hypophosphorous acid at a rate of at least $1\times10^{-7}$ kg/hr-g catalyst.

103. A process as set forth in claim 102 wherein an oxidation reaction mixture is produced in which the molar ratio of the sum of the concentrations of phosphorous acid and hypophosphorous acid to the concentration of phosphoric acid is at least about five.

104. A process for the preparation of phosphorous acid comprising contacting elemental phosphorus with water in a reaction zone comprising a metal-containing catalyst for the oxidation of phosphorus by reaction with water, thereby producing an aqueous reaction mixture containing at least about 2% by weight of an oxidation product comprising phosphorous acid and hypophosphorous acid, the reaction between phosphorus and water being conducted in a heterogeneous reaction system comprising a water phase and a condensed phase comprising elemental phosphorus, said condensed phase containing said catalyst.

105. A process as set forth in claim 104 wherein said catalyst is predominantly distributed to said condensed phase comprising elemental phosphorus.

106. A process as set forth in claim 105 wherein the distribution of catalyst is effective at the temperature of the reaction to produce a reaction mixture in which the molar ratio of the sum of the concentration of phosphorous acid and hypophosphorous acid to the concentration of phosphoric acid is at least about five.

107. A process as set forth in claim 106 wherein the conversion of phosphorus to phosphorous acid, hypophosphorous acid and phosphoric acid is at least about 2%.

108. A process As set forth in claim 104 comprising the steps of:

preparing a condensed phase mixture comprising elemental phosphorus and said catalyst; and contacting said condensed phase mixture with water.

109. A process for the preparation of phosphorous acid, the process comprising contacting a condensed phase comprising elemental phosphorus with an aqueous phase in a reaction zone comprising a catalyst for the oxidation of phosphorus by reaction with water, active sites of the catalyst being maintained in contact with the condensed phase comprising phosphorus preferentially to said aqueous phase during the catalytic oxidation reaction.

110. A process as set forth in claim 109 wherein said active sites are maintained substantially out of contact with the aqueous phase.

111. A process as set forth in claim 104 wherein the relative concentrations of active catalyst sites respectively in contact with said aqueous phase and said phosphorus phase are effective at the temperature of the reaction to produce an oxidation reaction mixture in which the molar ratio of the sum of the concentrations of phosphorous acid and hypophosphorous acid to the concentration of phosphoric acid is at least about five.

112. A process as set forth in claim 111 wherein said conversion of phosphorus to phosphorous acid, hypophosphorous acid and phosphoric acid is at least about 2%.

113. A process for the preparation of phosphorous acid comprising contacting a condensed phase comprising elemental phosphorus with an aqueous phase in a reaction zone comprising a metal-containing catalyst for the oxidation of phosphorus by reaction with water, wherein the rate of oxidation of elemental phosphorus in said elemental phosphorus phase is greater than the rate of oxidation of elemental phosphorus in said aqueous phase.

114. A process as set forth in claim 113 wherein:

the reaction is conducted in a reaction zone comprising a heterogenous catalyst comprising said active sites on the surface thereof, and elemental phosphorus is adsorbed at the active sites preferentially to the absorption of water.

115. A process as set forth in claim 113 wherein elemental phosphorus is adsorbed on the surface of said catalyst preferentially to water to an extent effective at the temperature of the reaction to produce a reaction mixture in which the molar ratio of the sum of the concentrations of phosphorous acid and hypophosphorous acid to the concentration of phosphoric acid is at least about five.

116. A process as set forth in claim 115 wherein said conversion of phosphorus to phosphorous acid, hypophosphorous acid and phosphoric acid is at least about 2%.

117. A process for the preparation of phosphorous acid, the process comprising oxidizing elemental phosphorus by catalytic reaction with water in a reaction zone comprising a metal-containing catalyst at a temperature below a threshold temperature at which the ratio of the sum of the rates of formation of phosphorous acid and hypophosphorous acid to the rate of formation of phosphoric acid drops to 3.0 in a batch reaction system at 25% conversion of elemental phosphorus.

118. A process as set forth in claim 117 wherein the reaction is conducted at a temperature between about 0.5° C. and about 20° C. below said threshold temperature.

119. A process as set forth in claim 117 wherein the reaction is conducted at a temperature between about 2° C. and about 10° C. below said threshold temperature.

120. A process as set forth in claim 117 wherein the reaction is conducted in a batch mode.

121. A process as set forth in claim 117 wherein the reaction is conducted in a continuous back mixed mode.

122. A process as set forth in claim 117 wherein the reaction is conducted in a continuous plug flow mode with respect to the aqueous phase of the reaction system.

123. A process for the preparation of phosphorous acid, the process comprising catalytically oxidizing elemental phosphorus by reaction with water in a catalytic reaction zone comprising water, a phase containing elemental phosphorus and a catalyst for the reaction, sonic and/or microwave energy being introduced into said reaction zone during the reaction.

124. A process as set forth in claim 1 wherein said reaction is conducted in a reaction zone comprising a catalyst comprising a material selected from the group consisting of platinum-group metals, oxides of platinum-group metals, salts of platinum-group metals, and co-ordination compounds of platinum-group metals.

125. A process as set forth in claim 11 wherein said catalyst comprises a material selected from the group consisting of platinum-group metals, oxides of platinum-group metals, salts of platinum-group metals, and co-ordination compounds of platinum-group metals.

126. A process as set forth in claim 11 wherein said catalyst comprises a ligated metal selected from the group consisting of platinum-group metals and Group IB metals.

127. A process as set forth in claim 72 wherein said aqueous phase flows across an upper surface of said phosphorus phase at said liquid/liquid interface in said liquid/liquid contact zone, while a lower surface of said phosphorus phase is in contact with said catalyst.

* * * * *